US008029979B2

(12) United States Patent
Schneider-Mergener et al.

(10) Patent No.: US 8,029,979 B2
(45) Date of Patent: Oct. 4, 2011

(54) METHOD FOR DETERMINING THE SUBSTRATE SPECIFICITY OF AN ENZYME

(75) Inventors: Jens Schneider-Mergener, Berlin (DE); Mike Schutkowski, Zielgelroda (DE); Ulf Reimer, Berlin (DE); Liying Dong, Berlin (DE); Soren Panse, Berlin (DE); Dirk Scharn, Berlin (DE); Frank Osterkamp, Berlin (DE); Gerd Hummel, Berlin (DE); Laurence Jobron, Berlin (DE)

(73) Assignee: JPT Peptide Technologies GmbH, Berlin (DE)

( * ) Notice: Subject to any disclaimer, the term of this patent is extended or adjusted under 35 U.S.C. 154(b) by 0 days.

(21) Appl. No.: 11/474,283

(22) Filed: Jun. 26, 2006

(65) Prior Publication Data

US 2006/0234308 A1     Oct. 19, 2006

Related U.S. Application Data

(63) Continuation of application No. 10/475,104, filed as application No. PCT/EP02/04265 on Apr. 17, 2002, now abandoned.

(30) Foreign Application Priority Data

Apr. 17, 2001    (DE) .................................. 101 18 774

(51) Int. Cl.
*C12Q 1/00*     (2006.01)
(52) U.S. Cl. .............................. 435/4; 435/176; 435/183
(58) Field of Classification Search .............. 435/4, 183, 435/176
See application file for complete search history.

(56) References Cited

U.S. PATENT DOCUMENTS

| | | | |
|---|---|---|---|
| 6,766,817 B2 | 7/2004 | da Silva | |
| 6,872,560 B1 * | 3/2005 | Yue et al. | ....................... 435/226 |
| 2001/0031469 A1 * | 10/2001 | Volinia | .............................. 435/6 |
| 2003/0138895 A1 * | 7/2003 | Tang et al. | .................... 435/69.1 |
| 2004/0023245 A1 * | 2/2004 | Au-Young et al. | ................. 435/6 |

FOREIGN PATENT DOCUMENTS

WO     WO 00/54046 A2     9/2000

OTHER PUBLICATIONS

MacBeath G. et al. Printing Proteins as Microarrays for High Throughput Function Determination. Science vol. 289, pp. 1760-1763, Sep. 8, 2000.*
MacBeath G. et al. Printing Proteins as Microarrays for High Throughput Function Determination. Science USA. 289(5485)1760-1763, Sep. 8, 2000.*
Johnsson B. Immobilization of Proteins . . . Analytical Biochemistry 198(2)268-277, Nov. 2, 1991.*
Reineke U. et al. Applications of Peptide Arrays Prepared by the SPOT Technology. Current Opinion in Biotechnology England. 12(1)59-64, Feb. 2001.*
"C-FIT™-A Radical New Technology", NANO Type, Online!, Apr. 3, 2001, pp. 1-2, XP-002234263.
Arenkov P. et al., "Protein Microchips: Use for Immunoassay and Enzymatic Reactions" *Analytical Biochemistry*, 2000, vol. 278, pp. 123-131, XP-002234264.
Haab B. B. et al., "Protein Microarrays for Highly Parallel Detection and Quantitation of Specific Proteins and Antibodies in Complex Solutions" *Genome Biology*, 2001, vol. 2, No. 2, pp. 1-13, XP-002234266.
Lemieux G. A., and Bertozzi C. R., "Chemoselective Ligation Reactions With Proteins, Oligosaccharides and Cells" *Trends In Biotechnology*, 1998, vol. 16, No. 12, pp. 506-513, XP-002234265.
Macbeath G. and Schreiner S. L., "Printing Proteins as Microarrays for High-Throughput Function Determination" *Science*, U.S., 2000, vol. 289, No. 5485, pp. 1760-1763, XP-002234262.
Reineke U. et al., "Applications of Peptide Arrays Prepared by the SPOT-Technology" Current Opinion in Biotechnology. England, Feb. 2001, vol. 12, No. 1, pp. 59-64, XP-002234261.
MacBeath G., et al., "Printing Proteins as Microarrays for High Throughput Function Determination", Science USA, 289(5485)1760-1763, Sep. 8, 2000.
Johnsson B. "Immobilization of Proteins . . . ", Analytical Biochem 198(2) 268-277, Nov. 2, 1991.
Reineke et al., "Applications of Peptide Arrays Prepared by the SPOT Technology", Current Opinion in Biotechnology England, 12(1)59-64, Feb. 2001.
Gast et al., "Method for Determining Protein Kinase Substrate Specificities by the Phosphorylation of Peptide Libraries on Beads, Phosphate-Specific Straining, Automated Sorting, and Sequencing", Anal. Biochem., (1999), vol. 276 [2], pp. 227-241.
Zhu et al, "Analysis of yeast protein kinases using protein chips", Nature Genet., (2000) 26, [3], p. 283-289.

* cited by examiner

*Primary Examiner* — Ralph Gitomer
(74) *Attorney, Agent, or Firm* — McAndrews, Held & Malloy Ltd.

(57) ABSTRACT

The invention relates to a method for determining the substrate specificity of an enzymatic activity comprising the following steps: providing an assembly comprising a plurality of amino acid sequences on a planar surface of a support material, whereby the amino acids are directionally immobilized; contacting and/or incubating of an enzymatic activity with the assembly; and detection of a reaction between one of the amino acid sequences that are immobilized on the assembly and the enzymatic activity. According to the invention, during the reaction of the enzymatic activity with the assembly, a change in the molecular weight of at least one of the amino acid sequences takes place.

14 Claims, 12 Drawing Sheets

Fig.11A
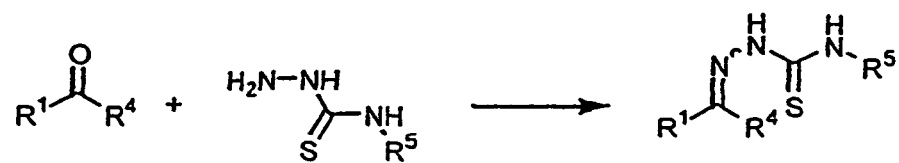
Fig.11B
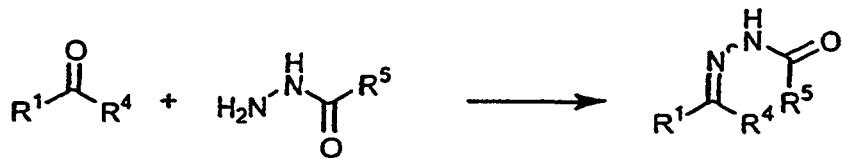
Fig.11C
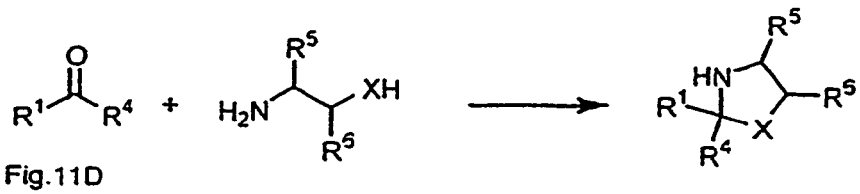
Fig.11D
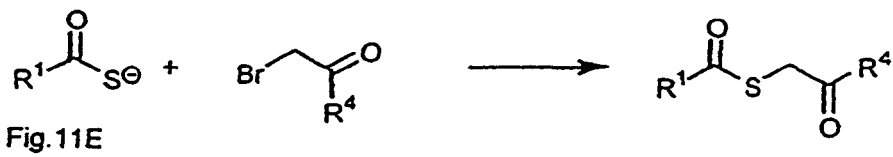
Fig.11E
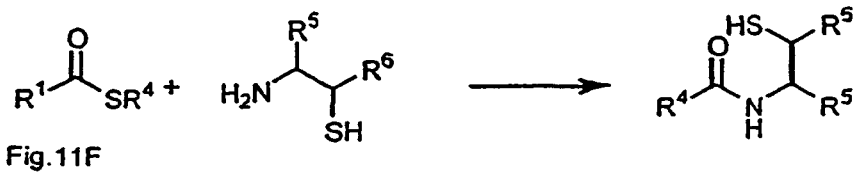
Fig.11F
Fig.11G
Fig. 11

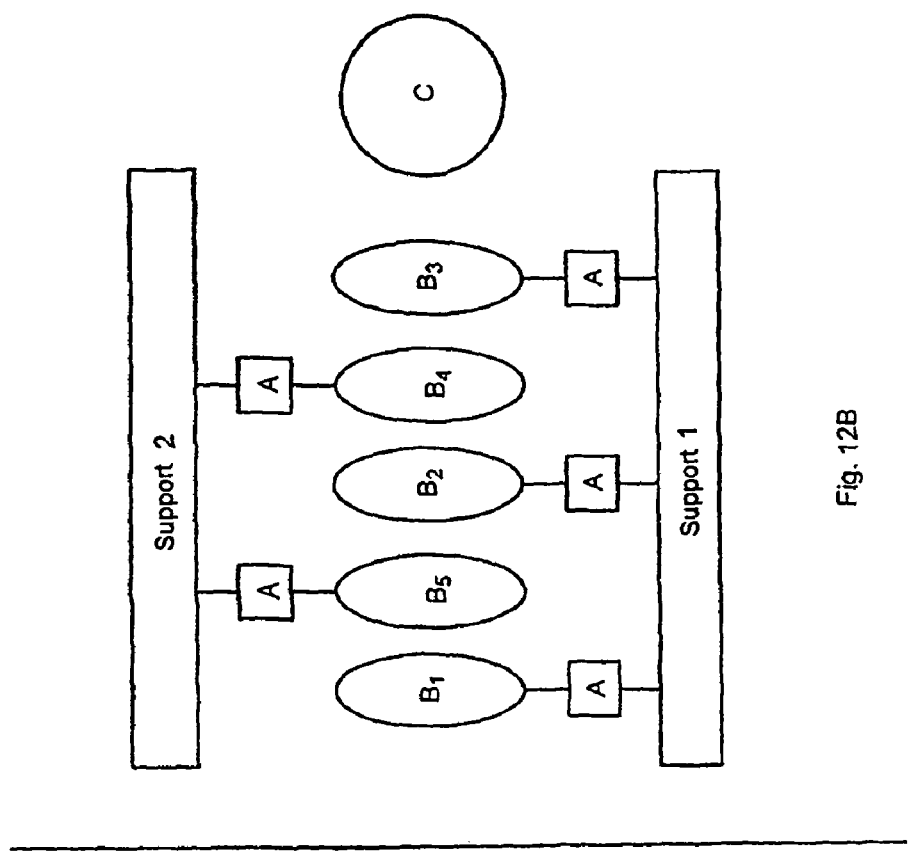
Fig. 12B
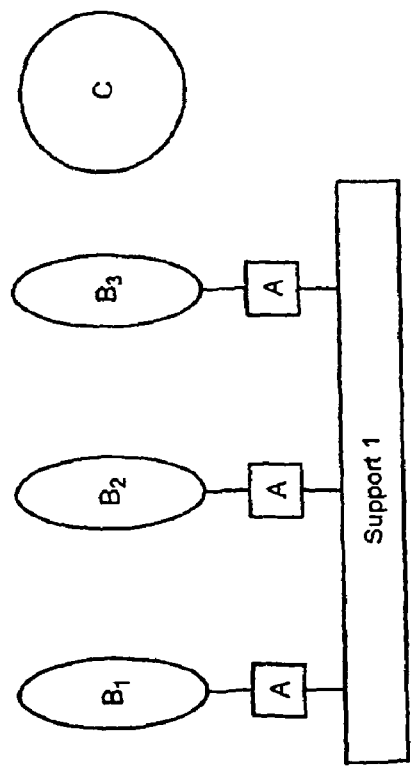
Fig. 12A
Fig. 12

SEQUENCE LISTING

<160> NUMBER OF SEQ ID NOS: 144

<210> SEQ ID NO 1
<211> LENGTH: 4
<212> TYPE: PRT
<213> ORGANISM: Unknown
<220> FEATURE:
<223> OTHER INFORMATION: cell-adhesive peptide

<400> SEQUENCE: 1

Arg Gly Asp Cys
1

<210> SEQ ID NO 2
<211> LENGTH: 18
<212> TYPE: PRT
<213> ORGANISM: Unknown
<220> FEATURE:
<223> OTHER INFORMATION: kinase substrate

<400> SEQUENCE: 2

Arg Arg Lys Asp Leu His Asp Asp Glu Glu Asp Glu Ala Met Ser Ile
1               5                   10                  15

-continued

Thr Ala

<210> SEQ ID NO 3
<211> LENGTH: 9
<212> TYPE: PRT
<213> ORGANISM: Unknown
<220> FEATURE:
<223> OTHER INFORMATION: kinase substrate

<400> SEQUENCE: 3

Gln Lys Arg Pro Ser Gln Arg Ser Lys
1               5

<210> SEQ ID NO 4
<211> LENGTH: 7
<212> TYPE: PRT
<213> ORGANISM: Unknown
<220> FEATURE:
<223> OTHER INFORMATION: kinase substrate

<400> SEQUENCE: 4

Leu Arg Arg Ala Ser Leu Gly
1               5

<210> SEQ ID NO 5
<211> LENGTH: 7
<212> TYPE: PRT
<213> ORGANISM: Unknown
<220> FEATURE:
<223> OTHER INFORMATION: peptide/ control peptide
<220> FEATURE:
<221> NAME/KEY: MOD_RES
<222> LOCATION: (7)..(7)
<223> OTHER INFORMATION: amino group

<400> SEQUENCE: 5

Leu Arg Arg Ala Ser Leu Gly
1               5

<210> SEQ ID NO 6
<211> LENGTH: 7
<212> TYPE: PRT
<213> ORGANISM: Unknown
<220> FEATURE:
<223> OTHER INFORMATION: peptide/ control peptide
<220> FEATURE:
<221> NAME/KEY: MOD_RES
<222> LOCATION: (7)..(7)
<223> OTHER INFORMATION: amino group

<400> SEQUENCE: 6

Leu Arg Arg Ala Ala Leu Gly
1               5

<210> SEQ ID NO 7
<211> LENGTH: 7
<212> TYPE: PRT
<213> ORGANISM: Unknown
<220> FEATURE:
<223> OTHER INFORMATION: peptide/ control peptide
<220> FEATURE:
<221> NAME/KEY: MOD_RES
<222> LOCATION: (7)..(7)
<223> OTHER INFORMATION: thioamide

<400> SEQUENCE: 7

Leu Arg Arg Ala Ser Leu Gly
1               5

```
<210> SEQ ID NO 8
<211> LENGTH: 8
<212> TYPE: PRT
<213> ORGANISM: Unknown
<220> FEATURE:
<223> OTHER INFORMATION: peptide/ control peptide
<220> FEATURE:
<221> NAME/KEY: MISC_FEATURE
<222> LOCATION: (1)..(1)
<223> OTHER INFORMATION: Dpr (amino oxyacetic acid)
<220> FEATURE:
<221> NAME/KEY: MOD_RES
<222> LOCATION: (8)..(8)
<223> OTHER INFORMATION: amino group

<400> SEQUENCE: 8

Xaa Leu Arg Arg Ala Ser Leu Gly
1               5

<210> SEQ ID NO 9
<211> LENGTH: 11
<212> TYPE: PRT
<213> ORGANISM: Unknown
<220> FEATURE:
<223> OTHER INFORMATION: protein kinase C substrate

<400> SEQUENCE: 9

Ala Lys Arg Arg Arg Leu Ser Ser Leu Arg Ala
1               5                   10

<210> SEQ ID NO 10
<211> LENGTH: 12
<212> TYPE: PRT
<213> ORGANISM: Unknown
<220> FEATURE:
<223> OTHER INFORMATION: protein kinase C substrate

<400> SEQUENCE: 10

Pro Leu Ser Arg Thr Leu Ser Val Ala Ala Lys Lys
1               5                   10

<210> SEQ ID NO 11
<211> LENGTH: 11
<212> TYPE: PRT
<213> ORGANISM: Unknown
<220> FEATURE:
<223> OTHER INFORMATION: protein kinase C subtstrate

<400> SEQUENCE: 11

Gln Lys Arg Pro Ser Gln Arg Ser Lys Tyr Leu
1               5                   10

<210> SEQ ID NO 12
<211> LENGTH: 12
<212> TYPE: PRT
<213> ORGANISM: Unknown
<220> FEATURE:
<223> OTHER INFORMATION: protein kinase C substrate

<400> SEQUENCE: 12

Lys Lys Arg Phe Ser Phe Lys Lys Ser Phe Lys Leu
1               5                   10

<210> SEQ ID NO 13
<211> LENGTH: 9
<212> TYPE: PRT
<213> ORGANISM: Unknown
<220> FEATURE:
<223> OTHER INFORMATION: protein kinase C substrate
```

```
<400> SEQUENCE: 13

Pro Lys Asp Pro Ser Gln Arg Arg Arg
1               5

<210> SEQ ID NO 14
<211> LENGTH: 9
<212> TYPE: PRT
<213> ORGANISM: Unknown
<220> FEATURE:
<223> OTHER INFORMATION: not protein kinase C substrate

<400> SEQUENCE: 14

Gly Arg Thr Gly Arg Arg Asn Ser Ile
1               5

<210> SEQ ID NO 15
<211> LENGTH: 10
<212> TYPE: PRT
<213> ORGANISM: Unknown
<220> FEATURE:
<223> OTHER INFORMATION: not protein kinase C substrate

<400> SEQUENCE: 15

Asp Asp Asp Glu Glu Ser Ile Thr Arg Arg
1               5                   10

<210> SEQ ID NO 16
<211> LENGTH: 9
<212> TYPE: PRT
<213> ORGANISM: Unknown
<220> FEATURE:
<223> OTHER INFORMATION: not protein kinase C substrate

<400> SEQUENCE: 16

Glu Arg Ser Pro Ser Pro Ser Phe Arg
1               5

<210> SEQ ID NO 17
<211> LENGTH: 11
<212> TYPE: PRT
<213> ORGANISM: Unknown
<220> FEATURE:
<223> OTHER INFORMATION: not protein kinase C substrate

<400> SEQUENCE: 17

Gly Arg Pro Arg Thr Ser Ser Phe Ala Glu Gly
1               5                   10

<210> SEQ ID NO 18
<211> LENGTH: 13
<212> TYPE: PRT
<213> ORGANISM: Unknown
<220> FEATURE:
<223> OTHER INFORMATION: not protein kinase C substrate

<400> SEQUENCE: 18

Lys Lys Lys Ala Leu Ser Arg Gln Leu Ser Val Ala Ala
1               5                   10

<210> SEQ ID NO 19
<211> LENGTH: 10
<212> TYPE: PRT
<213> ORGANISM: Unknown
<220> FEATURE:
<223> OTHER INFORMATION: not protein kinase C substrate

<400> SEQUENCE: 19
```

Lys Lys Leu Asn Arg Thr Leu Ser Val Ala
1               5                   10

<210> SEQ ID NO 20
<211> LENGTH: 13
<212> TYPE: PRT
<213> ORGANISM: Unknown
<220> FEATURE:
<223> OTHER INFORMATION: not protein kinase C substrate

<400> SEQUENCE: 20

Lys Arg Arg Glu Ile Leu Ser Arg Arg Pro Ser Tyr Arg
1               5                   10

<210> SEQ ID NO 21
<211> LENGTH: 10
<212> TYPE: PRT
<213> ORGANISM: Unknown
<220> FEATURE:
<223> OTHER INFORMATION: not protein kinase C substrate

<400> SEQUENCE: 21

Pro Leu Ser Arg Thr Leu Ser Val Ser Ser
1               5                   10

<210> SEQ ID NO 22
<211> LENGTH: 7
<212> TYPE: PRT
<213> ORGANISM: Unknown
<220> FEATURE:
<223> OTHER INFORMATION: not protein kinase C substrate

<400> SEQUENCE: 22

Arg Pro Arg Ala Ala Thr Phe
1               5

<210> SEQ ID NO 23
<211> LENGTH: 13
<212> TYPE: PRT
<213> ORGANISM: Unknown
<220> FEATURE:
<223> OTHER INFORMATION: not protein kinase C substrate

<400> SEQUENCE: 23

Arg Phe Ala Arg Lys Gly Ser Leu Arg Gln Lys Asn Val
1               5                   10

<210> SEQ ID NO 24
<211> LENGTH: 9
<212> TYPE: PRT
<213> ORGANISM: Unknown
<220> FEATURE:
<223> OTHER INFORMATION: not protein kinase C substrate

<400> SEQUENCE: 24

Arg Glu Ala Arg Ser Arg Ala Ser Thr
1               5

<210> SEQ ID NO 25
<211> LENGTH: 13
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (2)..(2)
<223> OTHER INFORMATION: Xaa = beta-alanine -continued

```
<400> SEQUENCE: 25

Cys Xaa Ala Lys Arg Arg Leu Ser Ser Leu Arg Ala
1               5                   10

<210> SEQ ID NO 26
<211> LENGTH: 11
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (2)..(2)
<223> OTHER INFORMATION: Xaa = beta-alanine

<400> SEQUENCE: 26

Cys Xaa Gly Arg Thr Gly Arg Arg Asn Ser Ile
1               5                   10

<210> SEQ ID NO 27
<211> LENGTH: 13
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (2)..(2)
<223> OTHER INFORMATION: Xaa = beta-alanine

<400> SEQUENCE: 27

Cys Xaa Gly Arg Pro Arg Thr Ser Ser Phe Ala Glu Gly
1               5                   10

<210> SEQ ID NO 28
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (2)..(2)
<223> OTHER INFORMATION: Xaa = beta-alanine

<400> SEQUENCE: 28

Cys Xaa Lys Arg Arg Glu Ile Leu Ser Arg Arg Pro Ser Tyr Arg
1               5                   10                  15

<210> SEQ ID NO 29
<211> LENGTH: 13
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (2)..(2)
<223> OTHER INFORMATION: Xaa = beta-alanine

<400> SEQUENCE: 29

Cys Xaa Gln Lys Arg Pro Ser Gln Arg Ser Lys Tyr Leu
1               5                   10

<210> SEQ ID NO 30
<211> LENGTH: 15
<212> TYPE: PRT
<213> ORGANISM: Unknown
<220> FEATURE:
<223> OTHER INFORMATION: substrate peptide
```

```
<220> FEATURE:
<221> NAME/KEY: MISC_FEATURE
<222> LOCATION: (2)..(2)
<223> OTHER INFORMATION: Xaa = beta-alanine

<400> SEQUENCE: 30

Cys Xaa Arg Phe Ala Arg Lys Gly Ser Leu Arg Gln Lys Asn Val
1               5                   10                  15

<210> SEQ ID NO 31
<211> LENGTH: 9
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (2)..(2)
<223> OTHER INFORMATION: Xaa = beta-alanine

<400> SEQUENCE: 31

Cys Xaa Leu Arg Arg Ala Ser Leu Gly
1               5

<210> SEQ ID NO 32
<211> LENGTH: 169
<212> TYPE: PRT
<213> ORGANISM: Bos taurus

<400> SEQUENCE: 32

Ala Ala Gln Lys Arg Pro Ser Gln Arg Ser Lys Tyr Leu Ala Ser Ala
1               5                   10                  15

Ser Thr Met Asp His Ala Arg His Gly Phe Leu Pro Arg His Arg Asp
                20                  25                  30

Thr Gly Ile Leu Asp Ser Leu Gly Arg Phe Phe Gly Ser Asp Arg Gly
            35                  40                  45

Ala Pro Lys Arg Gly Ser Gly Lys Asp Gly His His Ala Ala Arg Thr
        50                  55                  60

Thr His Tyr Gly Ser Leu Pro Gln Lys Ala Gln Gly His Arg Pro Gln
65                  70                  75                  80

Asp Glu Asn Pro Val Val His Phe Phe Lys Asn Ile Val Thr Pro Arg
                85                  90                  95

Thr Pro Pro Pro Ser Gln Gly Lys Gly Arg Gly Leu Ser Leu Ser Arg
            100                 105                 110

Phe Ser Trp Gly Ala Glu Gly Gln Lys Pro Gly Phe Gly Tyr Gly Gly
        115                 120                 125

Arg Ala Ser Asp Tyr Lys Ser Ala His Lys Gly Leu Lys Gly His Asp
    130                 135                 140

Ala Gln Gly Thr Leu Ser Lys Ile Phe Lys Leu Gly Gly Arg Asp Ser
145                 150                 155                 160

Arg Ser Gly Ser Pro Met Ala Arg Arg
                165

<210> SEQ ID NO 33
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
```

```
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 33

Xaa Xaa Ala Ala Gln Lys Arg Pro Ser Gln Arg Ser Lys Tyr Leu
1               5                   10                  15

<210> SEQ ID NO 34
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 34

Xaa Xaa Gln Lys Arg Pro Ser Gln Arg Ser Lys Tyr Leu Ala Ser
1               5                   10                  15

<210> SEQ ID NO 35
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 35

Xaa Xaa Arg Pro Ser Gln Arg Ser Lys Tyr Leu Ala Ser Ala Ser
1               5                   10                  15

<210> SEQ ID NO 36
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
```

```
<222> LOCATION: (15)..(15)
<223> OTHER INFORMATION: amino group

<400> SEQUENCE: 36

Xaa Xaa Phe Gly Ser Asp Arg Gly Ala Pro Lys Arg Gly Ser Gly
1               5                   10                  15

<210> SEQ ID NO 37
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 37

Xaa Xaa Ser Asp Arg Gly Ala Pro Lys Arg Gly Ser Gly Lys Asp
1               5                   10                  15

<210> SEQ ID NO 38
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 38

Xaa Xaa Arg Gly Ala Pro Lys Arg Gly Ser Gly Lys Asp Gly His
1               5                   10                  15

<210> SEQ ID NO 39
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 39
```

Xaa Xaa Ala Pro Lys Arg Gly Ser Gly Lys Asp Gly His His Ala
1               5                   10                  15

<210> SEQ ID NO 40
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 40

Xaa Xaa Lys Arg Gly Ser Gly Lys Asp Gly His His Ala Ala Arg
1               5                   10                  15

<210> SEQ ID NO 41
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 41

Xaa Xaa Gly Ser Gly Lys Asp Gly His His Ala Ala Arg Thr Thr
1               5                   10                  15

<210> SEQ ID NO 42
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 42

Xaa Xaa Pro Pro Ser Gln Gly Lys Gly Arg Gly Leu Ser Leu Ser
1               5                   10                  15

<210> SEQ ID NO 43

```
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 43

Xaa Xaa Ser Gln Gly Lys Gly Arg Gly Leu Ser Leu Ser Arg Phe
1               5                   10                  15

<210> SEQ ID NO 44
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 44

Xaa Xaa Gly Lys Gly Arg Gly Leu Ser Leu Ser Arg Phe Ser Trp
1               5                   10                  15

<210> SEQ ID NO 45
<211> LENGTH: 15
<212> TYPE: PRT
<213> ORGANISM: Unknown
<220> FEATURE:
<223> OTHER INFORMATION: substrate peptide
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 45

Xaa Xaa Gly Gly Arg Ala Ser Asp Tyr Lys Ser Ala His Lys Gly
1               5                   10                  15

<210> SEQ ID NO 46
<211> LENGTH: 15
<212> TYPE: PRT
<213> ORGANISM: Unknown
<220> FEATURE:
<223> OTHER INFORMATION: substrate peptide
```

```
<220> FEATURE:
<221> NAME/KEY: MISC_FEATURE
<222> LOCATION: (1)..(1)
<223> OTHER INFORMATION: Xaa = amino oxyacetic acid
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 46

Xaa Xaa Arg Ala Ser Asp Tyr Lys Ser Ala His Lys Gly Leu Lys
1               5                   10                  15

<210> SEQ ID NO 47
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 47

Cys Xaa Lys Lys Ala Leu Arg Arg Gln Glu Thr Val Asp Ala Leu
1               5                   10                  15

<210> SEQ ID NO 48
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 48

Cys Xaa Lys Lys Ala Leu Arg Arg Gln Glu Ala Val Asp Ala Leu
1               5                   10                  15

<210> SEQ ID NO 49
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (13)..(13)
<223> OTHER INFORMATION: amino group

<400> SEQUENCE: 49

Cys Xaa Ala Lys Arg Arg Arg Leu Ser Ser Leu Arg Ala
1               5                   10
```

```
<210> SEQ ID NO 50
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (13)..(13)
<223> OTHER INFORMATION: amino group

<400> SEQUENCE: 50

Cys Xaa Ala Lys Arg Arg Arg Leu Ala Ala Leu Arg Ala
1               5                   10

<210> SEQ ID NO 51
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 51

Cys Xaa Gly Arg Thr Gly Arg Arg Asn Ser Ile
1               5                   10

<210> SEQ ID NO 52
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 52

Cys Xaa Gly Arg Ala Gly Arg Arg Asn Ala Ile
1               5                   10

<210> SEQ ID NO 53
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group
```

-continued

```
<400> SEQUENCE: 53

Cys Xaa Asp Asp Asp Glu Glu Ser Ile Thr Arg Arg
1               5                   10

<210> SEQ ID NO 54
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 54

Cys Xaa Asp Asp Asp Glu Glu Ala Ile Ala Arg Arg
1               5                   10

<210> SEQ ID NO 55
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 55

Cys Xaa Glu Arg Ser Pro Ser Pro Ser Phe Arg
1               5                   10

<210> SEQ ID NO 56
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 56

Cys Xaa Glu Arg Ala Pro Ala Pro Ala Phe Arg
1               5                   10

<210> SEQ ID NO 57
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
```

```
<221> NAME/KEY: MOD_RES
<222> LOCATION: (13)..(13)
<223> OTHER INFORMATION: amino group

<400> SEQUENCE: 57

Cys Xaa Gly Arg Pro Arg Thr Ser Ser Phe Ala Glu Gly
1               5                   10

<210> SEQ ID NO 58
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (13)..(13)
<223> OTHER INFORMATION: amino group

<400> SEQUENCE: 58

Cys Xaa Gly Arg Pro Arg Ala Ala Ala Phe Ala Glu Gly
1               5                   10

<210> SEQ ID NO 59
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 59

Cys Xaa Lys Lys Lys Ala Leu Ser Arg Gln Leu Ser Val Ala Ala
1               5                   10                  15

<210> SEQ ID NO 60
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 60

Cys Xaa Lys Lys Lys Ala Leu Ala Arg Gln Leu Ala Val Ala Ala
1               5                   10                  15

<210> SEQ ID NO 61
<211> LENGTH: 12
<212> TYPE: PRT
<213> ORGANISM: Unknown
<220> FEATURE:
<223> OTHER INFORMATION: synthesized peptide sequence
<220> FEATURE:
```

```
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 61

Cys Xaa Lys Lys Leu Asn Arg Thr Leu Ser Val Ala
1               5                   10

<210> SEQ ID NO 62
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 62

Cys Xaa Lys Lys Leu Asn Arg Ala Leu Ala Val Ala
1               5                   10

<210> SEQ ID NO 63
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 63

Cys Xaa Lys Arg Gln Gln Ser Phe Asp Leu Phe
1               5                   10

<210> SEQ ID NO 64
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 64

Cys Xaa Lys Arg Gln Gln Ala Phe Asp Leu Phe
1               5                   10

<210> SEQ ID NO 65
<211> LENGTH: 15
<212> TYPE: PRT
```

```
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 65

Cys Xaa Lys Arg Arg Glu Ile Leu Ser Arg Arg Pro Ser Tyr Arg
1               5                   10                  15

<210> SEQ ID NO 66
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 66

Cys Xaa Lys Arg Arg Glu Ile Leu Ala Arg Arg Pro Ala Phe Arg
1               5                   10                  15

<210> SEQ ID NO 67
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 67

Cys Xaa Leu Arg Ala Pro Ser Trp Ile Asp Thr
1               5                   10

<210> SEQ ID NO 68
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 68

Cys Xaa Leu Arg Ala Pro Ala Trp Ile Asp Ala
1               5                   10
```

```
<210> SEQ ID NO 69
<211> LENGTH: 14
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (14)..(14)
<223> OTHER INFORMATION: amino group

<400> SEQUENCE: 69

Cys Xaa Pro Leu Ser Arg Thr Leu Ser Val Ala Ala Lys Lys
1               5                   10

<210> SEQ ID NO 70
<211> LENGTH: 14
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (14)..(14)
<223> OTHER INFORMATION: amino group

<400> SEQUENCE: 70

Cys Xaa Pro Leu Ala Arg Ala Leu Ala Val Ala Ala Lys Lys
1               5                   10

<210> SEQ ID NO 71
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 71

Cys Xaa Pro Leu Ser Arg Thr Leu Ser Val Ser Ser
1               5                   10

<210> SEQ ID NO 72
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 72
```

Cys Xaa Pro Leu Ala Arg Ala Leu Ala Val Ala Ala
1               5                   10

<210> SEQ ID NO 73
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (13)..(13)
<223> OTHER INFORMATION: amino group

<400> SEQUENCE: 73

Cys Xaa Gln Lys Arg Pro Ser Gln Arg Ser Lys Tyr Leu
1               5                   10

<210> SEQ ID NO 74
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (13)..(13)
<223> OTHER INFORMATION: amino group

<400> SEQUENCE: 74

Cys Xaa Gln Lys Arg Pro Ala Gln Arg Ala Lys Phe Leu
1               5                   10

<210> SEQ ID NO 75
<211> LENGTH: 10
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: amino group

<400> SEQUENCE: 75

Cys Xaa Arg Lys Ile Ser Ala Ser Glu Phe
1               5                   10

<210> SEQ ID NO 76
<211> LENGTH: 10
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES

```
<222> LOCATION: (10)..(10)
<223> OTHER INFORMATION: amino group

<400> SEQUENCE: 76

Cys Xaa Arg Lys Ile Ala Ala Ala Glu Phe
1               5                   10

<210> SEQ ID NO 77
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (11)..(11)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 77

Pro Lys Thr Pro Lys Lys Ala Lys Lys Leu Xaa Cys
1               5                   10

<210> SEQ ID NO 78
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (11)..(11)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 78

Pro Lys Ala Pro Lys Lys Ala Lys Lys Leu Xaa Cys
1               5                   10

<210> SEQ ID NO 79
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

<400> SEQUENCE: 79

Cys Xaa Arg Pro Arg Ala Ala Thr Phe
1               5

<210> SEQ ID NO 80
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
```

```
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

<400> SEQUENCE: 80

Cys Xaa Arg Pro Arg Ala Ala Ala Phe
1               5

<210> SEQ ID NO 81
<211> LENGTH: 10
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: amino group

<400> SEQUENCE: 81

Cys Xaa Arg Arg Arg Ala Pro Leu Ser Pro
1               5                   10

<210> SEQ ID NO 82
<211> LENGTH: 10
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (10)..(10)
<223> OTHER INFORMATION: amino group

<400> SEQUENCE: 82

Cys Xaa Arg Arg Arg Ala Pro Leu Ala Pro
1               5                   10

<210> SEQ ID NO 83
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 83

Cys Xaa Arg Arg Arg Glu Glu Glu Thr Glu Glu Glu
1               5                   10

<210> SEQ ID NO 84
<211> LENGTH: 12
<212> TYPE: PRT
<213> ORGANISM: Unknown
```

```
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 84

Cys Xaa Arg Arg Arg Glu Glu Glu Ala Glu Glu Glu
1               5                   10

<210> SEQ ID NO 85
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (13)..(13)
<223> OTHER INFORMATION: amino group

<400> SEQUENCE: 85

Cys Xaa Met His Arg Gln Glu Thr Val Asp Cys Leu Lys
1               5                   10

<210> SEQ ID NO 86
<211> LENGTH: 13
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (13)..(13)
<223> OTHER INFORMATION: amino group

<400> SEQUENCE: 86

Cys Xaa Met His Arg Gln Glu Ala Val Asp Cys Leu Lys
1               5                   10

<210> SEQ ID NO 87
<211> LENGTH: 14
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (14)..(14)
<223> OTHER INFORMATION: amino group

<400> SEQUENCE: 87

Cys Xaa Lys Lys Arg Phe Ser Phe Lys Lys Ser Phe Lys Leu
1               5                   10
```

```
<210> SEQ ID NO 88
<211> LENGTH: 14
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (14)..(14)
<223> OTHER INFORMATION: amino group

<400> SEQUENCE: 88

Cys Xaa Lys Lys Arg Phe Ala Phe Lys Lys Ala Phe Lys Leu
 1               5                  10

<210> SEQ ID NO 89
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 89

Cys Xaa Pro Lys Asp Pro Ser Gln Arg Arg Arg
 1               5                  10

<210> SEQ ID NO 90
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 90

Cys Xaa Pro Lys Asp Pro Ala Gln Arg Arg Arg
 1               5                  10

<210> SEQ ID NO 91
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 91
```

Cys Xaa Ile Ala Ala Asp Ser Glu Ala Glu Gln
1               5                   10

<210> SEQ ID NO 92
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 92

Cys Xaa Ile Ala Ala Asp Ala Glu Ala Glu Gln
1               5                   10

<210> SEQ ID NO 93
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 93

Cys Xaa Ser Pro Ala Leu Thr Gly Asp Glu Ala
1               5                   10

<210> SEQ ID NO 94
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 94

Cys Xaa Ala Pro Ala Leu Ala Gly Asp Glu Ala
1               5                   10

<210> SEQ ID NO 95
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)

<223> OTHER INFORMATION: amino group

<400> SEQUENCE: 95

Cys Xaa Gly Arg Ile Leu Thr Leu Pro Arg Ser
1               5                   10

<210> SEQ ID NO 96
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 96

Cys Xaa Gly Arg Ile Leu Ala Leu Pro Arg Ala
1               5                   10

<210> SEQ ID NO 97
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 97

Cys Xaa Met Gly Glu Ala Ser Gly Cys Gln Leu
1               5                   10

<210> SEQ ID NO 98
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 98

Cys Xaa Met Gly Glu Ala Ala Gly Cys Gln Leu
1               5                   10

<210> SEQ ID NO 99
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)

```
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 99

Cys Xaa Glu Glu Thr Pro Tyr Ser Tyr Pro Thr
 1               5                  10

<210> SEQ ID NO 100
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 100

Cys Xaa Glu Glu Ala Pro Phe Ser Phe Pro Ala
 1               5                  10

<210> SEQ ID NO 101
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 101

Cys Xaa Gly Asn His Thr Tyr Gln Glu Ile Ala
 1               5                  10

<210> SEQ ID NO 102
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 102

Cys Xaa Gly Asn His Ala Phe Gln Glu Ile Ala
 1               5                  10

<210> SEQ ID NO 103
<211> LENGTH: 11
<212> TYPE: PRT
<213> ORGANISM: Unknown
<220> FEATURE:
```

```
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 103

Leu Arg Ser Pro Ser Trp Glu Pro Phe Xaa Cys
1               5                   10

<210> SEQ ID NO 104
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 104

Leu Arg Ala Pro Ala Trp Glu Pro Phe Xaa Cys
1               5                   10

<210> SEQ ID NO 105
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 105

Ser Ser Pro Val Tyr Gln Asp Ala Val Xaa Cys
1               5                   10

<210> SEQ ID NO 106
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 106

Ala Ala Pro Val Phe Gln Asp Ala Val Xaa Cys
1               5                   10

<210> SEQ ID NO 107
```

```
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 107

Cys Xaa Ser Arg Thr Leu Ser Val Ser Ser Leu
1               5                   10

<210> SEQ ID NO 108
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 108

Cys Xaa Ala Arg Ala Leu Ala Val Ala Ala Leu
1               5                   10

<210> SEQ ID NO 109
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 109

Leu Ser Val Ser Ser Leu Pro Gly Leu Xaa Cys
1               5                   10

<210> SEQ ID NO 110
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 110

Leu Ser Val Ala Ala Leu Pro Gly Leu Xaa Cys
```

```
<210> SEQ ID NO 111
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 111

Cys Xaa Val Thr Pro Arg Thr Pro Pro Pro Ser
1               5                   10

<210> SEQ ID NO 112
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 112

Cys Xaa Val Ala Pro Arg Ala Pro Pro Pro Ala
1               5                   10

<210> SEQ ID NO 113
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 113

Cys Xaa Arg Phe Ala Arg Lys Gly Ser Leu Arg Gln Lys Asn Val
1               5                   10                  15

<210> SEQ ID NO 114
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group
```

```
<400> SEQUENCE: 114

Cys Xaa Arg Phe Ala Arg Lys Gly Ala Leu Arg Gln Lys Asn Val
1               5                   10                  15

<210> SEQ ID NO 115
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 115

Cys Xaa Pro Arg Pro Ala Ser Val Pro Pro Ser
1               5                   10

<210> SEQ ID NO 116
<211> LENGTH: 12
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (12)..(12)
<223> OTHER INFORMATION: amino group

<400> SEQUENCE: 116

Cys Xaa Pro Arg Pro Ala Ser Ala Val Pro Pro Ala
1               5                   10

<210> SEQ ID NO 117
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 117

Cys Xaa Arg Glu Ala Arg Ser Arg Ala Ser Thr
1               5                   10

<210> SEQ ID NO 118
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
```

```
<220> FEATURE:
<221> NAME/KEY: MOD_RES
<222> LOCATION: (11)..(11)
<223> OTHER INFORMATION: amino group

<400> SEQUENCE: 118

Cys Xaa Arg Glu Ala Arg Ala Arg Ala Ala Ala
1               5                   10

<210> SEQ ID NO 119
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 119

Gln Ser Tyr Ser Ser Ser Gln Arg Val Xaa Cys
1               5                   10

<210> SEQ ID NO 120
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 120

Gln Ser Tyr Ala Ala Ala Gln Arg Val Xaa Cys
1               5                   10

<210> SEQ ID NO 121
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 121

Cys Xaa Gly Gly Gly Thr Ser Pro Val Phe Pro
1               5                   10

<210> SEQ ID NO 122
<211> LENGTH: 11
<212> TYPE: PRT
<213> ORGANISM: Unknown
<220> FEATURE:
<223> OTHER INFORMATION: synthesized peptide sequence
```

```
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 122

Cys Xaa Gly Gly Gly Ala Ala Pro Val Phe Pro
1               5                   10

<210> SEQ ID NO 123
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 123

Leu Tyr Ser Ser Ser Pro Gly Gly Ala Xaa Cys
1               5                   10

<210> SEQ ID NO 124
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (10)..(10)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 124

Leu Tyr Ala Ala Ala Pro Gly Gly Ala Xaa Cys
1               5                   10

<210> SEQ ID NO 125
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 125

Cys Xaa Asp Leu Pro Leu Ser Pro Ser Ala Phe
1               5                   10

<210> SEQ ID NO 126
<211> LENGTH: 11
```

```
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 126

Cys Xaa Asp Leu Pro Leu Ala Pro Ala Ala Phe
1               5                   10

<210> SEQ ID NO 127
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 127

Cys Xaa Thr Thr Pro Leu Ser Pro Thr Arg Leu
1               5                   10

<210> SEQ ID NO 128
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 128

Cys Xaa Ala Ala Pro Leu Ala Pro Ala Arg Leu
1               5                   10

<210> SEQ ID NO 129
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (14)..(14)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 129

Arg Arg Ile Ser Lys Asp Asn Pro Asp Tyr Gln Gln Asp Xaa Cys
1               5                   10                  15
```

<210> SEQ ID NO 130
<211> LENGTH: 15
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (14)..(14)
<223> OTHER INFORMATION: Xaa = beta-alanine
<220> FEATURE:
<221> NAME/KEY: MOD_RES
<222> LOCATION: (15)..(15)
<223> OTHER INFORMATION: amino group

<400> SEQUENCE: 130

Arg Arg Ile Ala Lys Asp Asn Pro Asp Tyr Gln Gln Asp Xaa Cys
1               5                   10                  15

<210> SEQ ID NO 131
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

<400> SEQUENCE: 131

Cys Xaa Leu Arg Arg Ala Ser Leu Gly
1               5

<210> SEQ ID NO 132
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

<400> SEQUENCE: 132

Cys Xaa Leu Arg Arg Ala Ala Leu Gly
1               5

<210> SEQ ID NO 133
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

```
<400> SEQUENCE: 133

Cys Xaa Leu Arg Arg Ala Ser Leu Gly
1               5

<210> SEQ ID NO 134
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 134

Cys Xaa Gln Lys Arg Pro Ser Gln Arg Ser Lys
1               5                   10

<210> SEQ ID NO 135
<211> LENGTH: 20
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (20)..(20)
<223> OTHER INFORMATION: amino group

<400> SEQUENCE: 135

Cys Xaa Arg Arg Lys Asp Leu His Asp Arg Glu Glu Asp Glu Ala Met
1               5                   10                  15

Ser Ile Thr Ala
            20

<210> SEQ ID NO 136
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

<400> SEQUENCE: 136

Cys Xaa Leu Arg Arg Ala Ala Leu Gly
1               5

<210> SEQ ID NO 137
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
```

```
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 137

Cys Xaa Gln Lys Arg Pro Ala Gln Arg Ala Lys
1               5                   10

<210> SEQ ID NO 138
<211> LENGTH: 20
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (20)..(20)
<223> OTHER INFORMATION: amino group

<400> SEQUENCE: 138

Cys Xaa Arg Arg Lys Asp Leu His Asp Asp Glu Glu Asp Glu Ala Met
1               5                   10                  15

Ala Ile Ala Ala
            20

<210> SEQ ID NO 139
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

<400> SEQUENCE: 139

Cys Xaa Leu Arg Arg Ala Ser Leu Gly
1               5

<210> SEQ ID NO 140
<211> LENGTH: 9
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (9)..(9)
<223> OTHER INFORMATION: amino group

<400> SEQUENCE: 140

Cys Xaa Leu Arg Arg Ala Ala Leu Gly
1               5

<210> SEQ ID NO 141
```

```
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 141

Cys Xaa Gln Lys Arg Pro Ser Gln Arg Ser Lys
1               5                   10

<210> SEQ ID NO 142
<211> LENGTH: 11
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (11)..(11)
<223> OTHER INFORMATION: amino group

<400> SEQUENCE: 142

Cys Xaa Gln Lys Arg Pro Ala Gln Arg Ala Lys
1               5                   10

<210> SEQ ID NO 143
<211> LENGTH: 20
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
<221> NAME/KEY: MOD_RES
<222> LOCATION: (20)..(20)
<223> OTHER INFORMATION: amino group

<400> SEQUENCE: 143

Cys Xaa Arg Arg Lys Asp Leu His Asp Asp Glu Glu Asp Glu Ala Met
1               5                   10                  15

Ser Ile Thr Ala
            20

<210> SEQ ID NO 144
<211> LENGTH: 20
<212> TYPE: PRT
<213> ORGANISM: Unknown
<220> FEATURE:
<223> OTHER INFORMATION: synthesized peptide sequence
<220> FEATURE:
<221> NAME/KEY: MISC_FEATURE
<222> LOCATION: (2)..(2)
<223> OTHER INFORMATION: Xaa = beta-alanine
<220> FEATURE:
```

-continued

```
<221> NAME/KEY: MOD_RES
<222> LOCATION: (20)..(20)
<223> OTHER INFORMATION: amino group

<400> SEQUENCE: 144

Cys Xaa Arg Arg Lys Asp Leu His Asp Asp Glu Glu Asp Glu Ala Met
1               5                   10                  15

Ala Ile Ala Ala
            20
```

METHOD FOR DETERMINING THE SUBSTRATE SPECIFICITY OF AN ENZYME

This application is a continuation application of U.S. application Ser. No. 10/475,104, filed Feb. 10, 2004, abandoned, which is a 371 of PCT/EP02/04265 filed on Apr. 17, 2002, which claims priority from DE 101 18 744.2, filed on Apr. 17, 2001, the disclosures of which are hereby incorporated by reference.

The present invention relates to assemblies of a plurality of amino acid sequences on a surface, supports and support assemblies comprising these, a method for producing such an assembly, a method for determining the substrate specificity of an enzymatic activity, use of the method for determining the pattern of the enzymatic activity of a sample.

With the increasing availability of sequence information from the various genome projects, the assembly of nucleic acid fragments having a high density on a support material, so-called chips or biochips, has acquired major importance whose full potential, however, has only been able to be utilised with the availability of newer synthesis techniques and miniaturisation, and has resulted in a plurality of applications. In addition to nuclei acids, natural substances or libraries thereof but also assemblies of oligopeptides and proteins have been applied to such chips. Cellulose, glass, nitrocellulose, PFTE membranes and special agar have been used as support materials for these assemblies.

With the increasing importance of proteomics and its biotechnological application, peptides and proteins have become the focus of interest. In general, it is proteins and mostly their enzymatic activities which make possible almost all biochemical reactions inside and outside the cell. The use of assemblies of nucleic acids with which either the messenger RNA (mRNA), which was generated by the genes specifically active in the cell, or DNA copies of this mRNA are detected, is certainly of major importance but the information obtainable therewith is for many reasons not sufficient for understanding the processes involved in both intracellular and extracellular processes and for use to be made thereof in various biotechnological applications. One reason for this is that the quantity of mRNA in a cell frequently does not correlate with the corresponding amount of protein produced in the cell. In addition, proteins once produced can be considerably influenced in their enzymatic activity (and thus in their biological function) by slight chemical modifications in the cell (post-translational modifications). There is thus a need to carry out a parallel analysis of the enzymatic activity of as many proteins as possible, especially enzymes. Such an approach allows, among other things, the substrate specificity of a defined enzyme to be determined rapidly which is again an important requirement for the design of knowledge-based inhibitors, or for the selective testing of pharmaceuticals or pharmaceutical candidates, especially as part of the prediction of side effects.

In the prior art assemblies of peptides or proteins were immobilised on various surfaces such as glass (J. Robles, M. Beltran, V. Marchan Y. Perez, I. Travesset, E. Pedroso, A. Grandas; 1999, Towards nucleotides containing any trifunctional amino acid, Tetrahedron, 55, 13251-13264), cellulose (D. R. Englebretsen, D. R. K. Harding; 1994, High yield, directed immobilization of a peptide-ligand onto a beaded cellulose support, Pept. Res. 7, 322-326), nitrocellulose (S. J. Hawthorne, M. Pagano, P. Harriott, D. W. Halton, B. Walker; 1998, The synthesis and utilisation of 2,4-dinitrophenyl-labeled irreversible peptidyl diazomethyl ketone inhibitors, Anal. Biochem., 261, 131-138), PTFE membranes (T. G. Vargo, E. J. Bekos, Y. S. Kim, J. P. Ranieri, R. Bellamkonda, P. Aebischer, D. E. Margevich, P. M. Thompson, F. V. Bright, J. A. Gardella; 1995, Synthesis and characterization of fluoropolymeric substrata with immobilized minimal peptide sequences for cell adhesion studies. 1., J. Biomed. Mat. Res. 29, 767-778), titanium oxide (S. J. Xiao, M. Textor, N. D. Spencer, M. Wieland, B. Keller, H. Sigrist; 1997, Immobilization of the cell-adhesive peptide ARG-GLY-ASP-CYS (RGDC) on titanium surfaces by covalent chemical attachment, J. Materials Science-Materials in Medicine, 8, 867-872), silicon oxide (T. Koyano, M. Saito, Y. Miyamoto, K. Kaifu, M. Kato; 1996, Development of a technique for microimmobilization of proteins on silicon wafers by a streptavidin-biotin reaction, Biotech. Progress., 12, 141-144) or gold (B. T. Houseman, M. Meksich; 1998, Efficient solid-phase synthesis of peptide-substituted alkanethiols for the preparation of substrates that support the adhesion of cells, J. Org. Chem. 63, 7552-7555) or the stepwise synthesis of peptides was carried out directly on a corresponding glass surface (S. P. A. Fodor, J. L. Read, M. C. Pirrung, L. Stryer, A. T. Lu, D. Solas; 1991, Light-directed, spatially addressable parallel chemical synthesis, Science, 251, J. P. Pellois, W. Wang, X. L. Gao; 2000, Peptide synthesis based on t-Boc chemistry and solution photogenerated acids, J. Comb. Chem. 2, 355-360) or on cellulose (R. Frank, 1992, Spot synthesis: an easy technique for the positionally addressable, parallel chemical synthesis on a membrane support, Tetrahedron, 48, 9217-9232; A Kramer and J. Schneider-Mergener, Methods in Molecular Biology, vol 87: Combinatorial Peptide Library Protocols, p. 25-39, edited by: S. Cabilly; Humana Press Inc., Totowa, N.J.; Töpert, F., Oires, C., Landgraf, C., Oschkinat, H. and Schneider-Mergener, J., 2001, Synthesis of an array comprising 837 variants of the hYAP WW protein domain, Angew. Chem. Int. Ed., 40, 897-900) or on polypropylene (M. Stankova, S. Wade, K. S. Lam, M. Lebl; 1994, Synthesis of combinatorial libraries with only one representation of each structure, Pept. Res. 7, 292-298, F. Rasoul, F. Ercole, Y. Pham, C. T. Bui, Z. M. Wu, S. N. James, R. W. Trainor, G. Wickham, N. J. Maeji; 2000, Grafted supports in solid-phase synthesis, Biopolymers, 55, 207-216, H. Wenschuh, R. Volkmer-Engert, M. Schmidt, M. Schulz, J. Schneider-Mergener, U. Reineke; 2000, Coherent membrane supports for parallel microsynthesis and screening of bioactive peptides, Biopolymers, 55, 188-206) or on chitin (W. Neugebauer, R. E. Williams, J. R. Barbier, R. Brzezinski, G. Willick; 1996, Peptide synthesis on chitin, int. J. Pept. Prot. Res. 47, 269-275) or on Sepharose (W. Tegge, R. Frank, 1997, Peptide synthesis on Sepharose beads, J. Peptides Res., 49, 355-362, R. Gast, J. Glokler, M. Hoxter, M. Kiess, R. Frank, W. Tegge; 1999. Method for determining protein kinase substrate specificities by the phosphorylation of peptide libraries on beads, phosphate-specific staining, automated sorting, and sequencing, Anal. Biochem., 276, 227-241).

The object of the present invention is thus to provide a means for testing substrate specificities of enzymatic activities which on the one hand is suitable for use in a system with high throughput and on the other hand, can be carried out with extremely small quantities of enzymatic activity or sample volume. It is especially an object that the means has an improved signal-to-noise ratio compared with the means according to the prior art, especially the peptide and protein assemblies described therein and there described as "arrays".

Another object of the present invention is to provide a method for producing such means and a method for determining the substrate specificity of an enzymatic activity and a method for determining the selectivity of an active substance.

This object is solved according to the invention by a method for determining the substrate specificity of an enzymatic activity comprising the following steps:

- Preparation of an assembly comprising a plurality of amino acid sequences on a planar surface of a support material wherein the amino acid sequences are directionally immobilised,
- Contacting and/or incubating of an enzymatic activity with the assembly, and
- Detection of a reaction between one of the amino acid sequences immobilised on the assembly and the enzymatic activity, wherein it is provided that during the reaction of the enzymatic activity with the assembly, a change in the molecular weight of at least one of the amino acid sequences takes place.

In one embodiment it is provided that the reaction is detected on or using the amino acid sequence immobilised on the surface of the support material.

In another embodiment it is provided that the change in the molecular weight takes place by formation or cleaving of a covalent bond on one of the amino acid sequences, preferably on that amino acid sequence which reacts with the enzymatic activity.

In yet another embodiment it is provided that the reaction is detected by detecting the change in the molecular weight.

Finally in one embodiment it is provided that the reaction is detected by a detection method selected from the group comprising autoradiography, plasmon resonance spectroscopy and fluorescence spectroscopy.

In one embodiment it is provided that at least one of the amino acid sequences is a substrate for an enzymatic activity.

In another embodiment it is provided that the assembly of amino acid sequences for at least two different enzymatic activities has at least one substrate each.

In a preferred embodiment it is provided that the enzymatic activity is selected from the group comprising kinases, sulphotransferases, glycosyl transferases, acetyl transferases, farnesyl transferases, palmytyl transferases, phosphatases, sulphatases, esterases, lipases, acetylases and proteases.

In another embodiment it is provided that the detection of a reaction between the amino acid sequences immobilised on the assembly and the enzymatic activity is repeated many times, preferably after intervals of time.

In yet another embodiment it is provided that the enzymatic activity is determined in a sample and the sample is preferably selected from the group comprising urine, liquor, sputum, stool, lymph fluid, cell lysates, tissue lysates, organ lysates, extracts, raw extracts, purified preparations and unpurified preparations.

In one embodiment it is provided that the surface is a non-porous surface.

In another embodiment it is provided that the support material is glass.

In yet another embodiment it is provided that the amino acid sequence is immobilised via a sulphur-comprising group on the surface.

In a second aspect the object is solved by an assembly of a plurality of amino acid sequences on a surface, preferably on the surface of a solid-phase support, wherein the amino acid sequences are directionally immobilised on the planar surface of a support material, wherein at least one of the amino acid sequences is a substrate for an enzymatic activity, wherein a change in the molecular weight takes place on the substrate as a result of the enzymatic activity.

In one embodiment it is provided that the change in the molecular weight takes place as a result of the formation or cleavage of a covalent bond on the substrate.

In another embodiment it is provided that the assembly of amino acid sequences for at least two different enzymatic activities has at least one substrate each.

In yet another embodiment it is provided that the planar surface is a non-porous surface.

In one embodiment it is provided that the support material is selected from the group comprising silicates, ceramic, glass, metals and organic support materials.

In another embodiment it is provided that the amino acid sequences are selected from the group comprising peptides, oligopeptides, polypeptides and proteins as well as their respective derivatives.

In yet another embodiment it is provided that each amino acid sequence or group of amino acid sequences has a defined arrangement relative to another amino acid sequence or groups of amino acid sequences.

In another aspect the object according to the invention is solved by a support comprising an assembly according to the invention.

In one embodiment it is provided that the support comprises a base support material.

In another embodiment it is provided that the assembly of a plurality of amino acid sequences is arranged on one or a plurality of surfaces of the support.

In another aspect the object is solved by a support assembly comprising at least two supports according to the invention, wherein respectively two supports are separated by a gap.

In one embodiment it is provided that at least one assembly on a first support is facing at least one assembly on a second support.

In another embodiment it is provided that the gap has a width of around 0.01 mm to 10 mm, preferably around 0.1 mm to 2 mm, and more preferably around 0.5 mm to 1 mm.

In yet another aspect the object is solved according to the invention by the use of an assembly according to the invention and/or a support according to the invention and/or a support assembly according to the invention in a method according to the invention.

The present invention is based on the surprising finding (see FIG. 12A) that with an assembly of a plurality of amino acid sequences (see FIG. 12A, $B_1$-$B_3$) on a surface, wherein it is especially provided that the amino acid sequences are directionally immobilised on the surface and the surface is a planar surface, on bringing the assembly into contact with a sample containing a potential interaction partner (FIG. 12A, C) for one or a plurality of amino acid sequences contained in the assembly, very small quantities of the potential interaction partner, expressed as international units/liquid volumes, can suffice to detect a binding event between one or a plurality of the amino acid sequences and the potential interaction partner.

The potential interaction partner is preferably an enzymatic activity and the binding event is the formation of the complex of enzymatically active protein and—potential—substrate required for a catalytic reaction. In other words, the assembly according to the invention allows the signal-to-noise ratio to be improved by several orders of magnitude compared with the assemblies according to the prior art, which is based on the special combination of the features of the directional immobilisation and the presence of a planar surface.

When porous surfaces are used, as is the case for example, when using cellulose or porous glass, a large quantity of material, in the present case of amino acid sequences per unit area, can be immobilised, which results in good signal intensities and large regions with a proportional measurement signal, but at the same time the availability of the large surface causes a non-specific interaction of the amino acid sequences with the support material which leads to higher background signals. Furthermore, such porous surfaces require substantially more material to develop the assembly or for coating a support material carrying the assembly, i.e., larger quantities of each of the various amino acid sequences. Likewise as a result of the porous surface, more sample material is required for the actual analysis process. The sample material comprises such material that contains a possible interaction partner for one or a plurality of amino acid sequences. However, this increase in sample material cannot be compensated in every case by providing a larger sample volume, but rather it may be necessary to increase the specific quantity of the potential interaction partner in the sample which comes in contact or should come in contact with the assembly.

This would necessitate purifying the sample material to be analysed wherein however quite appreciable losses frequently occur during such purification, so that the use of porous surfaces for assemblies of molecules on surfaces is not suitable for detecting interaction partners whose concentration in a sample is comparatively low. If the potential interaction partner comprises an enzymatic activity (which herein generally includes enzymes and any catalytically active molecules, for example, also catalytically active nucleic acids), under the influence of the purification or concentration of the sample material or the interaction partner, i.e., the specific enzymatic activity, required when using assemblies according to the prior art, the situation may arise that certain enzymatic activities cannot be determined. This imposes a considerable limitation on the use of assemblies comprising amino acid sequences insofar as it is frequently those enzymatic activities which are not necessarily the predominant quantity in a sample, that are of central biological importance. Thus, with the assembly according to the invention for example, macerated cells can be analysed without further treatment in the sense of purification and enzymatic interaction partners contained therein can be detected with a low specific activity.

A further disadvantage of using porous surfaces is that capillary forces unavoidably act there, preventing any miniaturisation as is especially required for high-throughput systems. In other words, when porous support systems are used, only a certain density of amino acid sequences can be achieved in an assembly. Currently, as a result of the physicochemical properties forming the basis of the porosity, this limit in the case of cellulose is 100/cm$^2$.

On the other hand, however, the use of planar surfaces alone is again not suitable for preparing an assembly to move forward into the range of signal intensities attainable with the assembly according to the invention, especially the signal-to-noise ratios, since the loading capacity is frequently the limiting factor here. Attempts to avoid these limitations by applying polyacrylamide gels having a defined pore width to the planar, non-porous surface did not result in the desired success since the said disadvantages of the porous membranes were subsequently reintroduced again here.

With the present invention a method is adopted for the construction of assemblies of a plurality of amino acid sequences on a surface, which not only concentrates on the surface aspect but also on the specific type of immobilisation of the amino acid sequences contained on the assembly, and thus accounts for their surprising performance. The planar surface merely requires a comparatively small quantity of different amino acid sequences which in addition, as a result of their directional immobilisation on the surface, present optimal interaction partners, especially substrates for enzymatic activities so that despite the comparatively low loading capacity as a result of the smooth, i.e., preferably non-porous surface, significant signals are nevertheless achieved and likewise as a result of the planar surface, no non-specific absorption occurs and therefore no deterioration in the signal-to-noise ratio. As is shown by means of the model calculation given in the examples, as a result of the combination of these two features of the assembly according to the invention, the signal-to-noise ratio is improved by a factor of 3000, as can be seen from FIGS. 3 and 4.

In the assembly according to the invention of a plurality of amino acid sequences on a surface, the surface functions to a certain extent as a substrate on which the plurality of amino acid sequences is immobilised. The immobilisation can take place such that it is accomplished covalently. In addition to covalent immobilisation, however, other forms of immobilisation are also possible, especially adsorptive immobilisation or immobilisation via specific interaction systems. Especially preferred for the immobilisation is covalent immobilisation wherein a chemoselective binding of the amino acid sequences to the surface of the support material takes place. A number of reactions known as such to the person skilled in the art can be used here (Lemieux, G. A. & Bertozzi, C. R., 1998, Chemoselective ligation reactions with proteins, oligosaccharides and cells, *TIBTECH,* 16, 506-513, see FIG. 11 for this). With a view to the required directional immobilisation it should basically be ensured that under the respective interaction conditions, substantially only one special compound is formed between the amino acid sequence and the surface (FIG. 12, Linker A). The choice of the reactive group on the amino acid sequence side will thus depend substantially on the individual sequence. Alternatively it is provided within the scope of the present invention that a terminal structure standard to all the amino acid sequences is provided and this terminal structure is made available for the specific reaction with the surface, especially an activated surface (FIG. 12, Linker A). Typically during the chemoselective reactions amino or carboxyl groups contained in the amino acid sequence are not adversely affected. Examples of suitable reactions are the formation of thioethers from halo-carbonic acids and thiols, which include the formation of thioethers from halocarbonic acids and thiols, thioethers from thiols and maleinimides, amide bonds from thioesters and 1,2-aminothiols, thioamide bonds from dithioesters and 1,2-aminothiols, thiazolidines from aldehydes and 1,2-aminothiols, oxazolidines from aldehydes/ketones and 1,2-amino alcohols, imidazoles from aldehydes/ketones and 1,2-diamines (see also FIG. 11), thiazols from thioamides and alpha-haloketones, aminothiazols from amino-oxy-compounds and alpha-isothiocyanato-ketones, oximes from amino-oxy-compounds and aldehydes, oximes from amino-oxy-compounds and ketones, hydrazones from hydrazines and aldehydes, hydrazones from hydrazides and ketones. Moreover, the radicals R1-R5 shown in FIG. 11 or the residues in the above-mentioned chemoselective reactions can be alkyl, alkenyl, alkynyl, cycloalkyl or aryl radicals or heterocyclic compounds, wherein alkyl stands for branched and unbranched $C_{1-20}$-alkyl, $C_{3-20}$-cycloalkyl, preferably for branched and unbranched-$C_{1-12}$ alkyl, $C_{3-12}$-cycloalkyl, and especially preferably for branched and unbranched $C_{1-6}$-alkyl, $C_{3-6}$-cycloalkyl radicals. Alkenyl stands for branched and unbranched $C_{2-20}$-alkenyl, branched and unbranched $C_{1-20}$-alkyl-O—$C_{2-20}$ alkenyl, $C_{1-20}(-O/S-C_{2-20})_{2-20}$ alkenyl, aryl-$C_{2-20}$-alkenyl, branched and unbranched heterocyclyl $C_{2-20}$ alkenyl, $C_{3-20}$-cycloalkenyl, preferably for branched and unbranched $C_{2-12}$-alkenyl, branched and unbranched $C_{1-12}(-O/S-C_{2-12})_{2-12}$ alkenyl, especially preferably for branched and unbranched $C_{2-6}$-alkenyl, branched and unbranched $C_{1-6}(-O/S-C_{2-8})_{2-8}$ alkenyl radicals; alkynyl stands for branched and unbranched $C_{2-20}$-alkynyl, branched and unbranched $C_{1-20}(-O/S-C_{2-20})_{2-20}$ alkynyl, preferably for branched and unbranched $C_{2-12}$-alkynyl, branched and unbranched $C_{1-12}(-O/S-C_{2-12})_{2-12}$ alkynyl, especially preferably for branched and unbranched $C_{2-6}$-alkynyl, branched and unbranched $C_{1-6}(-O/S-C_{2-8})_{2-8}$ alkynyl radicals; cycloalkyl stands for bridged and unbridged $C_{3-40}$-cycloalkyl, preferably for bridged and unbridged $C_{3-26}$-cycloalkyl, especially preferably for bridged and unbridged $C_{3-15}$-cycloalkyl radicals; aryl stands for substituted and unsubstituted mono- or multi-linked phenyl, pentalenyl, azulenyl, anthracenyl, indacenyl, acenaphtyl, fluorenyl, phenalenyl, phenanthrenyl, preferably for substituted and unsubstituted mono- or multi-linked phenyl, pentalenyl, azulenyl, anthracenyl, indenyl, indacenyl, acenaphtyl, fluorenyl, especially preferably for substituted and unsubstituted mono- or multi-linked phenyl, pentalenyl, anthracenyl radicals as well as their partly hydrated derivatives. Heterocyclic compounds can be unsaturated and saturated 3-15-membered mono-, bi- and tricyclic rings with 1-7 heteroatoms, preferably 3-10-membered mono-, bi- and tricyclic rings with 1-5 heteroatoms and especially preferably 5-, 6- and 10-membered mono-, bi- and tricyclic rings with 1-3 heteroatoms.

In addition, at the alkyl, alkenyl, alkynyl, cycloalkyl, aryl, heteroatoms, heterocyclic compounds, biomolecules or natural substance, 0 to 30 (preferably 0 to 10, especially preferably 0 to 5) of the following substituents can occur singly or in combination with one another: fluorine, chlorine, bromine, iodine, hydroxyl, amide, ester, acid, amine, acetal, ketal, thiol, ether, phosphate, sulphate, sulphoxide, peroxide, sulphonic acid, thioether, nitrile, urea, carbamate, wherein the following are preferred: fluorine, chlorine, bromine, hydroxyl, amide, ester, acid, amine, ether, phosphate, sulphate, sulphoxide, thioether, nitrile, urea, carbamate and especially preferred are: chlorine, hydroxyl, amide, ester, acid, ether, nitrile.

By directional immobilisation it should herein especially be understood that every amino acid sequence is bound to the surface via a defined reactive group or collection of reactive groups. As a result of this binding specificity it is achieved that within the limits of the usual entropies the individual amino acid sequences are in an energetically preferred state so that the amino acid sequences immobilised to such an extent are in broadly similar secondary and tertiary structures.

By the concept "assembly of a plurality of amino acid sequences" it is herein especially understood that each amino acid sequence is immobilised at a specific location on the surface. Preferably each of these locations can be identified. The locations are thus distinct locations at which respectively one species of amino acid sequence is substantially immobilised. In other words, there exists a map from which the position of each of the immobilised amino acid sequences on the surfaces can be derived. The individual amino acid sequence can represent a plurality of molecules which are however substantially identical in respect of their amino acid sequence, i.e. the type and sequence of the amino acids forming them. The identity of the amino acid sequence is substantially determined by the method of producing the amino acid sequences. It is within the scope of the present invention that the amino acid sequences are synthesised in situ on the surface of the assembly, wherein all possible forms are feasible here, i.e., sequential attachment of the individual amino acids forming the amino acid sequence in the same way as the use of block synthesis techniques in which groups of amino acids are added together and the individual blocks are then strung together sequentially and the blocks or sequences thereof are then immobilised or attached to already immobilised amino acid sequences.

It is understandable to the person skilled in the art that as a result of the not always complete yields of the individual synthesis steps or coupling steps, certain heterogeneities can arise in the various amino acid sequences in the sense described previously. This can especially be a problem for syntheses requiring many reaction steps, as is the case with the synthesis of amino acid sequences (per amino acid building block, one coupling reaction and one protective group cleaving and, at the end of the synthesis generally, one reaction for the simultaneous cleaving of all protective groups of the side chain functions). Thus, for example, during the synthesis of one amino acid sequence consisting of 20 amino acid building blocks or 40 amino acid building blocks, and an assumed average yield of 95 % for the necessary 41 or 81 reaction steps, the predicted theoretical yield is only $0.95^{41}=0.122$ (12.2%) or $0.95^{81}=0.0157$ (1.57%). Even for an assumed average yield of 99% only 66.2% or 44.3% are obtained for the examples cited above. It thus becomes clear that during the enzymatic reactions to be studied, as a result of these limitations in addition to the desired amino acid sequence there are a large number of other amino acid sequences which are distinguished by the absence of one or a plurality of amino acid building blocks. Precisely these by-products, known to the person skilled in the art as error or Rumpf sequences, can under certain circumstances seriously distort the result of the incubation with an enzymatic activity modifying the amino acid sequences arranged on the surface or make it difficult to interpret the results. For example, during the immobilisation of a substrate for a kinase on or at a surface using the amino groups contained within this substrate, there are a plurality (depending on the number of amino groups present in the compound to be immobilised) of possibilities for the reaction and thus for the final orientation of the compound on the surface. If just one or a plurality of these amino groups is required for the effective formation of an enzyme/substrate/complex during the subsequent incubation of this immobilised compound (kinase substrate) with a biological fluid containing at least one kinase activity, such a non-specific immobilisation can have the result that only a small population of the immobilised substrate is anchored in the correct fashion and thus the measurement signal is below the detection limit. Thus, a specific or directional immobilisation is a great advantage. In this case, in an immobilisation event the contact between the compound to be immobilised and the surface on or at which the compound is immobilised takes place in the same fashion in each case and all compounds are bound on or to the surface in a defined and predictable orientation.

The plurality of amino acid sequences consists of at least two different amino acid sequences. It can be provided that the amino acid sequence immobilised at a distinct site reoccurs at another site on the surface. This can be achieved for example for control purposes.

The planar surface can be such a surface that is aligned substantially two-dimensionally. Especially it is not provided according to the present invention that the surface carrying a plurality of amino acid sequences is a spherical surface or a substantial part of such a surface. During the development of the planar surface it is preferred that the distinct locations at which respectively one amino acid sequence is localised are not or at least are not substantially separated by a three-dimensional structure from another distinct location on the surface.

All biotolerable, functionalised or functionalisable materials can be used as materials for the surface or as support materials which can carry the assemblies according to the invention within the scope of the present invention. These materials can, for example, be present as solid support plates (monolithic blocks), membranes, films or laminates. Suitable materials are polyolefins, such as, for example, polyethylene, polypropylene, halogenated polyolefins (PVDF, PVC etc,) as well as polytetrafluoroethylene. On the inorganic materials side, for example, ceramic, silicates, silicon and glass can be used. Although non-metallic support plates are preferred, it is however also within the scope of the present invention to use metallic support materials despite their tendency to form potentially non-specific adsorption effects. Examples of such materials are gold or metal oxides, such as titanium oxide for example.

Regardless of the material actually selected, wherein glass is particularly preferred, it is also essential for the present invention that the surface is of a non-porous nature and capillary forces do not occur or do not substantially occur at the surface.

During the development of the assembly, there are a number of possibilities for the design of the surface in the actual sense, i.e. the planar surface carrying the plurality of amino acid sequences. It is fundamentally possible that the surface on which the directional immobilisation of the amino acid sequences takes place is at the same time the support material. However, it is also possible that the reactive surface differs from the support material. Such a scenario is provided, for example, if the material forming the (planar) surface is present in the form of a film, which is then applied to a further base support material, not least for stabilisation purposes.

For purposes of directional immobilisation, especially if this takes place by covalent bonding of the amino acid sequences on a support material, the surface of the support plate can be functionalised. A plurality of successive functionalisations is fundamentally possible but, depending on the support material selected, a functionalisation can also be omitted.

A first functionalisation which is already suitable to accomplish a covalent bonding of the amino acid sequences to the surface can be accomplished in the provision of amino and/or carboxyl groups as reactive groups. Such a functionalisation, regardless of the chemical nature of the reactive groups applied, is also designated herein as first functionalisation. Carboxyl groups can be produced by oxidation with chromic acid, for example, starting from polyolefins as the material providing the surface. Alternatively this can also be accomplished, for example, by high-pressure reaction with oxalyl chloride as well as plasma oxidation, radical or light-induced addition of acrylic acid or the like. As a result of base-catalysed elimination processes which lead to double bonds at the surface, halogenated materials such as halogenated polyolefins can result in the production of both amino- and carboxy-reactive groups, whereby the reactive double bonds are then carboxy- or amino-functionalised.

Ceramics, glasses, silicon oxide and titanium oxide can be simply functionalised using substituted silanes available commercially in a plurality such as, for example, aminopropyl triethoxy silane. Support plates with hydroxyl groups on the surface can be modified by a plurality of reactions. Reactions with biselectrophiles are especially advantageous, such as for example, the direct carboxymethylation with bromacetic acid; acylation with a corresponding amino acid derivative such as, for example, dimethylaminopyridine-catalysed carbodiimide coupling with fluorenyl methoxycarbonyl-3-aminopropionic acid or the generation of iso(thio-)cyanates by mono-conversion with corresponding bis-iso(thio)cyanates. An especially advantageous method is the reaction with carbonyl diimidazole or phosgene or triphosgene or p-nitrophenyl chloroformiate or thiocarbonyl diimidazole followed by the reaction with diamine or simply protected diamines in order to apply amino functions to the support materials via a stable urethane bond on the surface.

According to the present invention, it can be provided that the amino acid sequences immobilised on the surface have a spacer. Such spacers are especially preferred when the amino acid sequences are the substrate for enzymatic activities which should occupy a specific spatial structure in order to be thereby accessible for the enzymatic activity. As a result of using such spacers, herein also designated as "spacer", the amino acid sequences which should be the actual substrates for said enzymatic activity or activities, gain additional degrees of freedom and surface phenomena such as adsorption, change in the thermodynamic degrees of freedom etc., will occur. A spacer can substantially be any biocompatible molecule that contains at least two functional or functionalisable groups. The spacer is inserted in the used state as an element between the surface and the amino acid sequence.

The following classes of compounds are suitable as spacers:

Alkanes, branched or unbranched, especially those having a chain length of C2 to C30, especially C4 to C8;

Polyethers, i.e., polymers of polyethylene oxide or polypropylene oxide, wherein the polyethers preferably consist of 1 to 5 polyethylene oxide units or polypropylene oxide units.

Polyalcohols, branched or unbranched such as polyglycol and derivatives thereof, such as for example O,O'-bis(2-aminopropyl)-polyethylene glycol 500 and 2,2'-(ethylene dioxide)-diethyl amine.

Polyurethane, polyhydroxy acids, polycarbonates, polyimide, polyamide, polyester, polysulphones, especially those comprising 1-100 monomer units, quite especially preferably consisting of 1-10 monomer units.

Combinations of the aforesaid alkanes with the aforesaid polyethers; polyurethanes, polyhydroxy acid, polycarbonates, polyimides, polyamides, polyamino acids, polyesters and polysulphones Diamino alkanes, branched or unbranched, preferably those having a chain length of C2 to C30, quite especially preferably those having a chain length of C2 to C8; as examples mention may be made of 1,3-diamino propane, 1,6-diamino hexane and 1,8-diamino octane, as well as their combinations with polyethers, preferably with the aforesaid polyethers; such as for example 1,4-bis-(3-aminopropoxy)butane.

Dicarbonic acids and their derivatives, such as for example, hydroxy-, mercapto, and amino dicarbonic acids, saturated or unsaturated, branched or unbranched, especially C2 to C30 dicarbonic acids, preferably those having a chain length of C2 to C10, quite especially preferably those having a chain length of C2 to C6; such as for example, succinic acid and glutaric acid; and Amino acids and peptides, preferably having a length of 1-20 amino acid residues, quite especially preferably having a length of 1-3 amino acid residues, for example, trimers of lysine, dimers of 3-amino propionic acid and monomers of 6-amino capronic acid.

As a result of the fact that the spacer has two functional ends, it is fundamentally possible to select the functionality so that the amino acids to be immobilised on the surface are either immobilised via their C-terminus or their N-terminus or via another functional grouping within the amino acid sequence to be immobilised. If an immobilisation is to take place via the C-terminus, the functional group of the spacer acting on the C-terminus is preferably an amino group. If the amino acid sequences are to be immobilised by means of the N-terminus to the surface, the corresponding functional group of the spacer is a carboxyl group.

In the assembly according to the invention, it can be provided that the spacer is a branched spacer. Such branched spacers are also called dendrimer structures or dendrimers for short and are known to the person skilled in the art. Dendrimer structures for the immobilisation of nucleic acids are described, for example, in Beier, M. & Hoheisel, J. D., 1999, Versatile derivatisation of solid support media for covalent bonding on DNA microchips, 9, 1970-1977. The function of these dendrimer structures consists in increasing the number of reactive groups per unit area and thus the signal intensity. Dendrimer structures can be provided with almost all functional or functionalisable groups which then allow immobilisation of the amino acid sequences. As a result of using such dendrimer structures, the number of reactive groups per unit area of the planar surface can then be increased by a factor of 2 to 100, preferably by a factor of 2 to 20 and more preferably by a factor of 2 to 10.

The construction of a dendrimer structure can be accomplished, for example, in the case where the surface is provided with an amino functionality by a reaction sequence comprising an acylation with acrylic acid or acrylic acid derivatives such as acrylic acid chloride or alpha-bromo carbonic acids or alpha-bromo carbonic acid derivatives such as bromacetyl bromide, Michael addition of suitable polyamines such as, for example, tetraethylene pentamine, then further acylation with acrylic acid or acrylic acid derivatives such as acrylic acid chloride or alpha-bromo carbonic acids or alpha-bromo carbonic acid derivatives such as bromacetyl bromide and further Michael addition of suitable polyamines. The polyamines are preferably selected such that they are hydrophilic themselves in order to increase the hydrophilic property of the surface. An example of such a polyamine is 1,4-bis-(3-aminopropoxy)butane.

In addition to the first functionalisation of the surface, a second functionalisation can take place, which builds on the first functionalisation. In other words, the reactive group of the surface is extensively functionalised by additional measures. The second functionalisation can take place directly on the functionalised surface, on the surface provided with a spacer or on a dendrimer structure.

A reason for the second functionalisation can be seen in that, as a result of the amino and carboxyl groups present in the amino acid sequences, thiol functions, imidazole functions and guanido functions, no uniform immobilisation relative to the orientation of the amino acid sequence on the surface can be achieved. A second functionalisation provides access to further chemoselective reactions in order to achieve directional immobilisation.

All those compounds distinguished by a presence of non-proteinogenic functional groups are suitable for this second functionalisation. For example, the following compounds may be mentioned: maleinimido compounds such as maleinimido amine or maleinimido carbonic acids; alpha-halo-ketones such as bromo-pyroracemic acid or 4-carboxy-alpha-bromo-acetophenone, alpha-isothiocyanato-ketones such as 4-carboxy-alpha-isothiocyanato-acetophenone, aldehydes such as carboxybenzaldehyde, ketones such as levulinic acid, thiosemicarbazide, thioamides such as succinic acid mono-thioamide, alpha-bromo-carbonic acids such as bromoacetic acid, hydrazines such as 4-hydrazinobenzoic acid, O-alkyl-hydroxyl amines such as amino-oxy-acetic acid and hydrazides such as glutaric acid monohydrazide.

As a further measure during the development of the assembly according to the invention it can be provided that those sites or regions of the surface not provided with an amino acid sequence are blocked. The blocking ensures that during or after the chemoselective reaction of the amino acid sequences with the, if necessary, functionalised surfaces, groupings or groups which have not yet reacted but are still reactive on the surface are inactivated. This blocking reaction is necessary since otherwise the added enzymatic activity or other constituents of the biological sample used react non-specifically with reactive groups on the surface which are not yet blocked and can thus possibly provide a large background signal. Such non-specific reactions with surfaces -are a frequent cause of unfavourable signal-to-noise ratios in biochemical analyses. Those compounds which are not sterically demanding, which react very well with the groups to be blocked and generate surface properties as favourable as possible are suitable for this blocking. The choice of these compounds will depend on the type of sample or the interaction partner which interacts with one of the amino acid sequences. The compound will be configured as hydrophilic if it is known that the enzymatic activity preferably binds non-specifically to hydrophobic surfaces and hydrophobic if it is known that the enzymatic activity preferably binds non-specifically to hydrophobic surfaces. Thus, it is known to the person skilled in the art that a biomolecule, such as a protein, for example, requires a three-dimensional, precisely defined structure for the correct biological function. This tertiary structure is significantly dependent on the environment. Thus, a protein in water, which is a hydrophilic solvent, has the tendency to conceal all or more accurately, as many groupings as possible in the interior. If such a protein enters a more hydrophobic environment (hydrophobic surface), folding over or unfolding of the protein and therefore inactivation can occur. On the other hand, proteins are known which in their natural mode of occurrence are present inside (hydrophobic) biomembranes Such proteins would fold over on coming in contact with a hydrophilic surface and thereby denature or become inactivated. In such a case a hydrophobic surface is desirable.

The constituents of the amino acid sequences of the assembly according to the invention are amino acids preferably selected from the group comprising the L and D amino acids. The amino acids can furthermore be selected from the group comprising natural and unnatural amino acids. A preferred group within each of the previous groups of amino acids are the corresponding alpha amino acids. The amino acid sequences can consist of a sequence of amino acids from any one of the previous groups. Thus, for example, a combination of D and L amino acids is within the scope of the invention in the same way as amino acid sequences which consist either exclusively of D or L amino acids. The constituents of the amino acid sequences can furthermore comprise molecules other than amino acids. Examples herefor are thioxo-amino acids, hydroxy acids, mercapto acids, dicarbonic acids, diamines, dithioxocarbonic acids, acids and amines. Another form of derivatised amino acid sequences are the so-called PNAs (peptide nucleic acids).

The density of the amino acid sequences is $1/cm^2$ to $2000/cm^2$ wherein the density is preferably $5/cm^2$ to $1000/cm^2$ and quite especially preferably $10/cm^2$ to $100/cm^2$. Such densities of distinct locations on a surface which can each contain an amino acid species, can be achieved using various techniques such as, for example, piezoelectrically driven pipetting robots, using fine needles made of various materials such as polypropylene, stainless steel or tungsten or corresponding alloys, using so-called pin-tools which are either slotted needles or are constructed of a ring containing the substance mixture to be applied and a needle which through the substance mixture contained in this ring, drops this onto the corresponding surface. However, capillaries connected to a motor-driven spray are also suitable (spotters). Another possibility is to apply the samples to be immobilised using suitable stamps. However, it is also possible to apply the amino acid sequences to be immobilised by hand by using suitable pipettes or so-called multipettes. It is furthermore possible to produce the densities of distinct locations given above by direct in situ synthesis of the amino acid sequences. (M. Stankova, S. Wade, K. S. Lam, M. Lebl; 1994, Synthesis of combinatorial libraries with only one representation of each structure, Pept. Res., 7, 292-298, F. Rasoul, F. Ercole, Y. Pham, C. T. Bui, Z. M. Wu, S. N. James, R. W. Trainor, G. Wickham, N.J. Maeji; 2000, Grafted supports in solid-phase synthesis, Biopolymers, 55, 207-216, H. Wenschuh, R. Volkmer-Engert, M. Schmidt, M. Schulz, J. Schneider-Mergener, U. Reineke; 2000, Coherent membrane supports for parallel microsynthesis and screening of bioactive peptides, Biopolymer., 55, 188-206, R. Frank, 1992, Spot synthesis: an easy technique for the positionally addressable, parallel chemical synthesis on a membrane support, Tetrahedron, 48, 9217-9232; A. Kramer and J. Schneider-Mergener, Methods in Molecular Biology, vol. 87: Combinatorial Peptide Library Protocols, p. 25-39, edited by: S. Cabilly; Humana Press Inc., Totowa, N.J.; Topert, F., Oires, C., Landgraf, C., Oschkinat, H. and Schneider-Mergener, J., 2001, Synthesis of an array comprising 837 variants of the hYAP WW protein domain, Angew. Chem. Int. Ed., 40, 897-900, S. P. A. Fodor, J. L. Read, M. C. Pirrung, L. Stryer, A. T. Lu, D. Solas; 1991, Light-directed spatially addressable parallel chemical synthesis, Science, 251, J. P. Pellois, W. Wang, X. L. Gao; 2000, Peptide synthesis based on t-Boc chemistry and solution photogenerated acids, J. Comb. Chem. 2, 355-360).

In a preferred embodiment of the assembly according to the invention and its various uses and applications, it is provided that the various amino acid sequences are substrates or possible substrates of enzymatic activities, which are contained in the samples as interaction partners towards which the assembly according to the invention is exposed. Enzymatic activities should generally be understood herein as those enzymatic activities which are characterised in that they transfer an atom group, a molecule or a molecular group to a molecule. Enzymatic activities should herein especially be understood as kinases, sulphotransferases, glycosyl transferases, acetyl transferases, farnesyl transferases, palmityl transferases, phosphatases, sulphatases, esterases, lipases, acetylases and proteases. The enzymatic activity will accordingly change if necessary one or a plurality of amino acid sequences of the assembly, that is one or a plurality of amino acids on the chip, with respect to its molecular weight. Such a change in the molecular weight can comprise a decrease or an increase in the same, and may involve further changes to the physicochemical properties of the amino acid sequences or the distinct locations at which respectively one species of amino acid sequence is located.

Various techniques known to the person skilled in the art can be used to detect whether a binding event takes place at one or a plurality of the various amino acid sequence species and, insofar as the interaction partner of the amino acid sequence is an enzymatic activity or carries this, whether an enzymatic conversion takes place at the respective amino acid sequence. Thus it is possible to trace a cleaving reaction. e.g. mediated by a protease, by a change in the fluorescence of a suitable substrate molecule bound to the surface. In principle, all reactions during which the molecule bound to the surface is changed in molecular weight by transfer of other molecules (co-substrates) can be traced by incorporating a radioactive label into the co-substrate. For this purpose the radioactivity incorporated into the modified molecule bound to the surface must be quantified after the reaction. With the aid of such radioactive labels, all transferases such as, for example, kinases, acetyl transferases, farnesyl transferases and glycosyl transferases can be characterised with reference to enzymatic activity. Alternatively, reactive groups which have been produced from the respective enzymatic reaction at the respective amino acid sequence and which were not previously present can be detected by means of subsequent specific reactions. For example, a mercapto function obtained after an enzymatic reaction can be detected by means of a following reaction with Ellman reagent.

It is within the scope of the present invention that the assembly comprises a certain number of different amino acid species. In this case it can be provided that the same amino acid sequence is present at a plurality of distinct locations on the surface or the support material. Thus, on the one hand, an internal standard can be achieved and on the other hand, however, possible edge effects can be represented and recorded.

A further development of the invention provides that at least two or a plurality of assemblies are joined together such that between the two assemblies there is only a very small gap into which the amino acid sequences of the two assemblies extend (see FIG. 12B). This development is herein also called a support assembly. This opens up a possibility for carrying out a plurality of tests using a very small sample volume. The width of the gap is 2 mm, preferably 0.5 mm and preferably less than 0.1 mm. This gives a liquid volume of less than 100 nL relative to a surface area of 1 mm$^2$. It is within the scope of the present invention that the assemblies forming the support assembly differ in respect of development. These differences can consist in the fact that the amino acid sequences are all or partly different. It is furthermore possible that the amino acid sequences in the different assemblies are arranged completely or partly at other distinct locations.

The assembly according to the invention offers a number of possible applications. One such application is the determination of the substrate specificity of the enzymatic activity (FIG. 12, compound C). In this case, the procedure is that in a first step an assembly according to the invention or chip is prepared and this is brought into contact, and if necessary incubated, with a sample containing the respective enzymatic activity. The reaction is then detected between one or a plurality of amino acid sequences present on the assembly (FIG. 12A, compounds $B_1$-$B_3$ or FIG. 12B, compounds $B_1$-$B_5$) and the enzymatic activity (FIG. 12, compound C), wherein the detection methods described above can be used. As a result of the arrangement of the different amino acid sequence species at distinct locations, a reaction event of a specific amino acid sequence or amino acid sequence species (both terms are used herein synonymously) can thus be uniquely assigned to a specific location and the substrate specificity of the enzymatic activity can be determined therefrom (see FIGS. 8, 9 and 10).

Starting from the substrate specificity, for example, the influence of various substances on the respective reaction can be investigated. For example, depending on the respective substrate, an enzymatic activity can undergo a specific modification by a factor added to the reaction formulation containing the enzymatic activity, for example, a low-molecular compound.

Another application of the assembly according to the invention is in displaying the differential analysis of the enzymatic activities of a sample. An especially important sample in this respect is the proteome of a cell with reference to which this aspect of the invention is explained in the following. In this case, unlike the application described previously, attention is not focussed on the specificity of an individual enzymatic activity with respect to the amino acid species present on the surface but rather to a certain extent on an instantaneous snapshot of the enzymatic activities in a sample with respect to the various amino acid sequence species of the assembly. This instantaneous snapshot was made under certain conditions which prevailed at the time the sample was taken. In the case of the proteome, this can for example be the state after exposure of the cell from which the sample was obtained, to a certain compound. One or a plurality of further samples are then taken wherein the conditions which prevailed at the time of sampling are changed, for example, the cell was no longer exposed to said compound and an analysis is then made. Depending on the selected method of detection, the result of the reaction event is then compared under the different conditions and from this it can be determined whether and, if so, to what extent the pattern from the respective reaction event has changed. On the other hand, such an assembly of amino acid sequences can also be used to compare biological samples one with the other such as cell lysates, for example, or biological fluids of one species or different species by means of pattern recognition or to catalogue these biological samples by means of the pattern obtained. Such a pattern is then used in the transferred sense as a fingerprint of the biological sample studied. Thus, the method according to the invention can be used for identification or individualisation. The identification can take place on different systematic levels, i.e., the allocation of suitably studied sample to a strain, a class, an order, a family, a genus, or a type. Furthermore, the identification can also take on the level of the type between individuals of the same type or race. For example, this method can be used in forensic science. A further application of the method can be seen in determining, diagnosing or predicting pathological states such as cancer or a pattern of enzymatic activity changed compared with the norm (both quantitatively and qualitatively).

BRIEF DESCRIPTION OF THE DRAWINGS

The present invention is now explained with reference to the following drawings and examples from which further features, exemplary embodiments and advantages can be obtained. In the figures:

FIG. 11: shows an overview of various chemoselective reactions; and

FIG. 12: shows a schematic structure of various embodiments of an assembly of compounds directionally immobilised on a support surface.

The figures are now described in detail.

Figure 1:
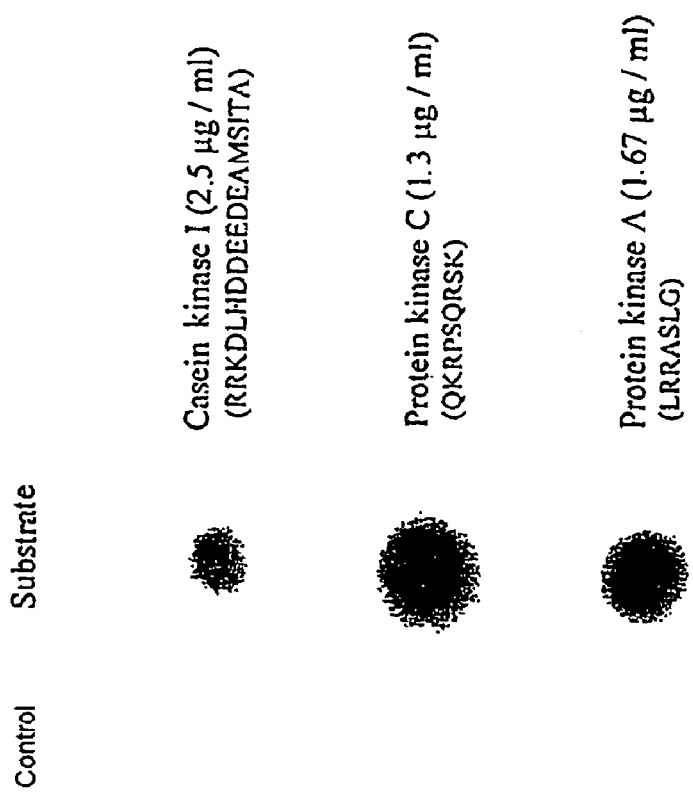
FIG. 1. shows the result of incubating a differently modified glass surface with different kinases.

FIG. 1. The kinase substrates given in parentheses (modified at the N-terminus with the dipeptide cysteinyl-β-alanine) were coupled to a maleinimido-functionalised glass surface by a Michael addition (Example 1). Peptides for which the serine amino acid to be phosphorylated was exchanged for the non-phosphorylatable amino acid alanine were used as negative controls. The glass surface was first pre-incubated for 10 minutes using 10 mL of 100 µM ATP solution in 50 mM of sodium phosphate buffer pH 7.5. The corresponding kinases were then spotted on together with ATP/$\gamma^{32}$P-ATP mixture (1 µL, 5 U/mL in each case) and incubated for 30 minutes at 25° C. (Example 29). The phosphorylation of the corresponding peptides was detected using a FUJIFILM PhosphorImager.

Figure 2:
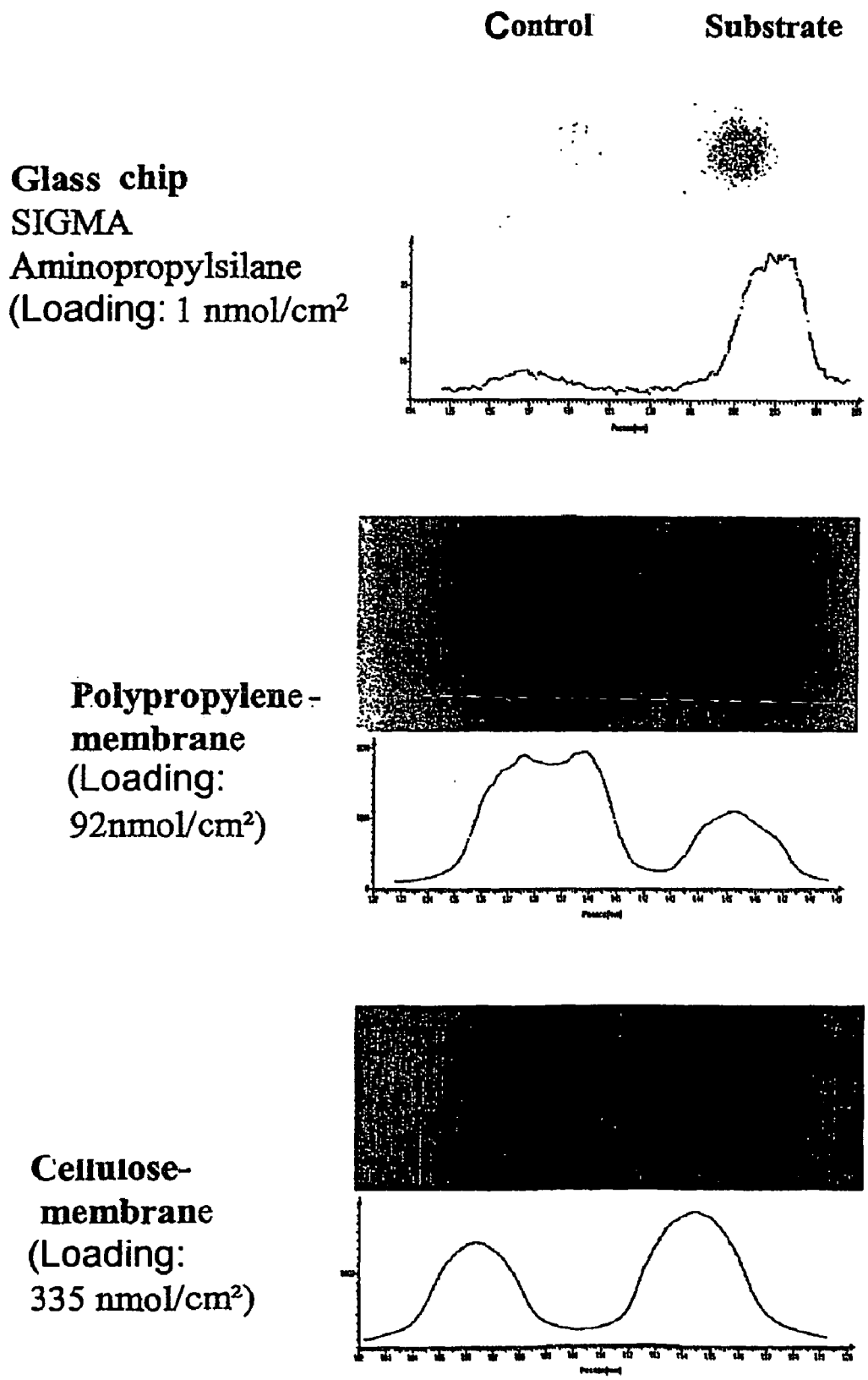
FIG. 2 shows the result of incubating various modified surfaces with protein kinase A.

FIG. 2. The peptide Leu-Arg-Arg-Ala-Ser-Leu-Gly-NH$_2$ and the control peptide Leu-Arg-Arg-Ala-Ser-Leu-Gly-NH$_2$, each modified at the N-terminus with the dipeptide cysteinyl-β-alanine, were coupled to a maleinimido-functionalised surface by a Michael addition (Example 1; maleinimidobutyryl-β-alanine-functionalised cellulose as well as maleinimidobutyryl-β-alanine-functionalised, modified polypropylene membranes). The surfaces thus modified were first pre-incubated for 10 minutes using 10 mL of 100 µM ATP solution in 50 mM of sodium phosphate buffer pH 7.5. Protein kinase A was then spotted on together with ATP/$\gamma^{32}$P-ATP mixture (100 µL/mL; 100 µCi/mL) (1 µL. 2 U/mL in each case) and incubated for 30 minutes at 25° C. (Example 30). The phosphorylation of the corresponding peptides was detected using a FUJIFILM PhosphorImager. The signal intensity of the respective spot is given below the figures. It is clear that under the selected experimental conditions in the case of modified cellulose or polypropylene surfaces, in principle only non-specific binding of ATP or kinase to the peptides is measured. In the case of the modified glass surfaces, however, the signal for the substrate amino acid sequence is a factor of 4-5 larger than the signal for the corresponding control amino acid sequence.

Figure 3:
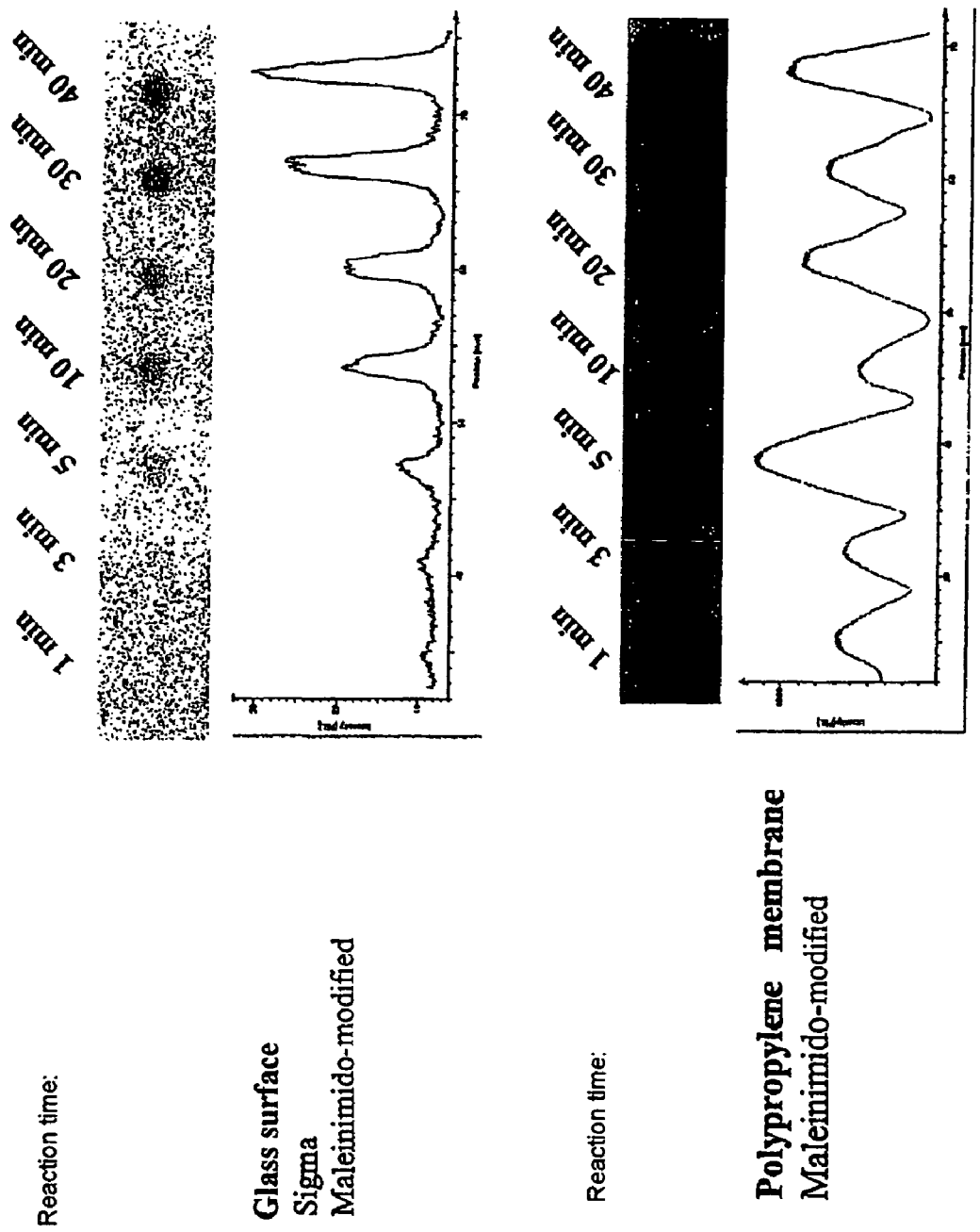
FIG. 3 shows the result of time-dependent incubation of various modified surfaces with protein kinase A.
Figure 4:
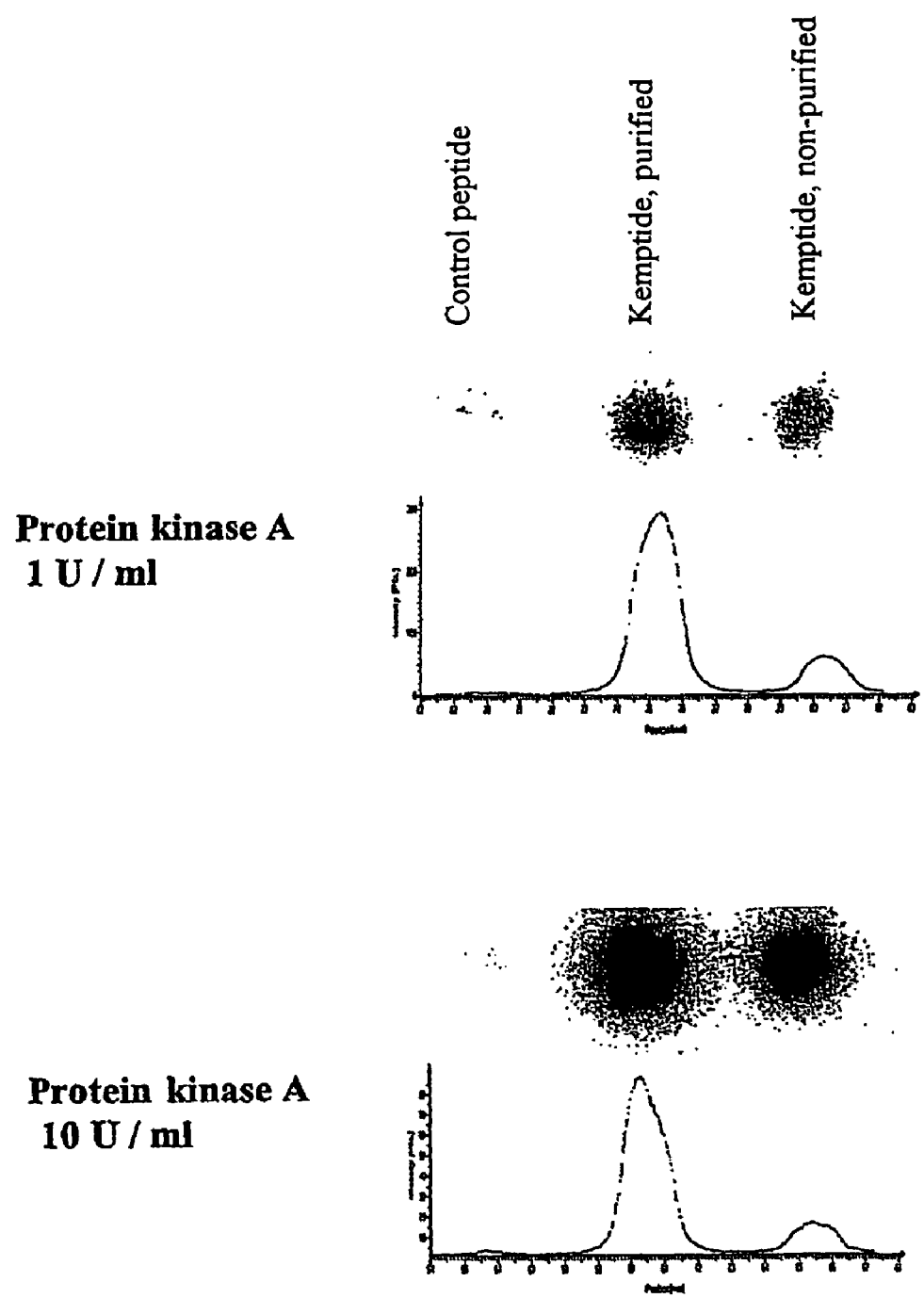
FIG. 4 shows the result of incubating a differently modified glass surface with different concentrations of protein kinase A
Figure 5:
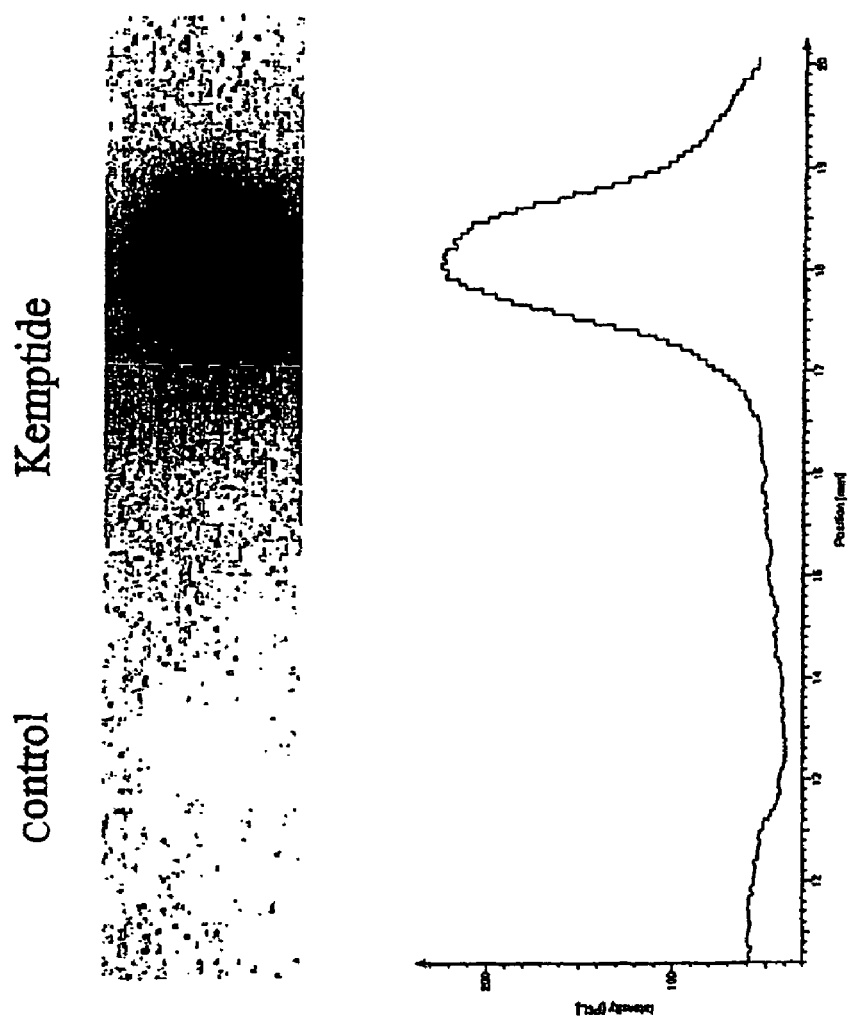
FIG. 5 shows the result of incubating a modified glass surface with protein kinase A.

FIG. 3. The peptide Leu-Arg-Arg-Ala-Ser-Leu-Gly-NH$_2$, modified at the N-terminus with the dipeptide cysteinyl-β-alanine, was coupled to maleinimido-functionalised surfaces by a Michael addition (maleinimido-functionalised glass surface, Sigma, Silane-Prep™, S4651; as well as maleinimidobutyryl-β-alanine-functionalised, modified polypropylene membranes). The modified glass surfaces were first pre-incubated for 10 minutes using 20 mL of 100 µM ATP solution in 50 mM of sodium phosphate buffer pH 7.5. Protein kinase A was then spotted on together with ATP/$\gamma^{32}$ P-ATP mixture (100 µL/mL; 100 µCi/mL) (1 µL, 2 U/mL in each case) and incubated for the given time at 25° C. (Example 31). The phosphorylation of the corresponding peptides was detected using a FUJIFILM PhosphorImager. The signal intensity of the respective spot is given below the figures. It is clear that under the selected experimental conditions in the case of modified polypropylene surfaces, in principle only non-specific binding of ATP or kinase to the peptides is measured. In the case of the modified glass surfaces, however, a clear time dependence can be identified for the kinase-mediated incorporation of radioactivity into the substrate amino acid sequence. FIG. 4. The control peptide Leu-Arg-Arg-Ala-Ala- Leu-Gly-NH$_2$, the peptide Leu-Arg-Arg-Ala-Ala-Leu-Gly-NH$_2$ and the synthesis raw product Leu-Arg-Arg-Ala-Ala-Leu-Gly-NH$_2$, each modified at the N-terminus with the dipeptide cysteinyl-β-alanine, were coupled to a maleinimido-functionalised glass surface by a Michael addition (Example 1). The modified glass surface was first pre-incubated for 10 minutes using 10 mL of 100 μM ATP solution in 50 mM of sodium phosphate buffer pH 7.5. The modified glass surface was then covered with a cover glass and Protein kinase A (1 U/mL or 10 U/mL) together with ATP/γ$^{32}$P-ATP mixture (100 μL/mL; 100 μCi/mL) was then inserted into the intermediate space formed thereby by means of capillary force (Example 25). After incubation for 30 min at 25° C. the phosphorylation of the corresponding peptides was detected using a FUJIFILM PhosphorImager. The signal intensity of the respective spot is given below the figures. It is clear that under the selected experimental conditions the signal intensity for the purified amino acid sequence is 500% higher than that for the synthesis product. The signal intensity for the purified amino acid sequence is approximately 300 times higher than that for the corresponding control amino acid sequence. Together with the approximately ten times lower quantity of activity required for a comparable signal (compared with cellulose surfaces), an improvement in signal by a factor of 3000 is thus obtained. FIG. 5. The control peptide Leu-Arg-Arg-Ala-Ala-Leu-Gly-NH$_2$, and the peptide Leu-Arg-Arg-Ala-Ala-Leu-Gly-NH$_2$, each modified at the N-terminus with the dipeptide cysteinyl-β-alanine, were coupled to a maleinimido-functionalised glass surface by a Michael addition (Example 1). The modified glass surface was first pre-incubated for 10 minutes using 10 mL of 100 μM ATP solution in 50 mM of sodium phosphate buffer pH 7.5. The modified glass surface was then covered with a cover glass and Protein kinase A (10 U/mL) together with ATP/γ$^{32}$P-ATP mixture (100 μM/mL; 100 μCi/mL) was then inserted into the intermediate space formed thereby by means of capillary force. After incubation for 30 min at 25° C. the phosphorylation of the corresponding peptides was detected using a FUJIFILM PhosphorImager. The signal intensity of the respective spot is given below the figures. It is clear that under the selected experimental conditions the signal intensity for the substrate amino acid sequence is 800% higher than that for the control product.

Figure 6:
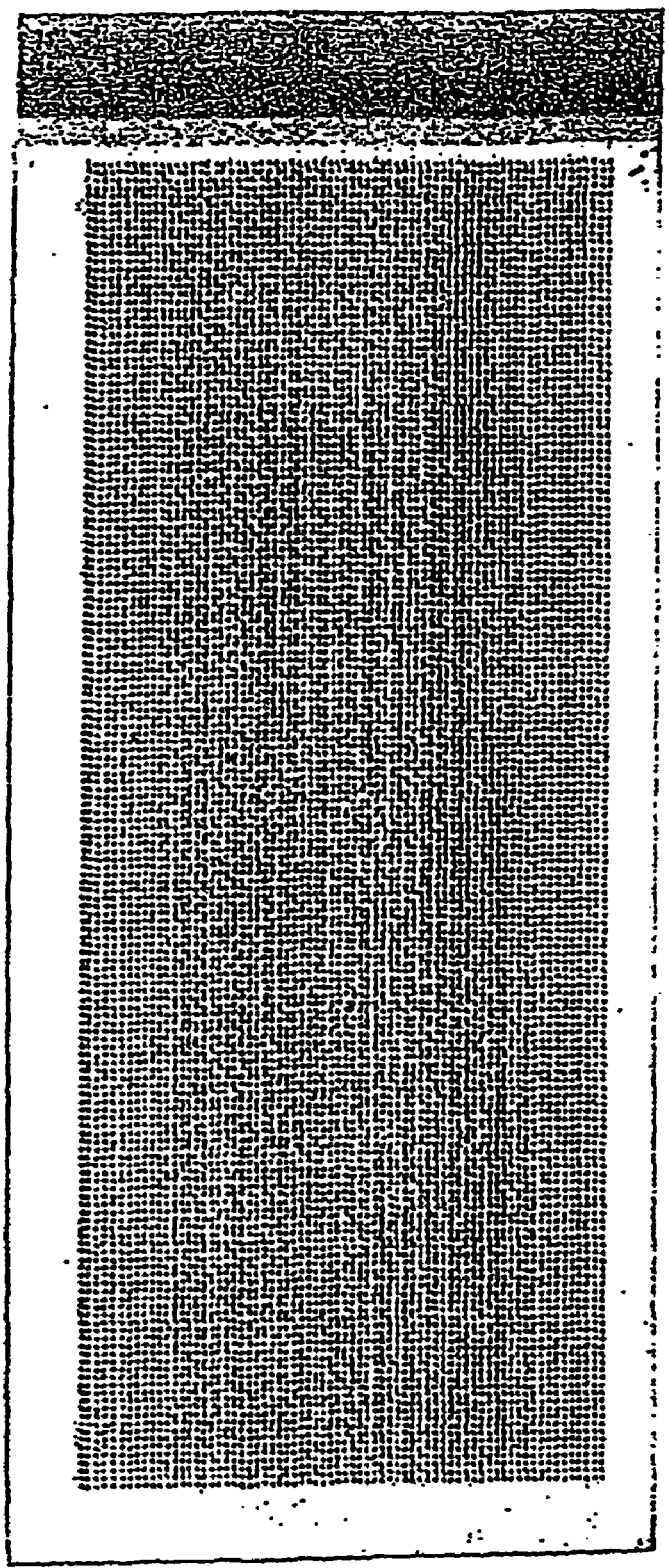
FIG. 6: shows the result of incubating a modified glass surface (11760 spots) with a kinase.

FIG. 6. A glass surface modified with the peptide Leu-Arg-Arg-Ala-Ala-Ser-Leu-Gly-thioamide (see Example 24) amino acid sequence was dissolved in 200 mM sodium phosphate buffer pH 5.5 and at room temperature respectively 1 nL of this solution in an assembly of 70 rows and 168 gaps (total 11760) was applied to the bromoketone-functionalised glass surfaces (Example 10) using a NanoPlotter from Gesim. The spot-to-spot distance was 0.3 mm. The glass surfaces thus treated were then subjected to microwave treatment for 2 min and then incubated for 3 hours at room temperature. Pre-incubation was then carried out for 10 minutes using 10 ml of 100 μM ATP solution in 50 mM of sodium phosphate buffer pH 7.5. The modified glass surface was then covered with a second glass surface and Protein kinase A (10 U/mL) together with ATP/γ$^{32}$P-ATP mixture (100 μM/mL; 100 μCi/mL) was then inserted into the intermediate space formed thereby by means of capillary force (see Example 31). After incubation for 30 min at 25° C. the phosphorylation of the corresponding peptides was detected using a FUJIFILM PhosphorImager. It is clear that on the one hand, the linking of the immobilised kinase substrate is tolerated by the protein kinase A and on the other hand, the modification of the glass surfaces takes place uniformly and without larger fluctuations in the immobilisation density. It is furthermore clear that the resolution of the PhosphorImager used here is sufficient to analyse more than 11000 measurement points per biochip.

Figure 7:
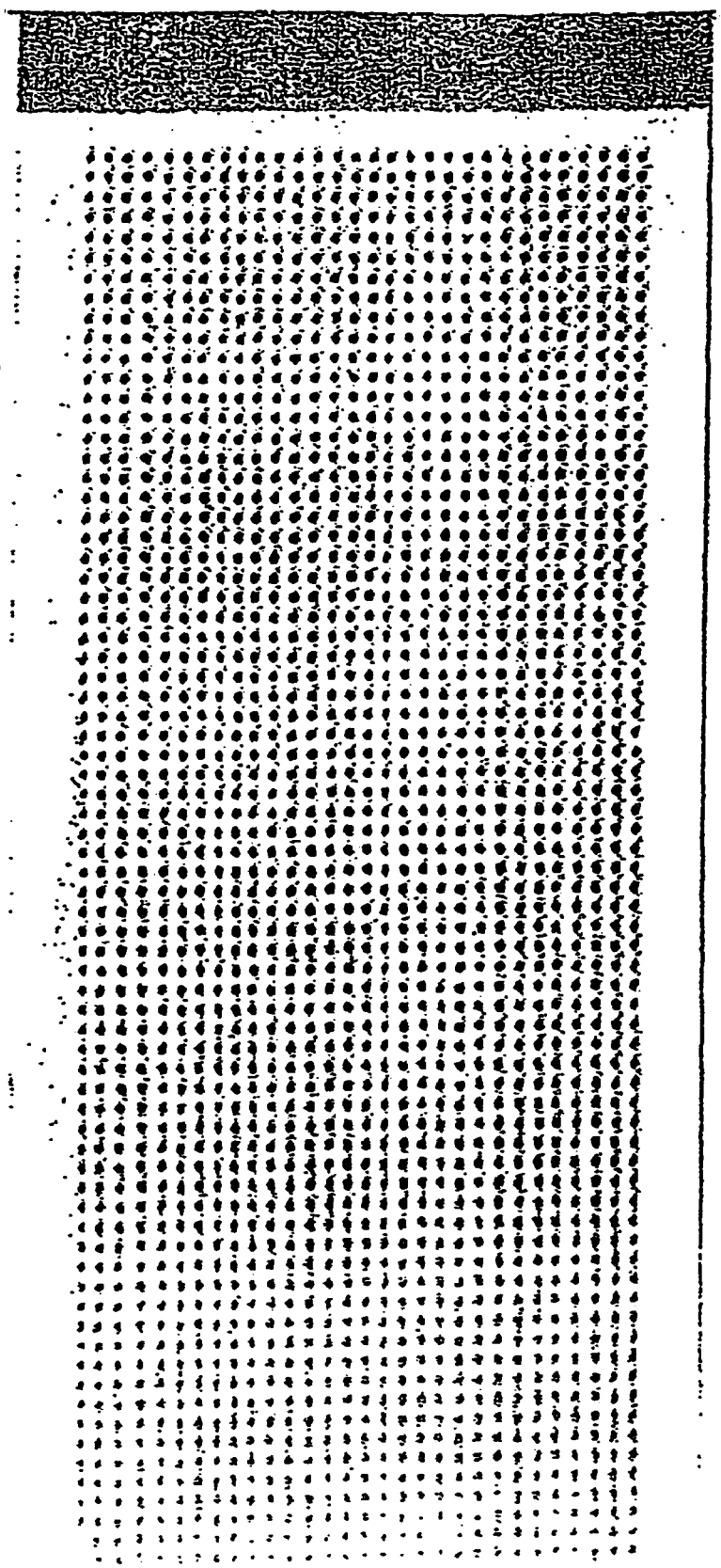
FIG. 7: shows the result of incubating a modified glass surface (960 spots) with a kinase.

FIG. 7. A glass surface modified with the peptide Dpr (Aoa)-Leu-Arg-Arg-Ala-Ser-Leu-Gly-NH$_2$ (see Example 22) was first pre-incubated for 10 minutes using 10 ml of 100 μM ATP solution in 50 mM of sodium phosphate buffer pH 7.5. The modified glass surface was then covered with a second glass surface and Protein kinase A (10 U/mL) together with ATP/γ$^{32}$P-ATP mixture (100 μM/mL; 100 μCi/mL) was then inserted into the intermediate space formed thereby by means of capillary force. After incubation for 30 min at 25° C. the phosphorylation of the corresponding peptides was detected using a FUJIFILM PhosphorImager (see Example 14). It is clear that on the one hand, the linking of the immobilised kinase substrate is tolerated by the protein kinase A and on the other hand, the modification of the glass surfaces takes place uniformly and without larger fluctuations in the immobilisation density. It is furthermore clear that the resolution of the PhosphorImager used here is sufficient to analyse more than 950 measurement points per biochip.

Figure 8:
FIG. 8: shows the result of incubating a glass surface modified with a set of potential substrate peptides and corresponding control peptides with protein kinase C.
Figure 8:
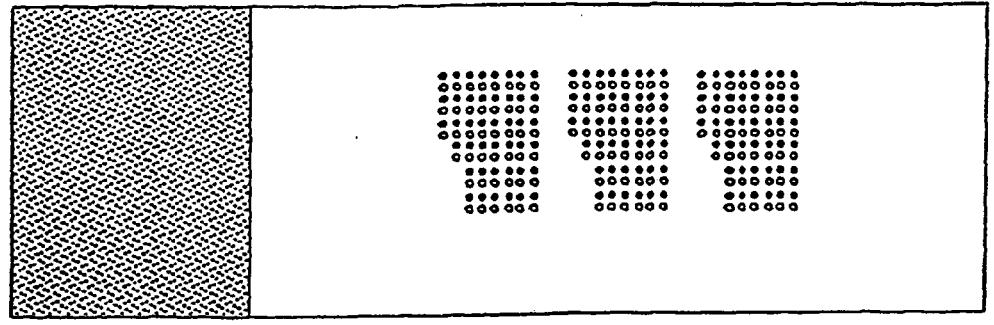

FIG. 8. Precisely 43 serine and/or threonine-containing peptides (potential substrate peptides for kinases) and the corresponding control peptides, each modified at the N-terminus with the dipeptide cysteinyl-β-alanine, were coupled to a maleinimido-functionalised glass surface by a Michael addition (Example 18). In the control peptides the serine and/or threonine residues were replaced by alanine, the sequence remaining otherwise the same. The application was carried out using a NanoPlotter from Gesim. The spot-to-spot distance was 1 mm and 0.8 nL of a peptide solution in 100 mM PBS buffer pH 7.8, containing 20% glycerin, was applied per spot. The peptide assembly is shown in FIG. 8A. Here a filled circle represents a serine- or threonine-containing potential substrate peptide and an open circle stands for a control peptide. Three identical subarrays were applied to the glass surface. The numbering of the spots can be seen in FIG. 8C, the sequences of the peptides used are obtained from Example 18. After application of the peptides, the modified glass surface was first pre-incubated for 10 minutes using 10 ml of 100 μM ATP solution in 50 mM of sodium phosphate buffer pH 7.5. The modified glass surface was then covered with a second glass surface and Protein kinase C (10 U/mL) together with ATP/γ$^{32}$P-ATP mixture (100 μM/mL; 100 μCi/mL) was then inserted into the intermediate space formed thereby by means of capillary force. After incubation for 30 min at 25° C. the phosphorylation of the corresponding peptides was detected using a FUJIFILM PhosphorImager (Example 38). The resulting picture is shown in FIG. 8B. The spots having higher signal intensity in all three subarrays were assigned to the corresponding peptides phosphorylated by the protein kinase C. Their primary structures are shown in FIG. 8D. It is clear that peptides known as protein kinase C substrates (substrate peptide No. 3, 23, 27, 41, 43) and other peptides not described as substrates for protein kinase C are recognised and phosphorylated by this kinase on the modified glass surface. It is thus clear that such an assembly is suitable for characterising the substrate specificity of a kinase, such as protein kinase C, for example.

Figure 9:
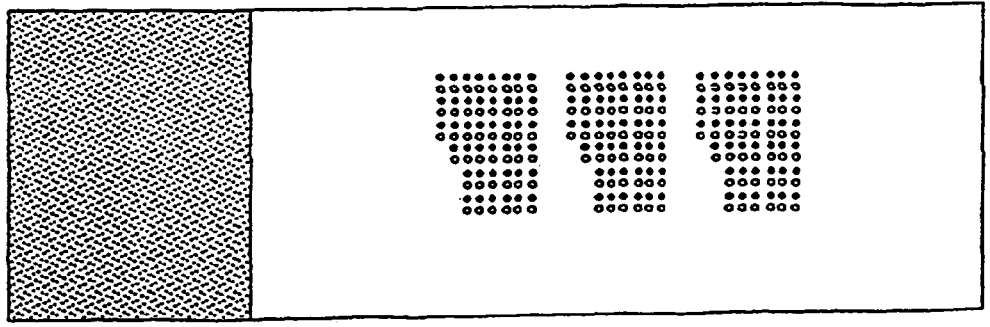
FIG. 9: shows the result of incubating a glass surface modified with a set of potential substrate peptides and corresponding control peptides with protein kinase A.

FIG. 9. Precisely 43 serine and/or threonine-containing peptides (potential substrate peptides for kinases) and the corresponding control peptides, each modified at the N-terminus with the dipeptide cysteinyl-β-alanine, were coupled to a maleinimido-functionalised glass surface by a Michael addition (Example 18). In the control peptides the serine and/or threonine residues were replaced by alanine, the sequence remaining otherwise the same. The application was carried out using a NanoPlotter from Gesim. The spot-to-spot distance was 1 mm and 0.8 nL of a peptide solution in 100 mM PBS buffer pH 7.8, containing 20% glycerin, was applied per spot. The peptide assembly is shown in FIG. 9A. Here a filled circle represents a serine- or threonine-containing potential substrate peptide and an open circle stands for a control peptide. Three identical subarrays were applied to the glass surface. The numbering of the spots can be seen in FIG. 9C, the sequences of the peptides used are obtained from Example 18. After application of the peptides, the modified glass surface was first pre-incubated for 10 minutes using 10 ml of 100 µM ATP solution in 50 mM of sodium phosphate buffer pH 7.5. The modified glass surface was then covered with a second glass surface and Protein kinase A (10 U/mL) together with ATP/$\gamma^{32}$P-ATP mixture (100 µM/mL; 100 µCi/mL) was then inserted into the intermediate space formed thereby by means of capillary force. After incubation for 30 min at 25° C. the phosphorylation of the corresponding peptides was detected using a FUJIFILM PhosphorImager (Example 39). The resulting picture is shown in FIG. 9B. The spots having higher signal intensity in all three subarrays were assigned to the corresponding peptides phosphorylated by the protein kinase A. Their primary structures are shown in FIG. 9D. It is clear that with one exception, all peptides on the modified glass surface are recognised and phosphorylated by protein kinase A which carry two arginine residues in position −2 and −3 (N-terminal) to serine. The sequence motif RRxS is described as a preferred substrate motif for protein kinase A (A. Kreegipuu, N. Blom, S. Brunak, J. Jarv, 1998, Statistical analysis of protein kinase specificity determinants, *FEBS Lett.*, 430, 45-50). The peptide 83 is probably not phosphorylated because of the excessive N-terminal localisation of the substrate motif. It is thus clear that such an assembly is suitable for characterising the substrate specificity of a kinase, such as protein kinase A, for example.

Figure 10:
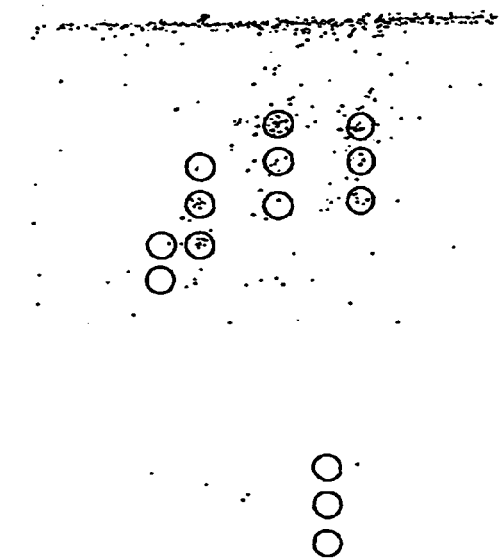
FIG. 10: shows the result of incubating a glass surface modified with a set of potential substrate peptides with protein kinase A.

FIG. 10. Precisely 79 peptides, each modified at the N-terminus with the dipeptide amino-oxyacetic acid-β-alanine, were coupled to an aldehyde-functionalised glass surface by a Michael addition (Example 20). The application was carried out using a NanoPlotter from Gesim. The spot-to-spot distance was 1.5 mm and 0.8 nL of a peptide solution in DMSO was applied per spot. The 13-mer peptides overlap with respectively 11 amino acid residues and together completely cover the primary structure of MBP, that is together they form a scan through the myelin basic protein (MBP) from bos taurus (SWISSPROT Accession number P02687). The primary structure of MBP is shown in FIG. 10C. For the residues shown in bold print a phosphorylation by protein kinase A was described in the prior art (A. Kishimoto, K. Nishiyama, H. Nakanishi, Y. Uratsuji, H. Nomura, Y. Takeyama, Y. Nishizuka, 1985, Studies on the phosphorylation of myelin basic protein by protein kinase C and adenosine 3':5'-monophosphate-dependent protein kinase, *J. Biol. Chem.*, 260, 12492-12499). The 13-mer peptides in the scan show a sequence shift of two amino acids. The peptide assembly is shown in FIG. 10B. Thus, peptide No. 1 represents the amino acid sequence 1-13 of the primary structure of MBP, peptide No. 2 represents the amino acid sequence 3-15 of the primary structure of MBP, etc. Three identical subarrays were applied to the glass surface. One of these subarrays is shown in FIG. 10A. After application of the peptides, the modified glass surface was first pre-incubated for 10 minutes using 10 ml of 100 µM ATP solution in 50 mM of sodium phosphate buffer pH 7.5. The modified glass surface was then covered with a cover glass and Protein kinase A (10 U/mL) together with ATP/$\gamma^{32}$P-ATP mixture (100 µM/mL; 100 µCi/mL) was then inserted into the intermediate space formed thereby by means of capillary force (see Example 40). After incubation for 30 min at 25° C. the phosphorylation of the corresponding peptides was detected using a FUJIFILM PhosphorImager. The resulting picture is shown in FIG. 10A. The spots having higher signal intensity in all three subarrays were assigned to the corresponding peptides phosphorylated by the protein kinase A. Their primary structures are shown in FIG. 10D. It is clear that most of the peptides on the modified glass surface are recognised and phosphorylated by protein kinase A which was also found in the experiment carried out in solution (A. Kishimoto, K. Nishiyama, H. Nakanishi, Y. Uratsuji, H. Nomura, Y. Takeyama, Y. Nishizuka, 1985, Studies on the phosphorylation of myelin basic protein by protein kinase C and adenosine 3':5'-monophosphate-dependent protein kinase, *J. Biol. Chem.*, 260, 12492-12499).

FIG. 11. Shows an overview of various chemoselective reactions according to the prior art: A) aldehyde ($R^4$=H) or ketone ($R^4$ not H) and amino-oxy compounds react to give oximes, B) aldehyde ($R^4$=H) or ketone ($R^4$ not H) and thiosemicarbazides react to give thiosemicarbazones, C) aldehyde ($R^4$=H) or ketone ($R^4$ not H) and hydrazides react to give hydrazones, D) aldehyde ($R^4$=H) or ketone ($R^4$ not H) and 1,2-aminothiols react to give thiazolines (X=S) or 1,2-amino alcohols to give oxazolines (X=O) or 1,2-diamines react to give imadazolines (X=NH), E) thiocarboxylates and α-halocarbonyls react to give thioesters, F) thioesters and β-aminothiols react to give β-mercaptoamides, F) mercaptane and maleinimide react to give succinimides. The radical $R^1$ in this case represents alkyl, alkenyl, alkynyl, cycloalkyl or aryl radicals or heterocyclic compounds or surfaces and the radicals $R^4$—$R^6$ represent alkyl, alkenyl, alkynyl, cycloalkyl or aryl radicals or heterocyclic compounds or surfaces or H, D or T, wherein alkyl stands for branched and unbranched $C_{1-20}$-alkyl, $C_{3-20}$-cycloalkyl, preferably for branched and unbranched $C_{1-12}$-alkyl, $C_{3-12}$-cycloalkyl, and especially preferably for branched and unbranched $C_{1-6}$-alkyl, $C_{3-6}$-cycloalkyl residues. Alkenyl stands for branched and unbranched $C_{2-20}$ alkenyl, branched and unbranched $C_{1-20}$-alkyl-$C_{2-20}$-alkenyl, $C_{1-20}$—(—O/S—$C_{2-20}$)$_{2-20}$-alkenyl, branched and unbranched heterocyclyl-$C_{2-20}$-alkenyl, $C_{3-20}$-cycloalkenyl, preferably for branched and unbranched $C_{2-12}$-alkenyl, branched and unbranched $C_{1-12}$—(—O/S—$C_{2-12}$)$_{2-12}$-alkenyl, especially preferably for branched and unbranched $C_{2-12}$-alkenyl, branched and unbranched $C_{1-6}$—(—O/S—$C_{2-8}$)$_{2-8}$-alkenyl residues; alkynyl stands for branched and unbranched $C_{2-20}$ alkynyl, branched and unbranched $C_{1-20}$—(—O/S—$C_{2-20}$)$_{2-20}$-alkynyl, preferably for branched and unbranched $C_{2-12}$-alkynyl, branched and unbranched $C_{1-12}$—(—O/S—$C_{2-12}$)$_{2-12}$-alkynyl, especially preferably for branched and unbranched $C_{2-6}$-alkynyl, branched and unbranched $C_{1-6}$—(—O/S—$C_{2-8}$)$_{2-8}$-alkynyl radicals; cycloalkyl stands for bridged and unbridged $C_{3-40}$ cycloalkyl, preferably for bridged and unbridged $C_{3-26}$ cycloalkyl, especially preferably for bridged and unbridged $C_{3-15}$ cycloalkyl radicals; aryl stands for substituted and unsubstituted, mono- or multi-linked phenyl, pentalenyl, azulenyl, anthracenyl, indacenyl, acenaphtyl, fluorenyl, phenalenyl, phenanthrenyl, preferably substituted and unsubstituted, mono- or multi-linked phenyl, pentalenyl, azulenyl, anthracenyl, indenyl, indacenyl, acenaphtyl, fluorenyl, especially preferably for substituted and unsubstituted, mono- or multi-linked phenyl, pentanenyl, anthracenyl residues, and their partly hydrated derivatives. Heterocyclic compounds can be saturated and unsaturated 3-15-membered mono-, bi- and tricyclic rings with 1-7 heteroatoms, preferably 3-10-membered mono-, bi- and tricyclic rings with 1-5 heteroatoms and especially preferably 5-, 6- and 10-membered mono-, bi- and tricyclic rings with 1-3 heteroatoms.

In addition, at the alkyl, alkenyl, alkynyl, cycloalkyl, aryl, heteroatoms, heterocyclic compounds, biomolecules or natural substance 0 to 30 (preferably 0 to 10, especially preferably 0 to 5) of the following substituents can occur singly or in combination with one another: fluorine, chlorine, bromine, iodine, hydroxyl, amide, ester, acid, amine, acetal, ketal, thiol, ether, phosphate, sulphate, sulphoxide, peroxide, sulphonic acid, thioether, nitrile, urea, carbamate, wherein the following are preferred: fluorine, chlorine, bromine, hydroxyl, amide, ester, acid, amine, ether, phosphate, sulphate, sulphoxide, thioether, nitrile, urea, carbamate and especially preferred are: chlorine, hydroxyl, amide, ester, acid, ether, nitrile.

FIG. 12. Shows a schematic diagram of various embodiments of the incubation of an assembly of compounds ($B_1$-$B_5$) on the surface of a support with an agent (enzymatic activity C) which is capable of reducing or increasing the molecular weight under the given conditions for one or a plurality of compounds in the immobilised state. The link between the surface and the immobilised compounds (A) should be covalent and regioselective. Fig. A shows an embodiment in which the agent C is applied to the surface. Fig. B however shows an embodiment in which the agent C is applied between two surfaces facing one another which can either contain the same or different assemblies of immobilised compounds. The following examples relate to the functionalisation of glass whose surface is required as a surface for an immobilisation (Examples 1 to 14), the immobilisation of various peptides provided with a reactive group on a surface (Examples 15 to 24) and the analysis of kinase-mediated peptide modification using the immobilised peptides according to the invention (Examples 25-34). The abbreviations listed below are used:

Ala, A L-alanine
Aoa, O Amino oxyacetic acid
Arg, R L-arginine
Asn, N L-asparagine
Asp, D L-asparaginic acid
ATP Adenosine-5'-triphosphate
βAla, B, BAL β-alanine, 3-aminopropionic acid
Boc Tertiary butoxycarbonyl
Cit L-citrulline
Cys, C L-cysteine
DCM Dichloromethane
DIC N,N'-diisopropyl carbodiimide
DIPEA N,N'-diisopropyl ethylamine
DMF N,N'-dimethyl formamide
DMF N,N'-dimethyl formamide
DMSO Dimethyl sulphoxide
EGTA Ethylene glycol-bis-(2-aminoethyl)-N,N,N',N'-tetracetic acid
Et Ethyl
Fmoc 9-fluorenyl methoxycarbonyl
Gln, Q Glutamine
Glu, E L-glutaminic acid
Gly, G Glycine
HBTU O-(benzotriazol-1-yl)-N,N,N',N'-tetramethyl uronium hexafluorophosphate
His, H L-histidine
HPLC High-performance liquid chromatography
Ile, I L-isoleucine
L Liter
Leu, L L-leucine
Lys, K L-lysine
M Molar
MBHA Methylbenzhydryl amine
MBP Myelin basic protein
MeOH Methanol
Met, M L-methionine
mL Milliliter
mM Millimolar
mRNA Messenger RNA
nL Nanoliter
Phe, F L-phenylamine
Pbf 2,2,4,6,7-pentamethyl-dihydrobenzofuran-5-sulphonyl
Pro, P L-proline
PTFE Polytetrafluoroethylene
PVC Polyvinyl chloride
PVDF Polyvinyl difluoride
RNA Ribonucleic acid
RP Reversed-phase
RT Room temperature
SDS Sodium lauryl sulphate
Ser, S L-serine
tBu Tertiary butyl
TFA Trifluoroacetic acid
THF Tetrahydrofuran
Thr, T L-threonine
Tris 2-amino-2-hydroxymethyl-1,3-propanediol
Trp, W L-tryptophan
Tween20 Polyoxyethylene-sorbitant-monolaurate (trademark of Atlas Chemie)
Tyr, Y L-tyrosine
U Unit
Val, V L-valine The following reagents and solvents were used:
Bromine, tert-butyl methyl ether, 1,3-diisopropyl carbodiimide, N,N-diisopropyl ethylamine glacial acetic acid, glycerin, urea, 40% hydroxyamine solution, piperidine, triethylamine, dichloromethane, diethylether, N,N-dimethylformamide, ethanol, methanol and tetrahydrofuran come from Merck Eurolab (Darmstadt, Germany). Oxalyl chloride, sodium thiocyanate, trifluroacetic acid, dimethyl sulphoxide, thioacetamide, Lawessons reagent, formic acid and thiourea were obtained from Fluka (Deisenhofen, Germany). Adenosine-5'-triphosphate, 2-amino-2-hydroxymethyl-1,3-propanediol hydrochloride, sodium chloride, magnesium chloride, 1,4-dithio-DL-threitol, sodium lauryl sulphate, polyoxyethylene soribitant monolaurate and ethylene glycol bis-(2-aminoethyl)-N,N,N',N'-tetracetic acid come from sigma (Taufkirchen, German). The Rink amide MBHA resin, (benzatriazol-1-yl)-N,N,N',N'-tetramethyl uronium hexafluorophosphate as well as all Fmoc amino acid pentafluorophenyl esters were obtained from Novabiochem (Bad Soden, Germany).

Whatman 50 cellulose membranes (Whatman Maidestone, UK) were used for the SPOT synthesis.

Chromatography and physical data:
RP-18-HPLC-MS analyses were carried out by chromatography using a Hewlett Packard Series 1100 system (G1322A degasser, G1311A quaternary pump, G1313A automatic sampler, G1316A thermostatically controlled column box, G1314 variable UV detector) and coupled ESI-MS (Finnigan LCQ Ion Trap Mass Spectrometer). The separation was carried out using RP-18 column material (Vydac 218 TP5215, 2.1×150 mm, 5 μm, C18, 300 A with precolumn) at 30° C. and a flux of 0.3 mL/min using a linear gradient for all chromatograms (5-95% B within 25 min, wherein A: 0.05% TFA in water and B: 0.05% TFA in $CH_3CN$). The UV detection was carried out at X=220 mm).

Preparative HPLC was carried out using a Merck/Hitachi system (L-6250 quaternary pump, L-/400 variable UV detector, D-7000 interface, Software: HPLC Systemmanager D-7000 for NT 4.0) using a Merck Eurolab column (LiChrospher 100, RP18, 10×250 mm) at a solvent flux of 6.0 mL/min. The solvent system used comprised components A (H₂O/0.1 vol. % TFA) and B (CH₃CN/0.1 vol. % TFA).

Equipment for producing the soluble peptides:

The peptides used for immobilisation were synthesised from C-terminal peptide amides using a "Syro" parallel automatic synthesis system (MultiSynTech, Witten, Germany) using the standard Fmoc protocol on Rink amide MBHA resin. After cleaving from the resin and separating all the protective groups all the peptides obtained were analysed using HPLC-MS and showed the desired molecular ion signals. After subsequent HPLC purification the peptides were lyophilised and stored at −20° C.

The peptides used for the immobilisation (13-mer peptides of the proteins MBP, casein, Histon H1) were produced automatically using the standard SPOT synthesis method using an Autospot AMS 222 (Abimed, Langenfeld, Germany) using Autospot XL Ver. 2.02 control software. The washing steps were carried out in stainless steel dishes (Merck Eurolab) which were moved on a tilting table.

EXAMPLES

Example 1

Maleinimido Functionalisation of Aminopropylsilylated Glass Surfaces 4-maleinimidobutyric acid (Fluka, 63183) was dissolved to 0.3M in DMF. The resultant mixture was activated by adding a half equivalent of di-iso-propyl carbodiimide (DIC) for 15 min at room temperature. Aminopropylsilylated glass surfaces purified with compressed air (2.5×7.5 cm; Sigma, Silane-Prep™, S4651) were coated with the maleinimidobutyric acid anhydride solution thus obtained and incubated for three hours at room temperature. The glass surfaces thus treated were then washed five times using respectively 30 mL of DMF for 3 minutes each at room temperature. After washing three times for three minutes each using respectively 30 mL of dichloromethane (DCM) at room temperature, the glass surfaces were dried and stored at 4° C. until further use.

Example 2

Maleinimido Functionalisation of Poly-lysine-modified Glass Surfaces 4-maleinimidocaproic acid (Fluka, 63176) was dissolved to 0.3M in DMF. The resultant mixture was activated by adding a half equivalent of DIC for 15 min at room temperature. Poly-lysine-modified glass surfaces purified with compressed air (Sigma, Poly-Prep™, P0425, 2.5×7.5 cm) were incubated with the maleinimidocaproic acid anhydride solution thus obtained for three hours at room temperature. In this case 60 µL of this solution was applied by capillary forces into the gap formed by two modified glass surfaces located one on top of the other. The glass surfaces thus treated were then washed five times using respectively 30 mL of DMF for 3 minutes each at room temperature. After washing three times for three minutes each using respectively 30 mL of DCM at room temperature, the glass surfaces were dried and stored at 4° C. until further use.

Example 3

Aldehyde Functionalisation of Aminopropylsilylated Glass Surfaces 4-carboxybenzaldehyde (Fluka, 21873) was dissolved to 0.3M in DMF. The resultant mixture was activated by adding a half equivalent of DIC for 15 min at room temperature. Aminopropylsilylated glass surfaces purified with compressed air (2.5×7.5 cm; Sigma, Silane-Prep™, S4651) were coated with the activated carboxybenzaldehyde solution thus obtained and incubated for three hours at room temperature. The glass surfaces thus treated were then washed five times using respectively 30 mL of DMF for 3 minutes each at room temperature. After washing three times for three minutes each using respectively 30 mL of DCM at room temperature, the glass surfaces were dried and stored at 4° C. until further use.

Example 4

Ketone Functionalisation of Aminopropylsilylated Glass Surfaces

Laevulinic acid (Fluka, 21873) was dissolved to 0.3M in DMF. The resultant mixture was activated by adding a half equivalent of DIC for 15 min at room temperature. Aminopropylsilylated glass surfaces purified with compressed air (2.5×7.5 cm; Sigma, Silane-Prep™, S4651) were coated with the laevulinic acid anhydride solution thus obtained and incubated for three hours at room temperature. The glass surfaces thus treated were then washed five times using respectively 30 mL of DML for 3 minutes each at room temperature. After washing three times for three minutes each using respectively 30 mL of DCM at room temperature, the glass surfaces were dried and stored at 4° C. until further use.

Example 5

Bromoacetylation of Aminopropylsilylated Glass Surfaces

Bromoacetic acid was dissolved to 0.4M in DMF. The resultant mixture was activated by adding a half equivalent of DIC for 15 min at room temperature. Aminopropylsilylated glass surfaces purified with compressed air (2.5×7.5 cm; Sigma, Silane-Prep™, S4651) were coated with the bromoacetic acid anhydride solution thus obtained and incubated for three hours at room temperature. The glass surfaces thus treated were then washed five times using respectively 30 mL of DMF for 3 minutes each at room temperature. After washing three times for three minutes each using respectively 30 mL of DCM at room temperature, the glass surfaces were dried and stored at 4° C. until further use.

Example 6

4-Bromomethyl Benzoic Acid Functionalisation of Aminopropylsilylated Glass Surfaces 4-bromomethyl benzoic acid was dissolved to 0.3M in DMF. The resultant mixture was activated by adding a half equivalent of DIC for 15 min at room temperature. Aminopropylsilylated glass surfaces purified with compressed air (2.5×7.5 cm; Sigma, Silane-Prep™, S4651) were coated with the 4-bromomethyl benzoic acid anhydride solution thus obtained and incubated for three hours at room temperature. The glass surfaces thus treated were then washed five times using respectively 30 mL of DMF for 3 minutes each at room temperature. After washing three times for three minutes each using respectively 30 mL of DCM at room temperature, the glass surfaces were dried and stored at 4° C. until further use.

Example 7

Phenylthiourea Functionalisation of Aminopropylsilylated Glass Surfaces

4-carboxyphenylthiourea (Lancaster, 13047) was dissolved to 0.2M in DMF. The resultant mixture was activated by adding a half equivalent of DIC for 15 min at room temperature. Aminopropylsilylated glass surfaces purified with compressed air (2.5×7.5 cm; Sigma, Silane-Prep™, S4651) were coated with the activated solution thus obtained and incubated for three hours at room temperature. The glass surfaces thus treated were then washed five times using respectively 30 mL of DMF for 3 minutes each at room temperature. After washing three times for three minutes each using respectively 30 mL of DCM at room temperature, the glass surfaces were dried and stored at 4° C. until further use.

Example 8

Thioamide Functionalisation of Aminopropylsilylated Glass Surfaces

Succinic acid-mono-thioamide was dissolved to 0.2M in DMF. The resultant mixture was activated by adding a half equivalent of DIC for 15 min at room temperature. Aminopropylsilylated glass surfaces purified with compressed air (2.5×7.5 cm; Sigma, Silane-Prep™, S4651) were coated with the modified succinic acid anhydride solution thus obtained and incubated for three hours at room temperature. The glass surfaces thus treated were then washed five times using respectively 30 mL of DMF for 3 minutes each at room temperature. After washing three times for three minutes each using respectively 30 mL of DCM at room temperature, the glass surfaces were dried and stored at 4° C. until further use.

Example 9

Bromoketone Functionalisation of Aminopropylsilylated Glass Surfaces

1,4-dibromo-2,3-diketobutane (Aldrich, D3,91609) was dissolved to 0.2M in DMF 0.1% triethylamine. Aminopropylsilylated glass surfaces purified with compressed air (2.5×7.5 cm; Sigma, Silane-Prep™, S4651) were coated with solution thus obtained and incubated for seven hours at room temperature. The glass surfaces thus treated were then washed five times using respectively 30 mL of DMF for 3 minutes each at room temperature. After washing three times for three minutes each using respectively 30 mL of DCM at room temperature, the glass surfaces were dried and stored at 4° C. until further use.

Example 10

Bromoketone Functionalisation of Thioamide-modified Glass Surfaces

The structures shown in this example can be used for simple surface modification with good yields.

Aminopropylsilylated glass surfaces reacted with succinic acid mono-thioamide (2.5×7.5 cm; Sigma, Silane-Prep™, S4651) (see Example 8) were coated with a 0.1M 1,4-dibromo-2,3-diketobutane solution (Aldrich, D3,916-9) in ethanol and incubated for three hours at room temperature. The glass surfaces thus treated were then washed five times using respectively 30 mL of ethanol for 3 minutes each at room temperature. After washing three times for three minutes each using respectively 30 mL of DCM at room temperature, the glass surfaces were dried and stored at 4° C. until further use.

Example 11

Bromoketone Functionalisation of Phenylthiourea-Modified Glass Surfaces

The structures shown in this example can be used for simple surface modification with good yields.

Aminopropylsilylated glass surfaces reacted with 4-carboxyphenylthiourea (2.5×7.5 cm; Sigma, Silane-Prep™, S4651) were coated with a 0.1M 1,4-dibromo-2,3-diketobutane solution in ethanol and incubated for three hours at room temperature. The glass surfaces thus treated were then washed five times using respectively 30 mL of ethanol for 3 minutes each at room temperature. After washing three times for three minutes each using respectively 30 mL of DCM at room temperature, the glass surfaces were dried and stored at 4° C. until further use.

Example 12

Bromopyroracemic Acid Functionalisation of Aminopropylsilylated Glass Surfaces

These surface modifications show that even very small structures can be used to convert an amino-functionalised glass surface to a bromoketone-functionalised one. In this case, bromopyroracemic acid is the smallest possible compound which contains both the carboxyl function required for the amide bond linkage and also the alpha-bromo-keto function required for the subsequent immobilisation of the biomolecule.

Sodium pyruvate was converted with oxalyl chloride into the corresponding acid chloride. Aminopropylsilylated glass surfaces purified with compressed air (2.5×7.5 cm; Sigma, Silane-Prep™, S4651) were coated with the solution thus obtained and incubated for five hours at room temperature. The glass surfaces thus treated were then washed five times using respectively 30 mL of DMF for 3 minutes each at room temperature. After washing three times for three minutes each using respectively 30 mL of methanol and DCM at room temperature, the glass surfaces were dried. The pyroracemic acid-modified glass surfaces thus obtained were converted into the bromopyroracemic-acid-modified glass surfaces by treating for one hour with a solution of 0.1 mL of bromine in glacial acetic acid. After washing three times for three minutes each using respectively 30 mL of methanol and DCM at room temperature, the glass surfaces were dried and stored at 4° C. until further use.

Example 13

Bromoacetophenone Functionalisation of Aminopropylsilylated Glass Surfaces

4-acetylbenzoic acid was dissolved to 0.3M in DMF. The resultant mixture was activated by adding a half equivalent of DIC for 15 min at room temperature. Aminopropylsilylated glass surfaces purified with compressed air (2.5×7.5 cm; Sigma, Silane-Prep™, S4651) were coated with the 4-acetylbenzoic acid anhydride solution thus obtained and incubated for three hours at room temperature. The glass surfaces thus treated were then washed five times using respectively 30 mL of DMF for 3 minutes each at room temperature. After washing three times for three minutes each using respectively 30 mL of methanol and DCM at room temperature, the glass surfaces were dried. The glass surfaces thus modified were converted into the bromoacetophenone-modified glass surfaces by treating for one hour with a solution of 0.1 mL of bromine in 10 mL of glacial acetic acid. After washing three times for three minutes each using respectively 30 mL of methanol and DCM at room temperature, the glass surfaces were dried and stored at 4° C. until further use.

Example 14

Thiocyanato-acetophenone Functionalisation of Aminopropylsilylated Glass Surfaces Bromoacetophenone-modified aminopropylsilylated glass surfaces (2.5×7.5 cm; Sigma, Silane-Prep™, S4651) (see Example 13) were coated with a 0.1M solution of sodium thiocyanate in ethanol and incubated for five hours at 50° C. The glass surfaces thus treated were then washed five times using respectively 30 mL of ethanol for 3 minutes each at room temperature. After washing three times for three minutes each using respectively 30 mL of DCM at room temperature, the glass surfaces were dried and stored at 4° C. until further use.

Example 15

Immobilisation of Cysteine-containing Peptides on Maleinimido-functionalised Glass Surfaces a) The peptides used for the immobilisation were synthesised by standard methods of Fmoc-based chemistry on the solid phase as C-terminal peptide amides. In this case, correspondingly protected Fmoc amino acids were activated with one equivalent HBTU and three equivalents diisopropylethylamine in DMF and coupled to Rink amide MBHA resin in DMF. Cleaving of the Fmoc protective group was carried out using 20% piperidine in DMF for 30 min at room temperature. Cleaving of the permanent protective groups (tBu for serine, threonine, tyrosine, glutaminic acid and asparaginic acid; Boc for lysine; trityl for asparagine, glutamine, cysteine, histidine and Pbf for arginine) and the simultaneous detachment from the polymer was carried out by treatment for two hours using 97% trifluoroacetic acid at room temperature. The resultant mixture was filtered and the filtrate was precipitated by adding tert-butyl methyl ether. The precipitate was separated and purified using HPLC on RP18 material using acetonitrile/water mixtures (0.1% trifluoroacetic acid). The fractions containing the desired product were lyophilised and stored at −20° C. until further use.

b) The HPLC-purified cysteine-containing peptides were dissolved in 200 mM sodium phosphate buffer pH 7.5 (final peptide concentration 10 mM). Then, respectively 1 µL of this solution was spotted onto the maleinimido-functionalised glass surfaces (see Example 1) at room temperature using an Eppendorf pipette and this was incubated for one hour at room temperature in an almost water-saturated atmosphere. After washing three times at room temperature using 100 mL of distilled water each time, the modified glass surfaces were incubated with 30 mL of a 300 mM solution of mercaptoethanol in 200 mM sodium phosphate buffer pH 7.5 to deactivate the residual maleinimido functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 16

Immobilisation of Cysteine-containing Peptides on Bromoacetylated Glass Surfaces The HPLC-purified cysteine-containing peptides were dissolved in 200 mM sodium phosphate buffer pH 6.5 (final peptide concentration 5 mM). Then, respectively 1 µL of this solution was spotted onto the functionalised glass surfaces (see Example 5) at room temperature using an Eppendorf pipette and this was incubated for one hour at room temperature in an almost water-saturated atmosphere. After washing three times at room temperature using 100 mL of distilled water each time, the modified glass surfaces were incubated with 30 mL of a 300 mM solution of mercaptoethanol in 200 mM sodium phosphate buffer pH 7.5 to deactivate the residual maleinimido functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 17

Immobilisation of Cysteine-containing Peptides on Aldehyde-functionalised Glass Surfaces The purified cysteine-containing peptides were dissolved in 200 mM sodium phosphate buffer pH 5.5 (final peptide concentration 5 mM) containing 200 mM tris-carboxyethyl phosphine. Then, respectively 1 µL of this solution was spotted onto the aldehyde-functionalised glass surfaces (see Example 3) at room temperature using an Eppendorf pipette and this was incubated for four hours at room temperature in an almost water-saturated atmosphere. After washing three times at room temperature using 100 mL of distilled water each time, the modified glass surfaces were incubated with 30 mL of a 40% aqueous. solution of hydroxylamine for 30 minutes at room temperature to deactivate the residual aldehyde functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 18

Immobilisation of Cysteine-containing Peptides on Maleinimido-functionalised Glass Surfaces a) The peptides used for the immobilisation (43 serine/threonine-containing peptides and the corresponding 43 control peptides) were synthesised by standard SPOT methods synthesis (R. Frank, *Tetrahedron*, 48, 1992, pp. 9217-9232; A. Kramer and J. Schneider-Mergener, Methods in Molecular Biology, vol. 87: Combinatorial Peptide Library Protocols, p. 25-39, edited by: S. Cabilly; Humana Press. Inc. Totowa, N.J.) on cellulose as C-terminal peptide amides. In this case, correspondingly protected Fmoc amino acid pentafluorophenyl esters were dissolved in DMF and 1 µL at a time was spotted on. The coupling reaction took place twice for 25 min at a time at room temperature. Cleaving of the Fmoc protective group was carried out using 20% piperidine in DMF for 20 min at room temperature. Cleaving of the permanent protective groups (tBu for serine, threonine, tyrosine, glutaminic acid and asparaginic acid; Boc for lysine; trityl for asparagine, glutamine, cysteine, histidine and Pbf for arginine) was carried out by treatment for two hours using 97% trifluoroacetic acid at room temperature. The cellulose-bound peptides were then washed with DCM, MeOH and diethylether and dried in vacuum. The peptides were cleaved from the cellulose using ammonia gas for 24 hours at room temperature. The spots with the physically adsorbed peptides were punched out and transferred to 96-well microtiter plates. After detaching the peptides using 200 µL of 20% methanol in each case under ultrasound conditions, the samples were filtered, transferred to 384-well microtiter plates, lyophilised and stored at −20° C. until further use. The following list gives an overview of the synthesised peptide sequences and at the same time allows the peptide numbers in FIGS. 8 and 9 to be assigned to the corresponding sequences (BAl=β-alanine).

```
 1 Cys-BA1-Lys-Lys-Ala-Leu-Arg-Arg-Gln-Glu-Thr-Val-Asp-Ala-Leu-NH2    [SEQ ID NO: 47]
 2 Cys-BA1-Lys-Lys-Ala-Leu-Arg-Arg-Gln-Glu-Ala-Val-Asp-Ala-Leu-NH2    [SEQ ID NO: 48]
 3 Cys-BA1-Ala-Lys-Arg-Arg-Arg-Leu-Ser-Ser-Leu-Arg-Ala-NH2            [SEQ ID NO: 49]
 4 Cys-BA1-Ala-Lys-Arg-Arg-Arg-Leu-Ala-Ala-Leu-Arg-AIa-NH2            [SEQ ID NO: 50]
 5 Cys-BA1-Gly-Arg-Thr-Gly-Arg-Arg-Asn-Ser-Ile-NH2                    [SEQ ID NO: 51]
 6 Cys-BA1-Gly-Arg-Ala-Gly-Arg-Arg-Asn-Ala-Ile-NH2                    [SEQ ID NO: 52]
 7 Cys-BA1-Asp-Asp-Asp-Glu-Glu-Ser-Ile-Thr-Arg-Arg-NH2                [SEQ ID NO: 53]
 8 Cys-BA1-Asp-Asp-Asp-Glu-Glu-Ala-Ile-Ala-Arg-Arg-NH2                [SEQ ID NO: 54]
 9 Cys-BA1-Glu-Arg-Ser-Pro-Ser-Pro-Ser-Phe-Arg-NH2                    [SEQ ID NO: 55]
10 Cys-BA1-Glu-Arg-Ala-Pro-Ala-Pro-Ala-Phe-Arg-NH2                    [SEQ ID NO: 56]
11 Cys-BA1-Gly-Arg-Pro-Arg-Thr-Ser-Ser-Phe-Ala-Glu-Gly-NH2            [SEQ ID NO: 57]
12 Cys-BA1-Gly-Arg-Pro-Arg-Ala-Ala-Ala-Phe-Ala-Gly-Gly-NH2            [SEQ ID NO: 58]
13 Cys-BA1-Lys-Lys-Lys-Ala-Leu-Ser-Arg-Gln-Leu-Ser-Val-Ala-Ala-NH2    [SEQ ID NO: 59]
14 Cys-BA1-Lys-Lys-Lys-Ala-Leu-Ala-Arg-Gln-Leu-Ala-Val-Ala-Ala-NH2    [SEQ ID NO: 60]
15 Cys-BA1-Lys-Lys-Leu-Asn-Arg-Thr-Leu-Ser-Val-Ala-NH2                [SEQ ID NO: 61]
16 Cys-BA1-Lys-Lys-Leu-Asn-Arg-Ala-Leu-Ala-Val-Ala-NH2                [SEQ ID NO: 62]
17 Cys-BA1-Lys-Arg-Gln-Gln-Ser-Phe-Asp-Leu-Phe-NH2                    [SEQ ID NO: 63]
18 Cys-BA1-Lys-Arg-Gln-Gln-Ala-Phe-Asp-Leu-Phe-NH2                    [SEQ ID NO: 64]
19 Cys-BA1-Lys-Arg-Arg-Glu-Ile-Leu-Ser-Arg-Arg-Pro-Ser-Tyr-Arg-NH2    [SEQ ID NO: 65]
20 Cys-BA1-Lys-Arg-Arg-Glu-Ile-Leu-Ala-Arg-Arg-Pro-Ala-Phe-Arg-NH2    [SEQ ID NO: 66]
21 Cys-BA1-Leu-Arg-Ala-Pro-Ser-Trp-Ile-Asp-Thr-NH2                    [SEQ ID NO: 67]
22 Cys-BA1-Leu-Arg-Ala-Pro-Ala-Trp-Ile-Asp-Ala-NH2                    [SEQ ID NO: 68]
23 Cys-BA1-Pro-Leu-Ser-Arg-Thr-Leu-Ser-Val-Ala-Ala-Lys-Lys-NH2        [SEQ ID NO: 69]
24 Cys-BA1-Pro-Leu-Ala-Arg-Ala-Leu-Ala-Val-Ala-Ala-Lys-Lys-NH2        [SEQ ID NO: 70]
25 Cys-BA1-Pro-Leu-Ser-Arg-Thr-Leu-Ser-Val-Ser-Ser-NH2                [SEQ ID NO: 71]
26 Cys-BA1-Pro-Leu-Ala-Arg-Ala-Leu-    Ala-Val-Ala-Ala-NH2            [SEQ ID NO: 72]
27 Cys-BA1-Gln-Lys-Arg-Pro-Ser-Gln-Arg-Ser-Lys-Tyr-Leu-NH2            [SEQ ID NO: 73]
28 Cys-BA1-Gln-Lys-Arg-Pro-Ala-Gln-Arg-Ala-Lys-Phe-Leu-NH2            [SEQ ID NO: 74]
29 Cys-BA1-Arg-Lys-Ile-Ser-Ala-Ser-Glu-Phe-NH2                        [SEQ ID NO: 75]
30 Cys-BA1-Arg-Lys-Ile-Ala-Ala-Ala-Glu-Phe-NH2                        [SEQ ID NO: 76]
31 Pro-Lys-Thr-Pro-Lys-Lys-Ala-Lys-Lys-Leu-BA1-Cys-NH2                [SEQ ID NO: 77]
32 Pro-Lys-Ala-Pro-Lys-Lys-Ala-Lys-Lys-Leu-BA1-Cys-NH2                [SEQ ID NO: 78]
33 Cys-BA1-Arg-Pro-Arg-Ala-Ala-Thr-Phe-NH2                            [SEQ ID NO: 79]
34 Cys-BA1-Arg-Pro-Arg-Ala-Ala-Ala-Phe-NH2                            [SEQ ID NO: 80]
35 Cys-BA1-Arg-Arg-Arg-Ala-Pro-Leu-Ser-Pro-NH2                        [SEQ ID NO: 81]
36 Cys-BA1-Arg-Arg-Arg-Ala-Pro-Leu-Ala-Pro-NH2                        [SEQ ID NO: 82]
37 Cys-BA1-Arg-Arg-Arg-Glu-Glu-Glu-Thr-Glu-Glu-Glu-NH2                [SEQ ID NO: 83]
38 Cys-BA1-Arg-Arg-Arg-Glu-Glu-Glu-Ala-Glu-Glu-Glu-NH2                [SEQ ID NO: 84]
39 Cys-BA1-Met-His-Arg-Gln-Glu-Thr-Val-Asp-Cys-Leu-Lys-NH2            [SEQ ID NO: 85]
40 Cys-BA1-Met-His-Arg-Gln-Glu-Ala-Val-Asp-Cys-Leu-Lys-NH2            [SEQ ID NO: 86]
41 Cys-BA1-Lys-Lys-Arg-Phe-Ser-Phe-Lys-Lys-Ser-Phe-Lys-Leu-NH2        [SEQ ID NO: 87]
42 Cys-BA1-Lys-Lys-Arg-Phe-Ala-Phe-Lys-Lys-Ala-Phe-Lys-Leu-NH2        [SEQ ID NO: 88]
43 Cys-BA1-Pro-Lys-Asp-Pro-Ser-Gln-Arg-Arg-Arg-NH2                    [SEQ ID NO: 89]
44 Cys-BA1-Pro-Lys-Asp-Pro-Ala-Gln-Arg-Arg-Arg-NH2                    [SEQ ID NO: 90]
45 Cys-BA1-Ile-Ala-Ala-Asp-Ser-Glu-Ala-Glu-Gln-NH2                    [SEQ ID NO: 91]
46 Cys-BA1-Ile-Ala-Ala-Asp-Ala-Glu-Ala-Glu-Gln-NH2                    [SEQ ID NO: 92]
47 Cys-BA1-Ser-Pro-Ala-Leu-Thr-Gly-Asp-Glu-Ala-NH2                    [SEQ ID NO: 93]
48 Cys-BA1-Ala-Pro-Ala-Leu-Ala-Gly-Asp-Glu-Ala-NH2                    [SEQ ID NO: 94]
49 Cys-BA1-Gly-Arg-Ile-Leu-Thr-Leu-Pro-Arg-Ser-NH2                    [SEQ ID NO: 95]
50 Cys-BA1-Gly-Arg-Ile-Leu-Ala-Leu-Pro-Arg-Ala-NH2                    [SEQ ID NO: 96]
51 Cys-BA1-Met-Gly-Glu-Ala-Ser-Gly-Cys-Gln-Leu-NH2                    [SEQ ID NO: 97]
52 Cys-BA1-Met-Gly-Glu-Ala-Ala-Gly-Cys-Gln-Leu-NH2                    [SEQ ID NO: 98]
53 Cys-BA1-Glu-Glu-Thr-Pro-Tyr-Ser-Tyr-Pro-Thr-NH2                    [SEQ ID NO: 99]
54 Cys-BA1-Gly-Glu-Ala-Pro-Phe-Ser-Phe-Pro-Ala-NH2                    [SEQ ID NO: 100]
55 Cys-BA1-Gly-Asn-His-Thr-Tyr-Gln-Glu-Ile-Ala-NH2                    [SEQ ID NO: 101]
56 Cys-BA1-Gly-Asn-His-Ala-Phe-Gln-Glu-Ile-Ana-NH2                    [SEQ ID NO: 102]
57 Leu-Arg-Ser-Pro-Ser-Trp-Glu-Pro-Phe-BA1-Cys-NH2                    [SEQ ID NO: 103]
58 Leu-Arg-Ala-Pro-Ala-Trp-Glu-Pro-    Phe-BA1-Cys-NH2                [SEQ ID NO: 104]
59 Ser-Ser-Pro-Val-Tyr-Gln-Asp-Ala-Val-BA1-Cys-NH2                    [SEQ ID NO: 105]
60 Ala-Ala-Pro-Val-Phe-Gln-Asp-Ala-Val-BA1-Cys-NH2                    [SEQ ID NO: 106]
61 Cys-BA1-Ser-Arg-Thr-Leu-Ser-Val-Ser-Ser-Leu-NH2                    [SEQ ID NO: 107]
62 Cys-BA1-Ala-Arg-Ala-Leu-Ala-Val-Ala-Ala-Leu-NH2                    [SEQ ID NO: 108]
63 Leu-Ser-Val-Ser-Ser-Leu-Pro-Gly-Leu-BA1-Cys-NH2                    [SEQ ID NO: 109]
64 Leu-Ser-Val-Ala-Ala-Leu-Pro-Gly-Leu-BA1-Cys-NH2                    [SEQ ID NO: 110]
65 Cys-BA1-Val-Thr-Pro-Arg-Thr-Pro-Pro-Pro-Ser-NH2                    [SEQ ID NO: 111]
66 Cys-BA1-Val-Ala-Pro-Arg-Ala-Pro-Pro-Pro-Ala-NH2                    [SEQ ID NO: 112]
```

-continued

| | | |
|---|---|---|
| 67 | Cys-BA1-Arg-Phe-Ala-Arg-Lys-Gly-Ser-Leu-Arg-Gln-Lys-Asn-Val-NH$_2$ | [SEQ ID NO: 113] |
| 68 | Cys-BA1-Arg-Phe-Ala-Arg-Lys-Gly-Ala-Leu-Arg-Gln-Lys-Asn-Val-NH$_2$ | [SEQ ID NO: 114] |
| 69 | Cys-BA1-Pro-Arg-Pro-Ala-Ser-Val-Pro-Pro-Ser-NH$_2$ | [SEQ ID NO: 115] |
| 70 | Cys-BA1-Pro-Arg-Pro-Ala-Ser-Ala-Val-Pro-Pro-Ala-NH$_2$ | [SEQ ID NO: 116] |
| 71 | Cys-BA1-Arg-Glu-Ala-Arg-Ser-Arg-Ala-Ser-Thr-NH$_2$ | [SEQ ID NO: 117] |
| 72 | Cys-BA1-Arg-Glu-Ala-Arg-Ala-Arg-Ala-Ala-Ala-NH$_2$ | [SEQ ID NO: 118] |
| 73 | Gln-Ser-Tyr-Ser-Ser-Ser-Gln-Arg-Val-BA1-Cys-NH$_2$ | [SEQ ID NO: 119] |
| 74 | Gln-Ser-Tyr-Ala-Ala-Ala-Gln-Arg-Val-BA1-Cys-NH$_2$ | [SEQ ID NO: 120] |
| 75 | Cys-BA1-Gly-Gly-Gly-Thr-Ser-Pro-Val-Phe-Pro-NH$_2$ | [SEQ ID NO: 121] |
| 76 | Cys-BA1-Gly-Gly-Gly-Ala-Ala-Pro-Val-Phe-Pro-NH$_2$ | [SEQ ID NO: 122] |
| 77 | Leu-Tyr-Ser-Ser-Ser-Pro-Gly-Gly-Ala-BA1-Cys-NH$_2$ | [SEQ ID NO: 123] |
| 78 | Leu-Tyr-Ala-Ala-Ala-Pro-Gly-Gly-Ala-BA1-Cys-NH$_2$ | [SEQ ID NO: 124] |
| 79 | Cys-BA1-Asp-Leu-Pro-Leu-Ser-Pro-Ser-Ala-Phe-NH$_2$ | [SEQ ID NO: 125] |
| 80 | Cys-BA1-Asp-Leu-Pro-Leu-Ala-Pro-Ala-Ala-Phe-NH$_2$ | [SEQ ID NO: 126] |
| 81 | Cys-BA1-Thr-Thr-Pro-Leu-Ser-Pro-Thr-Arg-Leu-NH$_2$ | [SEQ ID NO: 127] |
| 82 | Cys-BA1-Ala-Ala-Pro-Leu-Ala-Pro-Ala-Arg-Leu-NH$_2$ | [SEQ ID NO: 128] |
| 83 | Arg-Arg-Ile-Ser-Lys-Asp-Asn-Pro-Asp-Tyr-Gln-Gln-Asp-BA1-Cys-NH$_2$ | [SEQ ID NO: 129] |
| 84 | Arg-Arg-Ile-Ala-Lys-Asp-Asn-Pro-Asp-Tyr-Gln-Gln-Asp-BA1-Cys-NH$_2$ | [SEQ ID NO: 130] |
| 85 | Cys-BA1-Leu-Arg-Arg-Ala-Ser-Leu-Gly-NH$_2$ | [SEQ ID NO: 131] |
| 86 | Cys-BA1-Leu-Arg-Arg-Ala-Ala-Leu-Gly-NH$_2$ | [SEQ ID NO: 132] | b) The cysteine-containing peptides in the microtiter plates were applied to the maleinimido-functionalised glass surfaces (see Example 1) by using a NanoPlotter from Gesim. The spot-to-spot distance was 1 mm. 0.8 nL of a peptide solution in 100 mM PBS buffer pH 7.8 containing 20% glycerin was applied per spot and this assembly was incubated for four hours at room temperature. After washing three times at room temperature using 100 mL of distilled water each time, the modified glass surfaces were incubated with 30 mL of a 300 mM solution of mercaptoethanol in 200 mM phosphate buffer pH 7.5 to deactivate the residual maleinimido functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 19

Immobilisation of Anthraniloyl Peptides on Aldehyde-functionalised Glass Surfaces a) The peptides used for the immobilisation (in each case 13-mer peptides representing the total primary structure of the proteins MBP, casein and histon H1) were synthesised by standard SPOT methods synthesis (R. Frank, *Tetrahedron*, 48, 1992, pp. 9217-9232; A. Kramer and J. Schneider-Mergener, Methods in Molecular Biology, vol. 87: Combinatorial Peptide Library Protocols, p. 25-39, edited by: S. Cabilly; Humana Press. Inc. Totowa, N.J.) on cellulose as C-terminal peptide amides. In this case, correspondingly protected Fmoc amino acid pentafluorophenyl esters were dissolved in DMF and 1 µL at a time was spotted on. The coupling reaction took place twice for 25 min at a time at room temperature. Cleaving of the Fmoc protective group was carried out using 20% piperidine in DMF for 20 min at room temperature. After the last Fmoc cleaving the N-termini of the cellulose-bound peptides were converted into the corresponding 2-aminobenzoylated derivatives by incubation for five hours at 50° C. using a saturated solution of Isatur acid in DMF. Cleaving of the permanent protective groups (tBu for serine, threonine, tyrosine, glutaminic acid and asparaginic acid; Boc for lysine; trityl for asparagine, glutamine, cysteine, histidine and Pbf for arginine) was carried out by treatment for two hours using 97% trifluoroacetic acid at room temperature. The cellulose-bound peptides were then washed with DCM, MeOH and diethylether and dried in vacuum. The peptides were cleaved from the cellulose using ammonia gas for 24 hours at room temperature. The spots with the physically adsorbed peptides were punched out and transferred to 96-well microtiter plates. After detaching the peptides using 200 µL of 20% methanol in each case under ultrasound conditions, the samples were filtered, transferred to 384-well microtiter plates, lyophilised and stored at −20° C. until further use.

b) The anthraniloyl peptides in the microtiter plates were dissolved in 200 mM sodium phosphate buffer pH 6.0 (final peptide concentration 0.5 mM) containing 15% DMSO. Then 0.01 µL of this solution at a time was applied to the aldehyde-modified glass surfaces (see Example 3) at room temperature using a NanoPlotter from Gesim and this was incubated for four hours at room temperature. After washing three times at room temperature using 100 mL of distilled water each time, the modified glass surfaces were incubated with 30 mL of 40% aqueous solution of hydroxylamine for 30 minutes at room temperature to deactivate the residual aldehyde functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 20

Immobilisation of Amino-oxyacetic-acid Containing Peptides on Aldehyde-functionalised Glass Surfaces a) The peptides used for the immobilisation (in each case 13-mer peptides representing the total primary structure of the proteins MBP, casein and histon H1) were synthesised by standard SPOT methods synthesis (R. Frank, *Tetrahedron*, 48, 1992, pp. 9217-9232; A. Kramer and J. Schneider-Mergener, Methods in Molecular Biology, vol. 87: Combinatorial Peptide Library Protocols, p. 25-39, edited by: S. Cabilly; Humana Press. Inc. Totowa, N.J.) on cellulose as C-terminal peptide amides. In this case, correspondingly protected Fmoc amino acid pentafluorophenyl esters were dissolved in DMF and 1 µL at a time was spotted on. The coupling reaction took place twice for 25 min at a time at room temperature. Cleaving of the Fmoc protective group was carried out using 20% piperidine in DMF for 20 min at room temperature. The N-terminus was acylated using Boc-amino-oxy-acetic acid. For this purpose this was activated in DMF using 1 equivalent HOAT/DIC. In each case 1 µL of this mixture was spotted onto each cellulose-bound peptide and left for 30 min at room temperature. Cleaving of the permanent protective groups (tBu for serine, threonine, tyrosine, glutaminic acid and asparaginic acid; Boc for lysine; trityl for asparagine, glutamine, cysteine, histidine and Pbf for arginine) was carried out by treatment for two hours using 97% trifluoroacetic acid at room temperature. The cellulose-bound peptides were then washed with DCM, MeOH and diethylether and dried in vacuum. The peptides were cleaved from the cellulose using ammonia gas for 24 hours at room temperature. The spots with the physically adsorbed peptides were punched out and transferred to 96-well microtiter plates. After detaching the peptides using 200 µL of 20% methanol in each case under ultrasound conditions, the samples were filtered, transferred to 384-well microtiter plates, lyophilised and stored at −20° C. until further use.

b) The amino-oxy-acetic acid-containing peptides in the microtiter plates were dissolved in DMSO. Then 1 nL of this solution at a time was applied to the aldehyde-functionalised glass surfaces (see Example 3) at room temperature using a NanoPlotter from Gesim and this was incubated for four hours at room temperature. In this case, the spot-to-spot distance was 1.5 mm. After washing three times at room temperature using 100 mL of distilled water each time, the modified glass surfaces were incubated with 30 mL of a 40% aqueous solution of hydroxylamine for 30 minutes at room temperature to deactivate the residual aldehyde functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 21

Immobilisation of Amino-oxyacetic-acid Containing Peptides on Bromo-acetylated Glass Surfaces a) The peptides used for the immobilisation (in each case 13-mer peptides representing the total primary structure of the proteins MBP, casein and histon H1) were synthesised by standard SPOT methods synthesis (R. Frank, *Tetrahedron*, 48, 1992, pp. 9217-9232; A. Kramer and J. Schneider-Mergener, Methods in Molecular Biology, vol. 87: Combinatorial Peptide Library Protocols, p. 25-39, edited by: S. Cabilly; Humana Press. Inc. Totowa, N.J.) on cellulose as C-terminal peptide amides. In this case, correspondingly protected Fmoc amino acid pentafluorophenyl esters were dissolved in DMF and 1 µL at a time was spotted on. The coupling reaction took place twice for 25 min at a time at room temperature. Cleaving of the Fmoc protective group was carried out using 20% piperidine in DMF for 20 min at room temperature. The N-terminus was acylated using Boc-amino-oxy-acetic acid. For this purpose this was activated in DMF using 1 equivalent HOAT/DIC. In each case 1 µL of this mixture was spotted onto each cellulose-bound peptide and left for 30 min at room temperature. Cleaving of the permanent protective groups (tBu for serine, threonine, tyrosine, glutaminic acid and asparaginic acid; Boc for lysine; trityl for asparagine, glutamine, cysteine, histidine and Pbf for arginine) was carried out by treatment for two hours using 97% trifluoroacetic acid at room temperature. The cellulose-bound peptides were then washed with DCM, MeOH and diethylether and dried in vacuum. The peptides were cleaved from the cellulose using ammonia gas for 24 hours at room temperature. The spots with the physically adsorbed peptides were punched out and transferred to 96-well microtiter plates. After detaching the peptides using 200 µL of 20% methanol in each case under ultrasound conditions, the samples were filtered, transferred to 384-well microtiter plates, lyophilised and stored at −20° C. until further use.

b) The amino-oxy-acetic acid-containing peptides in the microtiter plates were dissolved in 200 mM sodium phosphate buffer pH 6.0 (final peptide concentration 0.5 mM) containing 25 vol. % glycerin. Then 0.01 µL of this solution at a time was applied to the bromo-acetylated, amino-functionalised glass surfaces (see Example 5) at room temperature using a NanoPlotter from Gesim and this was incubated for four hours at room temperature. After washing three times at room temperature using 100 mL of distilled water each time, the modified glass surfaces were incubated with 30 mL of a 300 mM solution of mercaptoethanol in 200 mM sodium phosphate buffer pH 7.5 to deactivate the residual bromo-acetyl functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 22

Immobilisation of Amino-oxyacetic-Acid Containing Peptides on Aldehyde-functionalised Glass Surfaces a) The peptide used for the immobilisation, Dpr(Aoa)-Leu-Arg-Arg-Ala-Ser-Leu-Gly-NH$_2$ was synthesised by standard methods of Fmoc-based chemistry on the solid phase as C-terminal peptide amide. In this case, correspondingly protected Fmoc amino acids were activated with one equivalent HBTU and three equivalents diisopropylethyl amine in DMF and coupled to Rink amide MBHA resin in DMF. Cleaving of the Fmoc protective group was carried out using 20% piperidine in DMF for 30 min at room temperature. Cleaving of the permanent protective groups (tBu for serine, Boc for the amino-oxy function and Pbf for arginine) and simultaneous detachment from the polymer was carried out by treatment for two hours using 97% trifluoroacetic acid at room temperature. The resulting mixture was filtered and the filtrate was precipitated by adding tert-butyl methyl ether. The precipitate was separated and purified by means of HPLC on RP18 material using acetonitrile/water mixtures (0.1% trifluoroacetic acid). The fractions containing the desired product were lyophilised and stored at −20° C. until further use.

b) The peptide Dpr(Aoa)-Leu-Arg-Arg-Ala-Ser-Leu-Gly-NH$_2$ was dissolved in 200 mM acetate buffer pH 4.0 (final peptide concentration 0.5 mM) containing 25 vol. % tert-butanol. Then 5 nL of this solution at a time was applied to the aldehyde-functionalised glass surfaces (Telechem/ArrayIt, CSS-25 glass support) in an assembly of 20 rows and 48 gaps (a total of 960 spots) at room temperature using a NanoPlotter from Gesim. In this case, the spot-to-spot distance was 1 mm. The glass surfaces thus treated were then incubated for four hours at room temperature. After washing three times at room temperature using 100 mL of distilled water each time, the modified glass surfaces were incubated with 30 mL of a 40% aqueous solution of hydroxyl amine 30 min at room temperature to deactivate the residual aldehyde functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 23

Immobilisation of Cysteine-containing Peptides on 4-bromomethylbenzoylated Glass Surfaces The HPLC-purified peptide Cys-βAla-Leu-Arg-Arg-Ala-Ser-Leu-Gly-NH$_2$ was dissolved in 200 mM sodium phosphate buffer pH 6.5 (final peptide concentration 2 mM) containing 20 vol. % glycerin. Then 2 nL of this solution at a time was applied to the bromomethylbenzoic-acid-functionalised glass surfaces (see Example 6) in an assembly of 50 rows and 120 gaps (a total of 6000 spots) at room temperature using a NanoPlotter from Gesim. In this case, the spot-to-spot distance was 0.4 mm. The glass surfaces thus treated were then incubated for five hours at room temperature. After washing three times at room temperature using 100 mL of distilled water each time, the modified glass surfaces were incubated with 30 mL of a 300 mM solution of mercaptoethanol in 200 mM sodium phosphate buffer pH 7.5 to deactivate the residual bromomethyl phenyl functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 24

Immobilisation of Thioamide-containing Peptides on 1-bromo-2,3-diketo-butane-functionalised Glass Surfaces a) The peptide used for the immobilisation, Leu-Arg-Arg-Ala-Ser-Leu-Gly-thioamide was synthesised by standard methods of Fmoc-based chemistry on the solid phase as C-terminal peptide amide. Fmoc-Gly-OH bound to Rink amide MBHA resin was boiled under reflux for 3 hours using Lawessons reagent. The resin was then washed with THF and DCM, agitated for 1 hour with DMF and then washed with DMF, DCM and methanol. After removing the Fmoc protective group using 50% Morpholine in DMF (40 min), the correspondingly protected Fmoc amino acids were activated with one equivalent HBTU and three equivalents diisopropylethyl amine in DMF and coupled. Cleaving of the Fmoc protective group was carried out using 20% piperidine in DMF for 30 min at room temperature. Cleaving of the permanent protective groups (tBu for serine, Pbf for arginine) and simultaneous detachment from the polymer was carried out by treatment for two hours using 97% trifluoroacetic acid at room temperature. The resulting mixture was filtered and the filtrate was precipitated by adding tert-butyl methyl ether. The precipitate was separated and purified by means of HPLC on RP18 material using acetonitrile/water mixtures (0.1% trifluoroacetic acid). The fractions containing the desired product were lyophilised and stored at −20° C. until further use.

b) The peptide Leu-Arg-Arg-Ala-Ser-Leu-Gly-thioamide was dissolved in 200 mM sodium phosphate buffer pH 5.5 (final concentration 1 mM) containing 50 vol. % glycerin. Then 1 nL of this solution at a time was applied to the 1-bromo-2,3-diketo-butane-functionalised glass surfaces (see Example 10) in an assembly of 70 rows and 168 gaps (a total of 11760 spots) at room temperature using a NanoPlotter from Gesim. In this case, the spot-to-spot distance was 0.3 mm. The glass surfaces thus treated were then microwave-treated for 2 min and then incubated for three hours at room temperature. After washing three times at room temperature using 100 mL of distilled water each time, the modified glass surfaces were incubated with 30 mL of a 3% aqueous solution of thioacetamide for 30 min at room temperature to deactivate the residual α-bromo-ketone functions. The glass surfaces were then washed five times for 3 minutes at a time using respectively 50 mL of water at room temperature and then washed twice for 3 minutes at a time using respectively 50 mL of methanol at room temperature. The glass surfaces thus treated were dried and stored at 4° C. until further use.

Example 25

Analysis of Kinase-mediated Peptide Modifications on Modified Glass Surfaces (See FIG. 4)

A glass surface (maleinimido-functionalised glass surface, see Example 1) modified with the peptide Cys-βAla-Leu-Arg-Arg-Ala-Ser-Leu-Gly-NH$_2$ (both as the raw peptide and as a peptide purified by means of prep. HPLC) and the control peptide Cys-βAla-Leu-Arg-Arg-Ala-Ala-Leu-Gly-NH$_2$ was incubated with 10 mL of 100 μM ATP in kinase buffer (50mM tris-HCl, 150 mM NaCl, 30 mM MgCl$_2$, 4 mM DTT, 2 mM EGTA, pH 7.5) for 10 minutes at room temperature. Then 1 μL of a mixture of protein kinase A (Sigma, P26452, U/mL), 100 μM/mL ATP and 100 μCi/mL γ-$^{32}$P-ATP (Amersham, 9.25 mBq/250 μCi/25 μL, activity>5000 Ci/mmol) in kinase buffer (50 mM tris-HCl, 150 mM NaCl, 30 mM MgCl$_2$, 4 mM DTT, 2 mM EGTA, pH 7.5) was spotted onto the peptide-modified glass surfaces and incubated for 30 min at room temperature in an almost water-saturated atmosphere. In order to reduce the background caused by the non-specific binding of ATP or kinase molecules to the glass surfaces, the modified glass surfaces were washed as follows:
- three times for 3 minutes at room temperature using washing buffer (1% SDS and 1% Tween20 in 50 mM TRIS buffer, pH 7.5, 200 mM NaCl)
- twice for 3 minutes at room temperature using 1M NaCl solution
- twice for 3 minutes at room temperature using distilled water
- twice for 3 minutes at room temperature using 80% formic acid in ethanol
- twice for 3 minutes at room temperature using distilled water
- twice for 5 minutes at 50° C. using a solution containing 6M urea, 2M thiourea and 1% SDS
- three times for 3 minutes at room temperature using distilled water
- three times for 3 minutes at room temperature using methanol After drying the glass surface the quantity of radioactive phosphate incorporated in the glass-surface-bound peptides was determined using a PhosphorImager system (FLA-3000, FUJIFILM) (see FIG. 4).

Example 26

Analysis of Kinase-mediated Peptide Modifications on Modified Glass Surfaces (See FIG. 5)

A glass surface (maleinimido-functionalised glass surface, see Example 1) modified with the peptide Cys-βAla-Leu-Arg-Arg-Ala-Ser-Leu-Gly-NH$_2$ and the control peptide Cys-βAla-Leu-Arg-Arg-Ala-Ala-Leu-Gly-NH$_2$ was incubated with 10 mL of 100 μM ATP in kinase buffer (50 mM tris-HCl, 150 mM NaCl, 30 mM MgCl$_2$, 4 mM DTT, 2 mM EGTA, pH 7.5) for 10 minutes at room temperature. The glass surface was dried and a cover glass was then placed on the peptide-modified glass surface. Then 20 μL of a mixture of protein kinase A (Sigma, P26452, U/mL), 100 μM/mL ATP and 100 μCi/mL γ-$^{32}$P-ATP (Amersham, 9.25 mBq/250 μCi/25 μL, activity>5000 Ci/mmol) in kinase buffer (50 mM tris-HCl, 150 mM NaCl, 30 mM MgCl$_2$, 4mM DTT, 2 mM EGTA, pH 7.5) was applied by capillary forces into the gap formed by the cover glass lying on the modified glass surface. Incubation was then carried out for 30 min at room temperature in an almost water-saturated atmosphere. In order to reduce the background caused by the non-specific binding of ATP or kinase molecules to the glass surfaces, the modified glass surfaces were washed as follows:

- three times for 3 minutes at room temperature using washing buffer (1% SDS and 1% Tween20 in 50 mM TRIS buffer, pH 7.5, 200 mM NaCl)
- twice for 3 minutes at room temperature using 1M NaCl solution
- twice for 3 minutes at room temperature using distilled water
- twice for 3 minutes at room temperature using 80% formic acid in ethanol
- twice for 3 minutes at room temperature using distilled water
- twice for 5 minutes at 50° C. using a solution containing 6M urea, 2M thiourea and 1% SDS
- three times for 3 minutes at room temperature using distilled water
- three times for 3 minutes at room temperature using methanol After drying the glass surface the quantity of radioactive phosphate incorporated in the glass-surface-bound peptides was determined using a PhosphorImager system (FLA-3000, FUJIFILM) (see FIG. 5).

Example 27

Analysis of Kinase-mediated Peptide Modifications on Modified Glass Surfaces (See FIG. 7)

A glass surface modified with the peptide Dpr(Aoa)-Leu-Arg-Arg-Ala-Ser-Leu-Gly-NH$_2$ (see Example 22) was incubated with 10 mL of 100 μM ATP in kinase buffer (50 mM tris-HCl, 150 mM NaCl, 30 mM MgCl$_2$, 4 mM DTT, 2 mM EGTA, pH 7.5) for 10 minutes at room temperature. The glass surface was dried and a second unmodified glass surface of the same dimensions was then placed on the peptide-modified glass surface. Then 50 μL of a mixture of protein kinase A (Sigma, P26452, U/mL), 100 μM/mL ATP and 100 μCi/mL γ-$^{32}$P-ATP (Amersham, 9.25 mBq/250 μCi/25 μL, activity>5000 Ci/mmol) in kinase buffer (50 mM tris-HCl, 150 mM NaCl, 30 mM MgCl$_2$, 4 mM DTT, 2 mM EGTA, pH 7.5) was applied by capillary forces into the gap formed by the second glass surface lying on the modified glass surface. Incubation was then carried out for 30 min at room temperature in an almost water-saturated atmosphere. In order to reduce the background caused by the non-specific binding of ATP or kinase molecules to the glass surfaces, the modified glass surface was washed as follows:

- three times for 3 minutes at room temperature using washing buffer (1% SDS and 1% Tween20 in 50 mM TRIS buffer, pH 7.5, 200 mM NaCl)
- twice for 3 minutes at room temperature using 1M NaCl solution
- twice for 3 minutes at room temperature using distilled water
- twice for 3 minutes at room temperature using 80% formic acid in ethanol
- twice for 3 minutes at room temperature using distilled water
- twice for 5 minutes at 50° C. using a solution containing 6M urea, 2M thiourea and 1% SDS
- three times for 3 minutes at room temperature using distilled water
- three times for 3 minutes at room temperature using methanol After drying the glass surface the quantity of radioactive phosphate incorporated in the glass-surface-bound peptides was determined using a PhosphorImager system (FLA-3000, FUJIFILM) (see FIG. 7).

Example 28

Analysis of Kinase-mediated Peptide Modifications on Modified Glass Surfaces (See FIG. 6)

A glass surface modified with the peptide Leu-Arg-Arg-Ala-Ser-Leu-Gly-thioamide (see Example 24) was incubated with 10 mL of 100 μM ATP in kinase buffer (50 mM tris-HCl, 150 mM NaCl, 30 mM MgCl$_2$, 4 mM DTT, 2 mM EGTA, pH 7.5) for 10 minutes at room temperature. The glass surface was dried and a second unmodified glass surface of the same dimensions was then placed on the peptide-modified glass surface. Then 50 μL of a mixture of protein kinase A (Sigma, P26452, U/mL), 100 μM/mL ATP and 100 μCi/mL γ-$^{32}$P-ATP (Amersham, 9.25 mBq/250 μCi/25 μL, activity>5000 Ci/mmol) in kinase buffer (50 mM tris-HCl, 150 mM NaCl, 30 mM MgCl$_2$, 4 mM DTT, 2 mM EGTA, pH 7.5) was applied by capillary forces into the gap formed by the second glass surface lying on the modified glass surface. Incubation was then carried out for 30 min at room temperature in an almost water-saturated atmosphere. In order to reduce the background caused by the non-specific binding of ATP or kinase molecules to the glass surfaces, the modified glass surface was washed as follows:

- three times for 3 minutes at room temperature using washing buffer (1% SDS and 1% Tween20 in 50 mM TRIS buffer, pH 7.5, 200 mM NaCl)
- twice for 3 minutes at room temperature using 1M NaCl solution
- twice for 3 minutes at room temperature using distilled water
- twice for 3 minutes at room temperature using 80% formic acid in ethanol
- twice for 3 minutes at room temperature using distilled water
- twice for 5 minutes at 50° C. using a solution containing 6M urea, 2M thiourea and 1% SDS
- three times for 3 minutes at room temperature using distilled water
- three times for 3 minutes at room temperature using methanol After drying the glass surface the quantity of radioactive phosphate incorporated in the glass-surface-bound peptides was determined using a PhosphorImager system (FLA-3000, FUJIFILM) (see FIG. 6).

Example 29

Analysis of Kinase-mediated Peptide Modifications on Modified Glass Surfaces (see FIG. 1)

A glass surface (maleinimido-functionalised glass surface, see Example 2) modified with the peptides Cys-βAla-Leu-Arg-Arg-Ala-Ser-Leu-Gly-NH$_2$, Cys-βAla-Gln-Lys-Arg-Pro-Ser-Gln-Arg-Ser-Lys-NH$_2$ and Cys-βAla-Arg-Arg-Lys-Asp-Leu-His-Ap-Arg-Glu-Glu-Asp-Glu-Ala-Met-Ser-Ile-Thr-Ala-NH$_2$ or the corresponding control peptides Cys-βAla-Leu-Arg-Arg-Ala-Ala-Leu-Gly-NH$_2$, Cys-βAla-Gln-Lys-Arg-Pro-Ala-Gln-Arg-Ala-Lys-NH$_2$ and Cys-βAla-Arg-Arg-Lys-Asp-Leu-His-Asp-Asp-Glu-Glu-Asp-Glu-Ala-Met-Ala-Ile-Ala-Ala-NH$_2$ (see Example 22) was incubated with 10 mL of 100 µM ATP in kinase buffer (50 mM tris-HCl, 150 mM NaCl, 30 mM MgCl$_2$, 4 mM DTT, 2 mM EGTA, pH 7.5) for 10 minutes at room temperature. Then, 1 µL of a mixture of protein kinase A (Protein kinase A, Sigma, P2645, 1.67 µg/mL for Cys-βAla-Leu-Arg-Arg-Ala-Ser-Leu-Gly-NH$_2$ and Cys-βAla-Leu-Arg-Arg-Ala-Ala-Leu-Gly-NH$_2$, Protein kinase C, Sigma, P7956, 1.3 pg/mL for Cys-βAla-Gln-Lys-Arg-Pro-Ser-Gln-Arg-Ser-Lys-NH$_2$ and Cys-βAla-Gln-Lys-Arg-Pro-Ala-Gln-Arg-Ala-Lys-NH$_2$; caseinkinase 1, New England Biolabs, P6030S, 2.5 µg/mL for Cys-βAla-Arg-Arg-Lys-Asp-Leu-His-Asp-Asp-Glu-Glu-Asp-Glu-Ala-Met-Ser-Ile-Thr-Ala-NH$_2$ and Cys-βAla-Arg-Arg-Lys-Asp-Leu-His-Asp-Asp-Glu-Glu-Asp-Glu-Ala-Met-Ala-Ile-Ala-Ala-NH$_2$), 100 µM/mL ATP and 100 µCi/mL γ-$^{32}$P-ATP (Amersham, 9.25 mBq/250 µCi/25 µL, activity>5000 Ci/mmol) in kinase buffer (50 mM tris-HCl, 150 mM NaCl, 30 mM MgCl$_2$, 4 mM DTT, 2 mM EGTA, pH 7.5) was spotted onto the peptide-modified glass surfaces and incubated for 30 min at room temperature in an almost water-saturated atmosphere. In order to reduce the background caused by the non-specific binding of ATP or kinase molecules to the glass surfaces, the modified glass surfaces were washed as follows:

three times for 3 minutes at room temperature using washing buffer (1% SDS and 1% Tween20 in 50 mM TRIS buffer, pH 7.5, 200 mM NaCl)

twice for 3 minutes at room temperature using 1M NaCl solution twice for 3 minutes at room temperature using distilled water twice for 3 minutes at room temperature using 80% formic acid in ethanol twice for 3 minutes at room temperature using distilled water twice for 5 minutes at 50° C. using a solution containing 6M urea, 2M thiourea and 1% SDS three times for 3 minutes at room temperature using distilled water three times for 3 minutes at room temperature using methanol After drying the glass surface the quantity of radioactive phosphate incorporated in the glass-surface-bound peptides was determined using a PhosphorImager system (FLA-3000, FUJIFILM) (see FIG. 1).

Example 30

Analysis of Kinase-mediated Peptide Modifications on Modified Glass Surfaces (See FIG. 2)

Surfaces (maleinimido-functionalised glass surface, see Example 1; maleinimidobutyryl-β-alaninine-functionalised cellulose and maleinimidobutyryl-β-alaninine-functionalised polypropylene membranes) modified with the peptide Cys-βAla-Leu-Arg-Arg-Ala-Ser-Leu-Gly-NH$_2$ and Cys-βAla-Leu-Arg-Arg-Ala-Ala-Leu-Gly-NH$_2$ were incubated with 10 mL of 100 µM ATP in kinase buffer (50 mM tris-HCl, 150 mM NaCl, 30 mM MgCl$_2$, 4 mM DTT, 2 mM EGTA, pH 7.5) for 10 minutes at room temperature. The surfaces were then coated with a mixture of protein kinase A (Sigma, P26452, U/mL), 100 µM/mL ATP and 100 µCi/mL γ-$^{32}$P-ATP (Amersham, 9.25 mBq/250 µCi/25 µL, activity>5000 Ci/mmol) in kinase buffer (50 mM tris-HCl, 150 mM NaCl, 30 mM MgCl$_2$, 4 mM DTT, 2 mM EGTA, pH 7.5) and incubated for 30 min at room temperature in an almost water-saturated atmosphere. In order to reduce the background caused by the non-specific binding of ATP or kinase molecules to the glass surfaces, the modified glass surfaces were washed as follows:

three times for 3 minutes at room temperature using washing buffer (1% SDS and 1% Tween20 in 50 mM TRIS buffer, pH 7.5, 200 mM NaCl)

twice for 3 minutes at room temperature using 1M NaCl solution twice for 3 minutes at room temperature using distilled water twice for 3 minutes at room temperature using 80% formic acid in ethanol twice for 3 minutes at room temperature using distilled water twice for 5 minutes at 50° C. using a solution containing 6M urea, 2M thiourea and 1% SDS three times for 3 minutes at room temperature using distilled water three times for 3 minutes at room temperature using methanol After drying the glass surface the quantity of radioactive phosphate incorporated in the glass-surface-bound peptides was determined using a PhosphorImager system (FLA-3000, FUJIFILM) (see FIG. 2).

Example 31

Analysis of Kinase-mediated Peptide Modifications on Various Modified glass Surfaces (See FIG. 3)

Surfaces (maleinimido-functionalised glass surface, see Example 1 and maleinimidobutyryl-β-alaninine-functionalised cellulose) modified with the peptide Cys-βAla-Leu-Arg-Arg-Ala-Ser-Leu-Gly-NH$_2$ were incubated with 10 mL of 100 µM ATP in kinase buffer (50 mM tris-HCl, 150 mM NaCl, 30 mM MgCl$_2$, 4 mM DTT, 2 mM EGTA, pH 7.5) for 10 minutes at room temperature. The surfaces were then mixed with a mixture of protein kinase A (Sigma, P26452, U/mL), 100 µM/mL ATP and 100 µCi/mL γ-$^{32}$P-ATP (Amersham, 9.25 mBq/250 µCi/25 µL, activity>5000 Ci/mmol) in kinase buffer (50 mM tris-HCl, 150 mM NaCl, 30 mM MgCl$_2$, 4 mM DTT, 2 mM EGTA, pH 7.5) and incubated for the specified times at room temperature in an almost water-saturated atmosphere. In order to reduce the background caused by the non-specific binding of ATP or kinase molecules to the glass surfaces, the modified glass surfaces were washed as follows:

three times for 3 minutes at room temperature using washing buffer (1% SDS and 1% Tween20 in 50 mM TRIS buffer, pH 7.5, 200 mM NaCl)

twice for 3 minutes at room temperature using 1M NaCl solution twice for 3 minutes at room temperature using distilled water twice for 3 minutes at room temperature using 80% formic acid in ethanol twice for 3 minutes at room temperature using distilled water twice for 5 minutes at 50° C. using a solution containing 6M urea, 2M thiourea and 1% SDS three times for 3 minutes at room temperature using distilled water three times for 3 minutes at room temperature using methanol After drying the glass surface the quantity of radioactive phosphate incorporated in the glass-surface-bound peptides was determined using a PhosphorImager system (FLA-3000, FUJIFILM) (see FIG. 3).

Example 32

Analysis of Kinase-mediated Peptide Modifications on Various Modified Glass Surfaces (See FIG. 8)

Precisely 43 serine- and/or threonine-containing peptides (potential substrate peptides for kinases) and the corresponding control peptides, each modified at the N-terminus with the dipeptide cysteinyl-β-alanine, were coupled to a maleinimido-functionalised glass surface by a Michael addition (see Example 18). The assembly of the peptides is shown in FIG. 8A. The numbering of the spots can be seen from FIG. 8C and the sequences of the peptides used are obtained from Example 18. After application of the peptide, the modified glass surface was first pre-incubated using 10 mL of 100 μM ATP ATP solution in 50 mM sodium phosphate buffer pH 7.5 for 10 for 10 minutes. The modified glass surface was then covered with a cover glass and protein kinase C (10 U/mL) together with ATP/γ-$^{32}$P-ATP mixture (100 μM/mL; 100 μCi/mL) was incorporated in the intermediate space formed by means of capillary force. Incubation was then carried out for 30 min at 25° C. In order to reduce the background caused by the non-specific binding of ATP or kinase molecules to the glass surfaces, the modified glass surfaces were washed as follows:

three times for 3 minutes at room temperature using washing buffer (1% SDS and 1% Tween20 in 50 mM TRIS buffer, pH 7.5, 200 mM NaCl)

twice for 3 minutes at room temperature using 1M NaCl solution twice for 3 minutes at room temperature using distilled water twice for 3 minutes at room temperature using 80% formic acid in ethanol twice for 3 minutes at room temperature using distilled water twice for 5 minutes at 50° C. using a solution containing 6M urea, 2M thiourea and 1% SDS three times for 3 minutes at room temperature using distilled water three times for 3 minutes at room temperature using methanol After drying the glass surface the quantity of radioactive phosphate incorporated in the glass-surface-bound peptides was determined using a PhosphorImager system (FLA-3000, FUJIFILM). The resulting image is shown in FIG. 8B. The spots of higher signal intensity in all three subarrays were assigned to the corresponding peptides phosphorylated by the protein kinase C. Their primary structures are shown in FIG. 8D. It is clear that the peptides known as protein kinase C substrates (substrate peptides Nos. 3, 23, 27, 41, 43) and other peptides not described as substrates for protein kinase C are recognised and phosphorylated by this kinase on the modified glass surface. It is thus clear that such an assembly is suitable for characterising the substrate specificity of a kinase, such as protein kinase C for example.

Example 33

Analysis of Kinase-mediated Peptide Modifications on Various Modified Glass Surfaces (See FIG. 9)

Precisely 43 serine- and/or threonine-containing peptides (potential substrate peptides for kinases) and the corresponding control peptides, each modified at the N-terminus with the dipeptide cysteinyl-β-alanine, were coupled to a maleinimido-functionalised glass surface by a Michael addition (see Example 18). The assembly of the peptides is shown in FIG. 8A. The numbering of the spots can be seen from FIG. 8C and the sequences of the peptides used are obtained from Example 18. After application of the peptide, the modified glass surface was first pre-incubated using 10 mL of 100 μM ATP solution in 50 mM sodium phosphate buffer pH 7.5 for 10 for 10 minutes. The modified glass surface was then covered with a cover glass and protein kinase A (10 U/mL) together with ATP/γ-$^{32}$P-ATP mixture (100 μM/mL; 100 μCi/mL) was incorporated in the intermediate space formed by means of capillary force. Incubation was then carried out for 30 min at 25° C. In order to reduce the background caused by the non-specific binding of ATP or kinase molecules to the glass surfaces, the modified glass surfaces were washed as follows:

three times for 3 minutes at room temperature using washing buffer (1% SDS and 1% Tween20 in 50 mM TRIS buffer, pH 7.5, 200 mM NaCl)

twice for 3 minutes at room temperature using 1M NaCl solution twice for 3 minutes at room temperature using distilled water twice for 3 minutes at room temperature using 80% formic acid in ethanol twice for 3 minutes at room temperature using distilled water twice for 5 minutes at 50° C. using a solution containing 6M urea, 2M thiourea and 1#% SDS three times for 3 minutes at room temperature using distilled water three times for 3 minutes at room temperature using methanol After drying the glass surface the quantity of radioactive phosphate incorporated in the glass-surface-bound peptides was determined using a PhosphorImager system (FLA-3000, FUJIFILM). The resulting image is shown in FIG. 9B. The spots of higher signal intensity in all three subarrays were assigned to the corresponding peptides phosphorylated by the protein kinase A. Their primary structures are shown in FIG. 9D. It is clear that with one exception, all the peptides on the modified glass surface are recognised and phosphorylated by protein kinase A which carries two arginine residues in position −2 and −3 (N-terminal) to the serine. This sequence motif RRxS is described as a preferred substrate motif for protein kinase A (A. Kreegipuu, N. Blom, S. Brunak, J. Jarv, 1998, Statistical analysis of protein kinase specificity determinants, *FEBS Lett.*, 430, 45-50). The peptide 83 is probably not phosphorylated because of the excessive N-terminal localisation of the substrate motif. It is thus clear that such an assembly is suitable for characterising the substrate specificity of a kinase, such as protein kinase A for example.

Example 34

Analysis of Kinase-mediated Peptide Modifications on Various Modified Glass Surfaces (See FIG. 10)

Precisely 79 peptides, each modified at the N-terminus with the dipeptide amino-oxyacetic acid-β-alanine, were coupled to an aldehyde-functionalised glass surface (see Example 20). The primary structure of the MBP is shown in FIG. 10C. For the residues shown in bold print a phosphorylation by protein kinase A was described in the prior art (A. Kishimoto, K. Nishiyama, H. Nakanishi, Y. Uratsuji, H. Numura, Y. Takeyama, Y. Nishizuka, 1985, Studies on the phosphorylation of myelin basic protein by protein kinase C and adenosine 3':5'-monophosphate-dependent protein kinase, *J. Biol. Chem.*, 260, 12492-12499). The 13-mer peptides in the scan show a sequence shift of two amino acids. The peptide assembly is shown in FIG. 10B. Thus, peptide No. 1 represents the amino acid sequence 1-13 of the primary structure of MBP, peptide No. 2 represents the amino acid sequence 3-15 of the primary structure of MBP, etc. Three identical subarrays are applied to the glass surface. One of these subarrays is shown in FIG. 10A. After application of the peptides, the modified glass surface was first pre-incubated for 10 minutes using 10 ml of 100 µM ATP solution in 50 mM of sodium phosphate buffer pH 7.5. The modified glass surface was then covered with a cover glass and Protein kinase A (10 U/mL) together with ATP/γ$^{32}$P-ATP mixture (100 µM/mL; 100 µCi/mL) was then inserted into the intermediate space formed thereby by means of capillary force. Incubation was then carried out for 30 min at 25° C. In order to reduce the background caused by the non-specific binding of ATP or kinase molecules to the glass surfaces, the modified glass surfaces were washed as follows:

three times for 3 minutes at room temperature using washing buffer (1% SDS and 1% Tween20 in 50 mM TRIS buffer, pH 7.5, 200 mM NaCl)

twice for 3 minutes at room temperature using 1M NaCl solution twice for 3 minutes at room temperature using distilled water twice for 3 minutes at room temperature using 80% formic acid in ethanol twice for 3 minutes at room temperature using distilled water twice for 5 minutes at 50° C. using a solution containing 6M urea, 2M thiourea and 1% SDS three times for 3 minutes at room temperature using distilled water three times for 3 minutes at room temperature using methanol After drying the glass surface the quantity of radioactive phosphate incorporated in the glass-surface-bound peptides was determined using a PhosphorImager system (FLA-3000, FUJIFILM). The resulting image is shown in FIG. 10A. The spots of higher signal intensity in all three subarrays were assigned to the corresponding peptides phosphorylated by the protein kinase A. Their primary structures are shown in FIG. 10D. It is clear that most of the peptides on the modified glass surface are recognised and phosphorylated by protein kinase A which was also found in the experiment carried out in solution (A. Kishimoto, K. Nishiyama, H. Nakanishi, Y. Uratsuji, H. Numura, Y. Takeyama, Y. Nishizuka, 1985, Studies on the phosphorylation of myelin basic protein by protein kinase C and adenosine 3':5'-monophosphate-dependent protein kinase, *J. Biol. Chem.*, 260, 12492-12499).

The features of the invention disclosed in the previous description, the examples, the claims, the drawings and the sequence protocol can both individually and in any combination be important for the implementation of the invention in its various embodiments.

The invention claimed is:

1. A method for determining a substrate specificity of at least one enzyme which comprises the steps of:
   providing an assembly comprising a plurality of amino acid sequences on a planar, non-porous surface of a support material wherein the amino acid sequences are substantially directionally immobilized in a single direction at either the N-terminus only or the C-terminus only of the amino acid sequences to the surface by reacting a defined reactive group on the amino acid sequence with a defined reactive group on the surface, wherein all amino acid sequences are immobilized using the same terminus and the same reactive group resulting in similar secondary and tertiary structures,
   contacting and/or incubating of the enzyme with the assembly,
   detecting a reaction between one or a plurality of amino acid sequences immobilized on the assembly and the enzyme, wherein during said reaction, a change in molecular weight of at least one of the amino acid sequences takes place, and
   determining substrate specificity of the enzyme based on an arrangement of said amino acid sequences at distinct locations.

2. The method according to claim 1, wherein the change in the molecular weight takes place by formation or cleaving of a covalent bond in the amino acid sequence which reacts with the enzyme.

3. The method according to claim 1, wherein the reaction is detected by detecting the change in the molecular weight.

4. The method according to claim 1, wherein the reaction is detected by a detection method selected from the group consisting of autoradiography, plasmon resonance spectroscopy and fluorescence spectroscopy.

5. The method according to claim 1, wherein at least one of the amino acid sequences is a substrate for the enzyme.

6. The method according to claim 1, wherein the assembly of amino acid sequences has at least one substrate for each of at least two different enzymes.

7. The method according to claim 1, wherein the enzyme is selected from the group consisting of an oxidoreductase, transferase, hydrolase, lyase and ligase.

8. The method according to claim 7, wherein the enzyme is selected from the group consisting of a kinase, sulphotransferase, glycosyl transferase, acetyl transferase, farnesyl transferase, palmytyl transferase, phosphatase, sulphatase, esterase, lipase, acetylase and protease.

9. The method according to claim 1, wherein the detection of a reaction between the amino acid sequences immobilized on the assembly and the enzyme is repeated many times at intervals of time.

10. The method according to claim 1, wherein the enzyme is determined in a sample and the sample is selected from the group comprising urine, sputum, stool, lymph fluid, body fluids, cell lysates, tissue lysates, organ lysates, extracts, raw extracts, purified preparations and unpurified preparations.

11. The method according to claim 1, wherein the support material is glass.

12. The method according to claim 1, wherein the amino acid sequence is immobilized via a sulphur-comprising group on the surface.

13. The method according to claim 1, wherein said distinct locations are not separated by a three-dimensional structure.

14. A method for determining a substrate specificity of at least one enzyme which comprises the steps of:
   providing an assembly comprising a plurality of amino acid sequences on a planar, non-porous surface of a support material wherein the amino acid sequences are bound to the planar, non-porous surface via a defined reactive group or collection of reactive groups such that all of the amino acid sequences in a distinct location are immobilized in a single direction at either the N-terminus or C-terminus by a chemoselective binding,
   contacting and/or incubating of the enzyme with the assembly,
   detecting a reaction between one or a plurality of amino acid sequences immobilized on the assembly and the enzyme, wherein during said reaction, a change in molecular weight of at least one of the amino acid sequences takes place, and
   determining substrate specificity of the enzyme based on an arrangement of said amino acid sequences at distinct locations.

* * * * *